(12) United States Patent
Lawrence et al.

(10) Patent No.: US 6,251,621 B1
(45) Date of Patent: *Jun. 26, 2001

(54) REPORTER ENZYME RELEASE TECHNOLOGY: METHODS OF ASSAYING FOR THE PRESENCE OF ASPARTIC PROTEASES AND OTHER HYDROLYTIC ENZYME ACTIVITIES

(75) Inventors: Paul J. Lawrence, Campbell; Aulena Churhuri; Terrence J. Andreasen, both of San Jose, all of CA (US)

(73) Assignee: Litmus Concepts, Inc., Santa Clara, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 08/406,239

(22) Filed: Mar. 17, 1995

Related U.S. Application Data

(63) Continuation of application No. 08/048,536, filed on Apr. 14, 1993, now Pat. No. 5,416,003.

(51) Int. Cl.[7] .................................................... C12Q 1/34
(52) U.S. Cl. ................................................................ 435/18
(58) Field of Search ................................. 435/7.36, 7.4, 435/7.72, 7.9, 7.91, 18, 23, 28, 31, 32, 34, 288, 180; 422/57, 518

(56) References Cited

U.S. PATENT DOCUMENTS

| | | | |
|---|---|---|---|
| 5,120,718 | * | 6/1992 | Goldman et al. ....................... 514/32 |
| 5,156,954 | * | 10/1992 | Mielke et al. .......................... 435/18 |
| 5,202,233 | * | 4/1993 | Herrmann et al. ..................... 435/7.4 |
| 5,416,003 | * | 5/1995 | Lawrence et al. ..................... 435/18 |

OTHER PUBLICATIONS

Zherdev A., Method of Proteolytic Activity Determination Using Bovine Serum Albumin Conjugate Jan. 1988, 1, ZH Microbiol Epimeriol Immuniobiol pp. 51–55, translation provided.*

* cited by examiner

*Primary Examiner*—Ralph Gitomer
(74) *Attorney, Agent, or Firm*—Townsend and Townsend and Crew LLP

(57) ABSTRACT

Methods of assaying for the presence of enzymatically active hydrolases (i.e., hydrolytic enzymes) in a sample or specimen are disclosed. In particular, a method of detecting candidiasis by assaying for the presence of enzymatically active aspartic protease in a sample is provided. In these methods, a sample or specimen is contacted with a solid support. The solid support with which the sample is contacted has a reporter enzyme (i.e., a signal generating enzyme) immobilized thereon. The reporter enzyme is immobilized on the solid support in a manner such that it is released from the solid support upon action of the enzymatically active hydrolase if the enzymatically active hydrolase is, in fact, present in the sample. The sample after having been contacted with the solid support is combined with an indicator. The indicator is any chemical species which is susceptible to a detectable change, usually a change in color, upon action of the reporter enzyme. A detectable change in the indicator is an indication that the enzymatically active hydrolase is present in the sample. Moreover, the presence of an enzymatically active hydrolase in a sample may indicate the presence of a particular pathogen or disease state such as, for example, candidiasis.

In addition to the methods of assaying for the presence of enzymatically active aspartic protease and other hydrolytic enzymes, a dry, self-contained test device for assaying for the presence of an enzymatically active hydrolase in a sample is disclosed. In particular, a dry, self-contained test device for testing a sample for the presence of candidiasis by assaying for the presence of enzymatically active aspartic protease is also disclosed. These test devices combine a reporter enzyme immobilized on a solid support, an indicator, and all other reagents and components necessary to achieve a detectable indication of the presence or absence of the enzymatically active hydrolase whose presence is being detected in the sample, and preferred embodiments contain positive and negative controls as well.

85 Claims, 2 Drawing Sheets

REPORTER ENZYME RELEASE TECHNOLOGY: METHODS OF ASSAYING FOR THE PRESENCE OF ASPARTIC PROTEASES AND OTHER HYDROLYTIC ENZYME ACTIVITIES

This is a Continuation of application Ser. No. 08/048,536 filed Apr. 14, 1993 now U.S. Pat. No. 5,416,003

FIELD OF THE INVENTION

This invention relates generally to methods of assaying for the presence of hydrolase activity (i.e., hydrolytic enzymes) in a sample or specimen. In particular, this invention relates to a method for detecting candidiasis by assaying for the presence of enzymatically active aspartic protease in a sample.

BACKGROUND OF THE INVENTION

*Candida albicans* and other Candida species cause a number of common, medically important infections. Oral candidiasis, for example, is very common in patients with immunodeficiency. Moreover, vulvovagina candidiasis is one of the most frequent disorders in obstetrics and gynecology. It has been estimated that approximately three-quarters of all adult women suffer from at least one attack of this disease. (De Bernardis, et al., *J. Clin. Microbiol.* 27(11) :2598–2603 (1989)). As a result of its wide-spread occurrence, extensive amounts of research have gone into understanding the etiology of candidiasis.

Research has demonstrated that *Candida albicans* and other Candida species have an etiological involvement in human candidiasis, and it is now generally believed that candidiasis is caused primarily by the presence of *Candida albicans*. Further, there is now considerable evidence for a role of an aspartic protease or (interchangeably) acid proteinase as a virulence factor of *Candida albicans*. It is known that pure cultures of *Candida aibicans* secrete an aspartic protease when grown under precisely defined conditions. Similarly, it is known that pure strains of *Candida aibicans* isolated from women with symptomatic vulvovaginitis release this enzyme when they are subsequently grown in specifically defined culture medium.

*Candida albicans* acid proteinase antigen, i.e., aspartic protease antigen, has been detected immunologic ally in the vaginal fluid of all women from which vulvovaginal *Candida albicans* was isolated. (De Bemnardis, et al., Abstract No. F-91 In: Abstracts of the Annual Meeting of the American Society for Microbiology, (Anaheim, Calif. 1990)). The concentration of *Candida albicans* acid proteinase antigen, however, was significantly higher in patients with symptomatic vulvovaginal candidiasis than in asymptomatic carriers. The vaginal fluid concentration of this antigen in women with candidiasis is approximately 176±15.2 ng/mL, whereas the vaginal fluid concentration of this antigen in women without isolation of *Candida albicans*, i.e., without clinical candidiasis, was less than 2 ng/ml. Asymptomatic *Candida albicans* carriers had intermediate antigen levels (94±18.5 ng/ml). These findings are a strong indication that acid proteinase (i.e., aspartic protease) is involved in the pathogenesis of vulvovaginal candidiasis. *Candida albicans* aspartic protease, however, is known to be unstable at body temperatures. Moreover, detection of the aspartic proteinase antigen immunologically did not indicate whether the enzyme was present in an enzymatically active form.

*Candida albicans* acid proteinase is an extracellular aspartic protease. Aspartic proteases are one of the major classes of proteases. They contain one or more key aspartic acid residues which are required for activity. *Candida albicans* aspartic protease has a broad protein substrate specificity which includes, for example, albumin, hemoglobin, casein, immunoglobin A, and many other proteins. This enzyme performs optimally under acidic conditions (i.e., pH 2.5–5.5), and it is rapidly inactivated at a high pH (i.e, at pH 7.5). *Candida albicans* aspartic protease is strongly inhibited by pepstatin, but it is not inhibited by thiol reagents, chelators or serine protease inhibitors.

Many pharmaceutical companies and leading academicians are studying aspartic protease inhibitors for potential therapeutic use. Their efforts, however, are made difficult due to a lack of a suitable enzyme assay for aspartic proteases. While simple colorimetric assays are available for some serine, thiol, metallo, acid, and alkaline proteases and peptidases, they are not available for aspartic proteases. The substrate specificity of this particular class of enzymes requires the presence of several hydrophobic amino acids. This property has greatly hindered the search for simple synthetic chromogenic substrates because the hydrophobic amino acids which serve as the substrate for aspartic proteases are notoriously difficult to dissolve in water. As a result, chromogenic substrates for aspartic protease are not commercially available, are difficult to synthesize and characterize, and are poorly water soluble. The net effect of these limitations is that the enzyme activity as defmed by these chromogenic substrates is extremely low and thus, colorimetric assays for aspartic protease are quite insensitive. Similarly, fluorogenic substrates have been described for aspartic proteases, but they, too, are of limited utility. First, as previously mentioned, the substrate specificity of this particular class of enzymes requires the presence of several hydrophobic amino acids, rendering the substrates relatively insoluble. Second, at the low achievable concentrations of these substrates, the fluorogenic substrates are hydrolyzed very slowly and thus, fluorogenic assays are time-consuming. In addition, many biological specimens contain fluorescent materials which can interfere with fluorogenic assays for aspartic proteases.

Due to the lack of suitable colorimetric or fluorogenic assays for the detection of aspartic proteases, ultraviolet (UV) spectrophotometric assays are generally used to assay for the presence of this particular class of enzymes. In typical UV spectrophotometric assays, aspartic protease is added to a solution of protein (such as, for example, hemoglobin or albumin) and the mixture is incubated at 30–37° C. for 0.5 to 4 hours. After incubation, cold, concentrated trichloroacetic acid (TCA) is added to the chilled incubation mixture to precipitate the undigested protein, leaving ultraviolet light absorbing peptides in solution. Finally, the precipitated, undigested protein is pelleted by centrifugation for approximately 1 hour at refrigerated temperatures, the supernatant aspirated, and its Optical Density at 280 nm is determined to reflect the amount of protein hydrolysis. Although this assay can be used for the detection of aspartic proteases, it is both time-consuming and laborious.

To date, therefore, no convenient, simple, on-site assay has been developed for detecting the presence of enzymatically active aspartic proteases. Accordingly, the present invention is directed to a method of assaying for the presence of enzymatically active aspartic proteases which overcomes the problems and disadvantages of the prior art. Further, the methods of the present invention are also useful for assaying for the presence of other known hydrolytic enzymes, i.e., hydrolases.

SUMMARY OF THE INVENTION

It has now been discovered that enzymatically active *Candida albicans* aspartic protease is present in the vaginal fluid of women with vulvovaginal candidiasis. It has further been discovered that the presence of enzymatically active aspartic protease in a sample or specimen can serve as a marker for the detection and diagnosis of candidiasis. Accordingly, a method has now been developed for detecting candidiasis by assaying for the presence of enzymatically active aspartic protease in a sample.

In this method, a sample, e.g., vaginal fluid, is contacted with a solid support. The solid support with which the sample is contacted has a reporter enzyme (i.e., a signal generating enzyme) immobilized thereon. The reporter enzyme is immobilized on the solid support in a manner such that it is released from the solid support upon action of the enzymatically active aspartic protease if the enzymatically active aspartic protease is, in fact, present in the sample. The sample after having been contacted with the solid support is combined with an indicator. The indicator is any chemical species which is susceptible to a visible or detectable change (such as, for example, a change in color) upon action of the reporter enzyme. If after contact with the sample the indicator undergoes a detectable change, enzymatically active aspartic protease is present in the sample and, hence, it can be said that candidiasis is present.

Prior to the present invention, there was no rapid and straightforward means of assaying for the presence of enzymatically active aspartic proteases or, more importantly, candidiasis. Spectrophotometric, fluorogenic and immunological assays have been used to assay for the presence of aspartic protease activity, but these assays are time-consuming, laborious and not suitable for use by untrained, on-site clinical personnel. Similarly, *Candida albicans* can be detected by culturing a specimen in a defined media or by wet mount microscopy. The culturing procedure is very time-consuming (i.e., it takes approximately 48 hours), and both procedures require expensive equipment and extensive training. In contrast to previously used assays, the presently claimed method of assaying for the presence of enzymatically active aspartic protease and, in turn, candidiasis is rapid, accurate, cost-effective, and simple to use.

The reporter enzyme release technology upon which the aspartic protease assay is based can also be used to assay for the presence of any active hydrolytic enzyme including, but not limited to, the following: proteases or (interchangeably) proteinases, peptidases, lipases, nucleases, homo-oligosaccharidases, hetero-oligosaccharidases, homo-polysaccharidases, hetero-polysaccharidases, phosphatases, sulfatases, neuraminidases and esterases. Accordingly, methods of assaying for the presence of an enzymatically active hydrolase in a sample have now been developed.

In these methods, a sample or specimen is contacted with a solid support. The solid support with which the sample is contacted has a reporter enzyme (i.e., a signal generating enzyme) immobilized thereon. The reporter enzyme is immobilized on the solid support in a manner such that it is released from the solid support upon action of the hydrolase if the enzymatically active hydrolase is, in fact, present in the sample. The sample after it has been contacted with the solid support is combined with an indicator. The indicator is any chemical species which is susceptible to a detectable change, usually a change in color, upon action of the reporter enzyme. A detectable change in the indicator is an indication that the enzymatically active hydrolase is present in the sample. Conversely, the lack of a detectable change in the indicator is an indication that the enzymatically active hydrolase is absent from the sample. As with the assay for enzymatically active aspartic protease and, in turn, candidiasis, the presently claimed methods of assaying for the presence of an enzymatically active hydrolase in a sample are rapid, accurate, cost-effective, and simple to use.

Moreover, the reporter enzyme release technology upon which the above methods are based can also be used to assay for the presence of an inhibitor of any known hydrolytic enzyme, including, but not limited to, the following: inhibitors of the proteases or (interchangeably) proteinases, peptidases, lipases, nucleases, homo-oligosaccharidases, hetero-oligosaccharidases, homo-polysaccharidases, hetero-polysaccharidases, phosphatases, sulfatases, neuraminidases and esterases. Accordingly, methods of assaying for the presence of a hydrolase inhibitor in a sample have now been developed.

In these methods, a sample or specimen is contacted with a target hydrolase and a solid support. The solid support with which the sample is contacted has a reporter enzyme (i.e., a signal generating enzyme) immobilized thereon. The reporter enzyme is immobilized on the solid support in a manner such that it is released from the solid support upon action of the target hydrolase provided the target hydrolase is not inactivated due to the presence of the hydrolase inhibitor. The sample after it has been contacted with the target hydrolase and the reporter enzyme is combined with an indicator. The indicator is any chemical species which is susceptible to a detectable change, usually a change in color, upon action of the reporter enzyme if the reporter enzyme has been released from the solid support by the target hydrolase. In the event that the target hydrolase inhibitor is not present in the sample, the target hydrolase will release the reporter enzyme from the support, thereby producing a detectable change in the indicator. Conversely, if the target hydrolase inhibitor is present in the sample, the target hydrolase will be inhibited, the reporter enzyme will not be released from the solid support, and a detectable change or response will not be produced in the indicator. As with the previously described methods, the presently claimed methods of assaying for the presence of a hydrolase inhibitor in a sample are rapid, accurate, cost-effective, and simple to use.

In addition to the methods of assaying for the presence of enzymatically active aspartic protease and the activities of other hydrolytic enzymes, a dry, self-contained test device has now been developed for testing a sample for the presence of candidiasis by assaying for the presence of enzymatically active aspartic protease. Furthermore, a dry, self-contained test device for assaying for the presence of an enzymatically active hydrolase in a sample has also been developed. These test devices combine a reporter enzyme immobilized on a solid support, an indicator, and one or more other reagents in dry form in a laminated panel with an internal chamber, the chamber being a void space until the sample is placed inside. For convenience, the parts of the panel and the locations of the functional chemicals in the panel will be described from a frame of reference in which the panel is in a horizontal position, since this is the most likely position which the panel will occupy during use. With the panel in this position, particularly for the preferred panels of this invention which are thin, flat structures, the sample will be placed in the chamber through an opening at the top of the panel. Of the laminae forming the panel, the uppermost lamina in this position, this lamina being the one through which the sample is introduced, will be referred to as the top lamina of the panel, the lower surface of this lamina forming the upper surface of the chamber. Likewise, the lowermost lamina of the panel will be referred to as the bottom lamina of the panel, the upper surface of this bottom lamina forming the lower surface of the chamber. The thin edges along the perimeters of these top and bottom laminae will be referred to as the side edges of the panel, and the thin lateral extremities of the chamber along the edges of its upper and lower surfaces will be referred to as the side walls of the chamber. Regions of any given surface which are adjacent to each other in the same horizontal plane will be referred to as horizontally adjacent, whereas lamina applied directly over other laminae to form parallel horizontal planes will be referred to as vertically adjacent.

The top, bottom, or both laminae of the panel are fabricated of a light-transmitting, preferably transparent, material. The reporter enzyme immobilized on a solid support, indicator and other components and reagents needed for the test are arranged in one or more laminae within the chamber, either as coatings on the upper surface of the chamber, as coatings on the lower surface of the chamber, or on both. The indicator is any chemical species which is susceptible to a detectable change, usually a color change, upon action of the reporter enzyme when it is released from the solid support by the enzymatically active hydrolase whose presence is being detected. The lamina containing the indicator may be on the upper or lower surface of the chamber. One or more of the reagents needed for the test may be included in the same lamina as the indicator, or in separate laminae on the same surface or on the opposite surface. In certain preferred embodiments of the invention, the indicator is contained in the lamina applied directly underneath a light-transmitting wall and the reporter enzyme immobilized on the solid support is contained in the lamina applied to the opposing wall.

The reagents occupying the laminae may be selected such that all that is needed to complete the test is the addition of the sample plus a minimal number of additional reagents such as, for example, a developer. In particularly preferred embodiments, however, the laminae contain all reagents needed other than the sample, so that performance of the test requires nothing more than addition of the sample.

All laminae are solid layers prior to contact with the sample, and the lamina containing the indicator is preferably of a composition which is insoluble in the liquid sample for which the test is designed, so that the indicator remains in the lamina throughout the duration of the test. For samples in either aqueous or water-soluble media, therefore, the preferred indicator lamina is either an indicator which is insoluble in water or an indicator held in a matrix which is insoluble in water. With the indicator thus retained in a thin concentrated lamina directly underneath a light-transmitting wall, a change in the indicator which is detectable through the light-transmitting wall occurs in a short period of time, resulting in both high sensitivity and a fast result.

This invention may be adapted and used for tests for a wide variety of hydrolases in test samples from a wide variety of sources. Moreover, this invention may be adapted and used for tests for a wide variety of hydrolase inhibitors. A test may involve either a single reaction or a sequence of reactions culminating in a detectable change in the indicator, and the number and types of reagents and reactions will accordingly vary from one test to the next depending on which hydrolase is being detected. In some cases, best results are obtained when the pre-applied reacting species are distributed between the upper and lower surfaces of the chamber such that they are separated by a gap until the gap is filled with the test sample. In other cases, the reacting species may be placed in a common lamina or in two or more distinct but vertically adjacent laminae on the upper or lower surface of the chamber with no loss in the reliability of the test. In all cases, however, the laminae are constituted and arranged such that the reactions which culminate in the detectable indicator change occur only when the chamber is filled with the test sample, and such that when the indicator change does occur, it is at least concentrated in, and preferably restricted to, the lamina immediately adjacent to a light-transmitting wall.

In preferred embodiments of the invention, the test device includes a built-in positive control, a built-in negative control, or both, all of which are activated by the addition of a single specimen. The activation of these controls occurs simultaneously with the performance of the test, and detectable indications (such as, for example, color changes or the lack thereof) representing both the controls and the test, are achieved with a single application of the specimen to the device and are detectable through a light-transmitting wall. The controls occupy positions on the device which are horizontally adjacent to the test area, with appropriate indicia on the upper or lower surface of the device, preferably the upper, to identify the controls and differentiate them from the test. The controls themselves generally consist of further laminae containing reagents or other appropriate species which will either induce the detectable change in the indicator by themselves or prevent the change from occurring, and will do so only when the test sample is present and yet independently of the presence or absence of the suspect hydrolase in the test sample. Again, the choice of these controls and the chemical mechanisms by which they function, as well as the choice between placing these laminae on the same surface of the chamber as the indicator or on the opposing surface, will vary from one test to the next.

Further preferred embodiments of the invention contain additional features to enhance the performance of the test. For water-based samples, the incorporation of a surface-active agent in the laminae immediately adjacent to the gap to be filled with the sample will promote the wetting of the laminae with the sample and the rapid and uniform filling of the chamber. The surface-active agent may be the sole functional ingredient in the lamina or combined in the lamina with test reagents. Preferably, both sides of the gap are lined with laminae bearing the surface-active agent. A sample introduction port is included in the device to permit direct insertion of the sample into the chamber, and preferred embodiments include one or more vent holes in the chamber, spaced apart from the sample introduction port, to further facilitate the filling of the chamber.

Other features, objects and advantages of the invention and its preferred embodiments will become apparent from the description which follows.

DETAILED DESCRIPTION OF THE INVENTION AND PREFERRED EMBODIMENT

Figure 1:
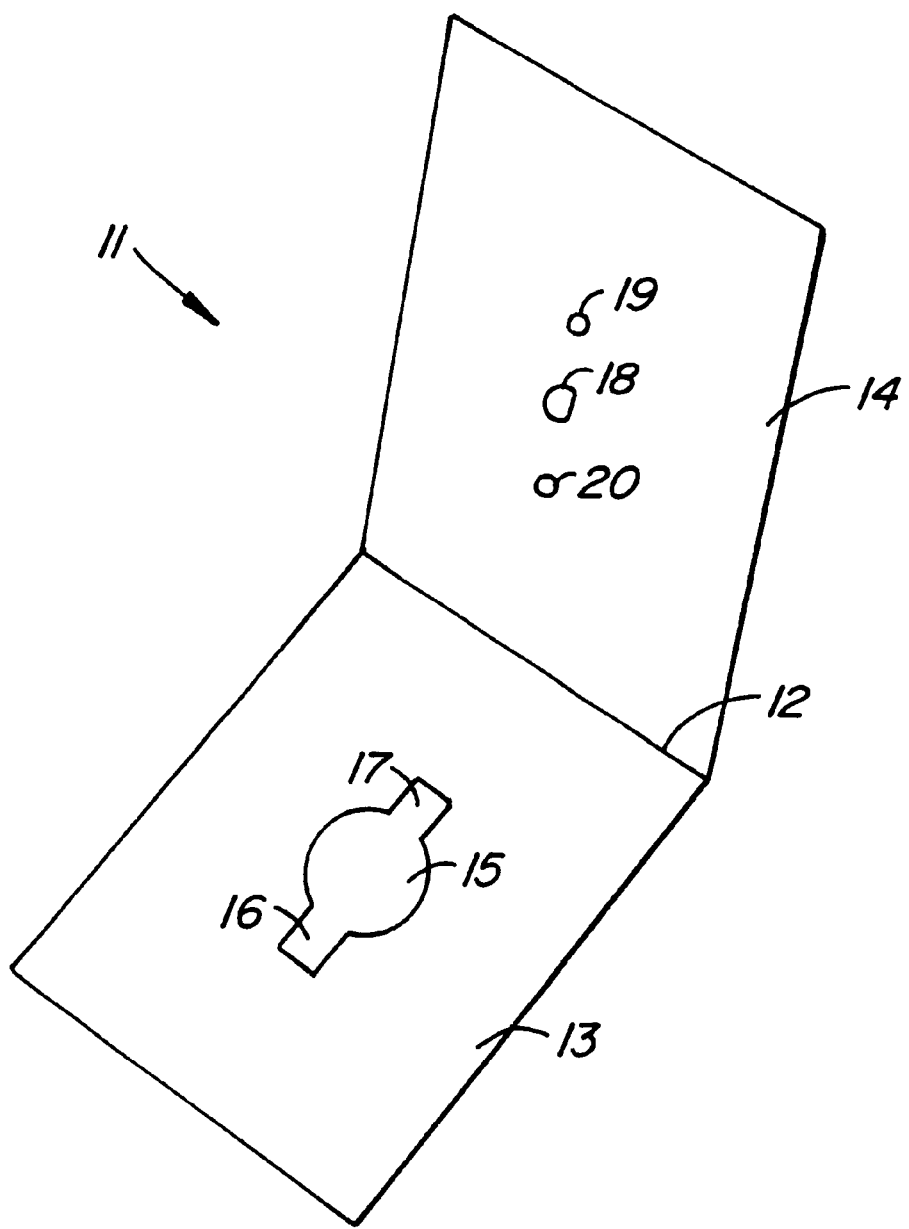
FIG. 1 is a view in perspective of an illustrative test device in accordance with the invention.

In one aspect of the present invention, a method of assaying for the presence of an enzymatically active hydrolase in a sample is provided, the method comprising: (a) contacting the sample with a solid support, the solid support having a reporter enzyme immobilized thereon in such a manner whereby the reporter enzyme is released upon action of the hydrolase; (b) combining the sample after it has been contacted with the solid support with an indicator, the indicator being one which is susceptible to a detectable change upon action of the reporter enzyme; and (c) observing whether the indicator undergoes a detectable change, the detectable change being an indication of the presence of the enzymatically active hydrolase in the sample.

The term "hydrolase" is used herein to refer to an enzyme which catalyzes hydrolytic reactions. The method of the present invention can be used to assay for the presence of any known hydrolytic enzyme. Such hydrolytic enzymes, i.e., hydrolases, include, but are not limited to, the following: proteases or (interchangeably) proteinases, peptidases, lipases, nucleases, homo- or hetero-oligosaccharidases, homo- or hetero-polysaccharidases, phosphatases, sulfatases, neuraminidases and esterases. In a preferred embodiment, the method of the present invention can be used to assay for the presence of proteases, including, but not limited to, the following: aspartic proteases, serine proteases, thiol proteases, metallo proteases, acid proteases, and alkaline proteases. In another preferred embodiment, the method of the present invention can be used to assay for the presence of homo- or hetero-oligosaccharidases or homo- or hetero-polysaccharidases, including, but not limited to, chitinase, amylases, cellulase and lysozyme.

The term "reporter enzyme" or (interchangeably) "marker enzyme" is used herein to refer to a signal generating enzyme, i.e., an enzyme whose activity brings about a detectable change. Such reporter enzymes include, but are not limited to, the following: peroxidases, phosphatases, oxidoreductases, dehydrogenases, transferases, isomerases, kinases, reductases, deaminases, catalases, urease and glucuronidase. In selecting a reporter enzyme to be used in the presently claimed method, it is imperative that the reporter enzyme is not subject to inactivation by any agent in the sample, including inactivating hydrolysis by any hydrolase activity present in the sample. The selection of an appropriate reporter or marker enzyme will be readily apparent to those skilled in the art. Presently preferred reporter enzymes are the peroxidases, such as, for example, horseradish peroxidase.

The reporter enzyme is immobilized on a solid support, i.e., an insoluble polymeric material, inorganic or organic matrix, gel, aggregate, precipitate or resin, in such a manner whereby the reporter enzyme is released upon action of the hydrolase whose presence is being assayed. Preferred solid supports in accordance with the present invention include, but are not limited to, the following: cellulose, agarose, dextran, polyacrylate, polyacrylamide, or their derivatives, chitin, sepharose, oxirane acrylic beads and polymeric dialdehyde, starch, collagen, keratin, elastin, bovine hide powder, bacterial cell wall peptidoglycan or fragments thereof, nylon, polyethylene terephthalates, polycarbonates, and controlled pore glass. Immobilization of the reporter enzyme on the solid support is carried out using conventional methods and procedures known to and understood by those skilled in the art.

The reporter enzyme can be attached directly to the solid support. In this case, the insoluble support serves directly as a substrate for the hydrolase. For example, when chitinase is the hydrolase being assayed, the reporter or marker enzyme (such as, for example, horseradish peroxidase) can be attached directly to the insoluble chitin. In the presence of chitinase, horseradish peroxidase will be released from the solid support. Similarly, if cellulase is the hydrolase being detected, the reporter enzyme, e.g., horseradish peroxidase, can be directly attached to cellulose, and in the presence of the hydrolase cellulase, horseradish peroxidase will be released from the solid support. Finally, if lysozyme is the hydrolase being detected, the reporter enzyme, e.g., horseradish peroxidase, can be directly attached to bacterial cell wall peptidoglycan, and in the presence of the hydrolase lysozyme, horseradish peroxidase will be released from the solid support.

Alternatively, the reporter enzyme can be immobilized on the solid support through the use of a linker molecule which is a hydrolyzable substrate for the hydrolase being detected. Such linker molecules include, but are not limited to, the following: proteins, carbohydrates, lipids, peptides, esters and nucleic acids. The particular linker molecule used to attach the reporter enzyme to the solid support will depend on which hydrolase is being detected, and the selection in any given case will be readily apparent to those skilled in the art.

The term "indicator" is used herein to refer to any chemical species which undergoes a detectable change as a result of the reaction or as a result of the culmination of reactions occurring when the enzymatically active hydrolase is present in the sample or specimen. The resulting detectable change is an indication that the enzymatically active hydrolase is present in the sample or specimen.

Preferred indicators are visual indicators and, in particular, chromogenic indicators, i.e., those in which the visible change is a change in color, including the formation of color in an otherwise colorless material, upon action of the reporter or marker enzyme when it is released from the solid support by the enzymatically active hydrolase whose presence is being detected. Alternatively, the reporter enzyme may be capable of catalyzing the formation of a fluorescent signal, a phosphorescent signal, a bioluminescent signal, a chemiluminescent signal, or an electrochemical signal upon its release from the solid support by the action of the hydrolase. Additionally, the reporter enzyme may be capable of producing other visible or detectable signals, such as, for example, a clot, an agglutination, a precipitation, or a clearing zone. In these cases, the indicator would be the chemical species or substrate required by the reporter or marker enzyme in order to bring about the desired detectable change.

A wide variety of chromogenic indicators (i.e., chromogens) and other species having a similar effect may be used as visual indicators with horseradish peroxidase as the reporter enzyme. Preferred chromogenic indicators in accordance with the present invention comprise a hydroperoxide and a chromogen including, but not limited to, one of the following: guaiac, 2-2'-azino-bis(3-ethyl-benthiazoline-6-sulfonic acid), tetramethylbenzidine, phenol, 4-aminoantipyrine, and 4,5-dihydroxynaphthalene-2,7-disulfonic acid. A particularly preferred chromogenic indicator is comprised of a hydroperoxide and guaiac, a chromogen which is colorless in its reduced state and deep blue in its oxidized state. Optionally, guaiac may be purified prior to use, e.g., by solvent extraction. The most appropriate chromogenic indicator for any given reporter enzyme will depend upon the reaction or reactions which the reporter enzyme is capable of catalyzing or initiating, and the selection in any given case will be readily apparent to those skilled in the art.

If the visual indicator is a chromogenic indicator, it is possible to employ either a liquid chromogen system or a solid chromogen system. If a liquid chromogen system for detecting peroxidases is used, such a system would comprise a solvent, a hydroperoxide and a chromogen capable of being oxidized by hydroperoxides in the presence of a peroxidase, such as, for example, horseradish peroxidase. Alternatively, if a solid chromogen system is used, such a system would comprise a hydroperoxide, a chromogen capable of being oxidized by hydroperoxides in the presence of a peroxidase, and a solid support onto which the chromogen has been impregnated or immobilized and dried. In this system, the chromogen can be impregnated onto a bibulous paper or support as is done with Hemoccult® slides or, alternatively, the chromogen can be deposited onto a plastic or other sheet in the form of a thin layer. In this latter format, the chromogen could be layered as a solution containing a polymeric material (such as, for example, hydroxypropyl cellulose, ethyl cellulose, etc.). If the chromogen itself is a water soluble chromogen, it can be trapped in a matrix of material which is insoluble in water. Alternatively, if the chromogen itself is insoluble in water, it can be layered as a solution in an organic solvent either alone or in combination with a water soluble or water insoluble polymer.

In the solid chromogen system for detecting peroxidases, the hydroperoxide can be provided either in a solid form (such as, for example, titanium hydroperoxide) or it can be generated in situ. Hydrogen peroxide, for example, can be generated in situ with glucose, ambient oxygen and glucose oxidase. Alternatively, hydrogen peroxide can be generated in situ through the use of a dried layer formed after depositing a suspension of sodium perborate in alcohol. At low pH, sodium perborate releases hydrogen peroxide spontaneously. In the presence of the hydrogen peroxide and the peroxidase upon its release from the solid support by the hydrolase, the chromogen will be oxidized and a visually detectable change in color will result. This resulting change in color is an indication that the enzymatically active hydrolase is present in the sample or specimen.

This method as well as the other methods of the presently claimed invention can be used to simultaneously assay for the presence of two or more active hydrolases in a sample or specimen. Such a method would employ a mixture of two or more reporter enzymes immobilized on a solid support(s) through substrate linkages which are susceptible to specific hydrolases, and two or more indicator and reagent systems to generate a detectable response to each of the reporter enzymes. For example, it would be possible using the methods of the present invention to detect simultaneously a mixture of proteases, lipases and polysaccharidases, thereby obtaining a hydrolytic profile of a given pathogen or disease process.

Additionally, it will be readily apparent to those skilled in the art that the reactions conditions (such as, for example, the choice of the linker molecule or bridge, solid supports, pH, buffer capacity, buffer identity, salts, etc.) of the presently claimed methods can be modified and regulated to increase hydrolase specificity and to differentiate between the different hydrolases present in a sample. For example, it is known that certain hydrolase function at a low pH and are inhibited at a high pH. In contrast, other hydrolases function at a high pH and are inhibited at a low pH. By regulating the pH of the assay, one will be able to selectively detect the presence of a particular hydrolase. Additionally, it will be readily apparent to the skilled artisan that specific enzyme inhibitors can also be used in the presently claimed methods to increase hydrolase activity and specificity and to differentiate between the different hydrolases.

In another aspect of the present invention, a method for assaying for the presence of an enzymatically active hydrolase in a sample is provided, the method comprising: placing the sample in a device which contains first and second solid supports, the first solid support having a reporter enzyme immobilized thereon in such a manner whereby the reporter enzyme is released upon action of the hydrolase, the second solid support, which is not in contact with the first solid support, having immobilized thereon an indicator, the indicator being one which is susceptible to a detectable change upon action of the reporter enzyme, the sample being placed in the device in such a manner that the sample contacts the first and second solid supports such that any reporter enzyme released by any hydrolase activity present in the sample is permitted to diffuse through the sample to the second solid support; and observing whether the indicator undergoes a detectable change, the detectable change being an indication of the presence of the enzymatically active hydrolase in the sample.

This method of the present invention can also be used to assay for the presence of any known hydrolytic enzyme, including, but not limited to, the following hydrolases: proteases or (interchangeably) proteinases, peptidases, lipases, nucleases, homo- or hetero-oligosaccharidases, homo- or hetero-polysaccharidases, phosphatases, sulfatases, neuraminidases and esterases. In a preferred embodiment, this method is used to assay for the presence of proteases, including, but not limited to, the following: aspartic proteases, serine proteases, thiol proteases, metallo proteases, acid proteases and alkaline proteases.

The reporter enzyme or marker enzyme used in this method can be any signal generating enzyme not subject to inactivation by any agent in the sample, including inactivating hydrolysis by any hydrolase activity present in the sample. Such reporter enzymes include, but are not limited to, the following: peroxidases, phosphatases, oxidoreductases, dehydrogenases, transferases, isomerases, kinases, reductases, deaminases, catalases, urease and glucuronidase. Presently preferred reporter or marker enzymes are the peroxidases, such as, for example, horseradish peroxidase.

The reporter enzyme is immobilized on a first solid support, i.e., an insoluble matrix, gel or resin, in such a manner whereby the reporter enzyme is released from the solid support upon action of the enzymatically active hydrolase whose presence is being assayed. The reporter enzyme can be attached directly to the first solid support if the solid support is a substrate for the hydrolase or, alternatively, the reporter enzyme can be immobilized on the first solid support through the use of a linker molecule which is a substrate for the enzymatically active hydrolase which is being detected. Such linker molecules include, but are not limited to, the following: proteins, carbohydrates, lipids, peptides, esters and nucleic acids. The particular linker molecule used to attach the reporter enzyme to the first solid support will depend on which hydrolase is being detected, and the selection in any given case will be readily apparent to those skilled in the art. Immobilization of the reporter enzyme on the first solid support is carried out using conventional methods and procedures known to and understood by those skilled in the art.

In this method of the present invention, the indicator is attached to the second solid support which is not in contact with the first solid support. Preferred first and second solid supports in accordance with the present invention include, but are not limited to, the following: cellulose, agarose, dextran, polyacrylate, polyacrylamide, or their derivatives chitin, sepharose, oxirane acrylic beads, polymeric dialdehyde, starch, collagen, keratin, elastin, bovine hide powder, bacterial cell wall peptidoglycan or fragments thereof, nylon, polyethylene terephthalates, polycarbonates, and controlled pore glass. Immobilization of the visual indicator on the second solid support is carried out using conventional methods and procedures known by those skilled in the art.

The indicator can be any chemical species which undergoes a detectable change as a result of the reaction or as a result of the culmination of reactions occurring when the enzymatically active hydrolase is present in the sample or specimen. The resulting detectable change in the indicator is an indication that the enzymatically active hydrolase is present in the sample. Preferred indicators are visual indicators and, in particular, chromogenic indicators, i.e., those in which the visible change is a change in color, including the formation of color in an otherwise colorless material, upon action of the reporter or marker enzyme when it is released from the solid support by the enzymatically active hydrolase whose presence is being detected.

A wide variety of chromogenic indicators (i.e., chromogens) and other species having a similar effect may be used as visual indicators. Preferred chromogenic indicators for peroxidase-like reporter enzymes in accordance with the present invention comprise a hydroperoxide and a chromogen including, but not limited to, one of the following: guaiac, 2-2'-azino-bis(3ethyl-benthiazoline-6-sulfonic acid), tetramethylbenzidine, phenol, 4-aminoantipyrine, and 4,5-dihydroxynaphthalene-2,7-disulfonic acid. A particularly preferred chromogenic indicator is comprised of a hydroperoxide and guaiac, a chromogen which is colorless in its reduced state and deep blue in its oxidized state. The most appropriate chromogenic indicator for any given reporter enzyme will depend on the reaction or reactions which the reporter enzyme is capable of catalyzing or initiating, and the selection in any given case will be readily apparent to those skilled in the art.

If the visual indicator is a chromogenic indicator for peroxidative reactions, a solid chromogen system is employed, and such a system comprises a hydroperoxide, a chromogen capable of being oxidized by hydroperoxides in the presence of a peroxidase, and a solid support onto which the chromogen has been impregnated or immobilized and dried. In this system, the chromogen can be impregnated onto a bibulous paper or support as is done with Hemoccult® slides or, alternatively, the chromogen can be deposited onto a plastic or other sheet in the form of a thin layer. In this latter format, the chromogen could be layered as a solution containing a polymeric material (such as, for example, hydroxypropyl cellulose, ethyl cellulose, etc.). If the chromogen itself is a water soluble chromogen, it can be trapped in a matrix of material which is insoluble in water. Alternatively, if the chromogen itself is insoluble in water, it can be layered as a solution in an organic solvent either alone or in combination with a water soluble or water insoluble polymer.

In the solid chromogen system, the hydroperoxide can be provided either in a solid form (such as, for example, titanium hydroperoxide) or it can be generated in situ in the device. In the presence of the hydroperoxide and the peroxidase upon its release from the first solid support by the hydrolase, the chromogen will be oxidized and a visually detectable change in color will result. This resulting change in color is an indication of the presence of the enzymatically active hydrolase in the sample or specimen.

In a presently preferred embodiment of this method of the present invention, enzymatically active aspartic protease is the hydrolase being detected, the method comprising: placing the sample in a device which contains first and second solid supports, the first solid support being polyacrylate and having horseradish peroxidase immobilized thereon through a myoglobin molecule which is a substrate for aspartic protease, the second solid support, which is not in contact with the first solid support, being a cellulose derivative and having immobilized thereon a hydroperoxide and guaiac, a chromogenic substrate which undergoes a color change upon action of horseradish peroxidase in the presence of a hydroperoxide, the sample being placed in the device in such a manner that the sample contacts the first and second solid supports such that any horseradish peroxidase released by any enzymatically active aspartic protease present in the sample is permitted to diffuse through the sample to the second solid support; and observing whether guaiac undergoes a color change, the color change being an indication of the presence of enzymatically active aspartic protease in the sample.

As previously mentioned, it will be readily apparent to the skilled artisan that particular reaction conditions (such as, for example, the choice of linker molecule, solid support, pH, buffer capacity, buffer identity, salts, etc.) and specific inhibitors can used to increase aspartic protease specificity. For example, by assaying for aspartic protease at a pH of about 2.5 to about 5.0, one can selectively detect aspartic proteases over many thiol proteases, serine proteases, metallo proteases, and alkaline proteases. Further, by adding inhibitors of the metallo-proteases, the thiol proteases, the serine proteases, and the acid or alkaline proteases, one can selectively detect aspartic proteases.

In still another aspect of the present invention, a method for detecting candidiasis by assaying for the presence of enzymatically active aspartic protease in a sample is provided, the method comprising: (a) contacting the sample with a solid support, the solid support having a reporter enzyme immobilized thereon in such a manner whereby the reporter enzyme is released upon action of the aspartic protease; (b) combining the sample after having been contacted with the solid support with an indicator, the indicator being one which is susceptible to a detectable change upon action of the reporter enzyme; and (c) observing whether the indicator undergoes a detectable change, the detectable change being an indication of the presence of enzymatically active aspartic protease in the sample and thus, candidiasis.

The reporter enzyme or marker enzyme used in this method of the present invention can be any signal generating enzyme, i.e., an enzyme whose activity brings about a visible or detectable change, not subject to inactivation by any agent in the sample, including inactivating hydrolysis by any aspartic protease or any other hydrolase activity present in the sample. Such reporter enzymes include, but are not limited to, the following: peroxidases, phosphatases, oxidoreductases, dehydrogenases, transferases, isomerases, kinases, reductases, deaminases, catalases, urease and glucuronidase. The selection of an appropriate reporter or marker enzyme will be readily apparent to those skilled in the art. In this method of the present invention, the preferred reporter enzymes are the peroxidases. In particular, horseradish peroxidase is the presently preferred reporter enzyme because horseradish peroxidase is not readily hydrolyzed by aspartic protease or many other well-known proteases which may be present in the sample.

The reporter enzyme is immobilized on a solid support, i.e., an insoluble matrix, gel or resin, in such a manner whereby the reporter enzyme is released upon action of aspartic protease. Solid supports in accordance with the present invention include, but are not limited to, the following: cellulose, agarose, dextran, polyacrylate, polyacrylamide, or their derivatives, chitin, sepharose, oxirane acrylic beads, polymeric dialdehyde, starch, collagen, keratin, elastin, bovine hide powder, bacterial cell wall peptidoglycan or fragments thereof, nylon, polyethylene terephthalates, polycarbonates, and controlled pore glass. Presently preferred solid supports in this method of the claimed invention include chitin, polyacrylate, cellulose, and their derivatives, and sepharose. Immobilization of the reporter enzyme on the solid support is carried out using conventional methods and procedures known to and understood by those skilled in the art.

The reporter enzyme can be immobilized on the solid support through the use of a linker molecule which is a hydrolyzable substrate for the enzymatically active aspartic protease. In this method of the present invention, such linker molecules include proteins and peptides, with proteins being the preferred linker molecules. If the linker molecule is a protein, preferred proteins include, but are not limited to, the following: azocasein, casein, κ-casein, immunoglobulins, hemoglobin, myoglobin, albumin, elastin, keratin and collagen. In preferred embodiments of this method of the claimed invention, the linker molecule is κ-casein, casein, hemoglobin, or myoglobin.

The indicator can be any chemical species which undergoes a detectable change as a result of the reaction or as a result of the culmination of reactions occurring when enzymatically active aspartic protease is present in the sample or specimen. The resulting detectable change is an indication of the presence of enzymatically active aspartic protease in the sample and, in turn, the presence of enzymatically active aspartic protease in the sample indicates the presence of candidiasis.

Preferred indicators are visual indicators and, in particular, chromogenic indicators, i.e., those in which the detectable change is a change in color, including the formation of color in an otherwise colorless material, upon action of the reporter or marker enzyme when it is released from the solid support by enzymatically active aspartic protease. Alternatively, the reporter enzyme may be capable of catalyzing the formation of a fluorescent signal, a phosphorescent signal, a bioluminescent signal, a chemiluminescent signal, or an electrochemical signal upon its release from the solid support by the action of aspartic protease. Additionally, the reporter enzyme may be capable of producing other visible or detectable signals, such as, for example, a clot, an agglutination, a precipitation, or a clearing zone. In these cases, the indicator would be the chemical species or substrate required by the reporter enzyme in order to bring about the desired detectable change.

A wide variety of chromogenic indicators (i.e., chromogens) and other species having a similar effect may be used as visual indicators when peroxidases are used as the reporter or marker enzymes. Preferred chromogenic indicators in accordance with the present invention comprise a hydroperoxide and a chromogen including, but not limited to, one of the following: guaiac, 2-2'-azino-bis(3-ethylbenthiazoline-6-sulfonic acid), tetramethylbenzidine, phenol, 4-aminoantipyrine, and 4,5-dihydroxynaphthalene-2,7-disulfonic acid. A particularly preferred chromogenic indicator is comprised of a hydroperoxide and guaiac, a chromogen which is colorless in its reduced state and deep blue in its oxidized state. Optionally, the guaiac may be purified prior to use, e.g., by solvent extraction. The most appropriate chromogenic indicator for any given reporter enzyme will depend on the reaction or reactions which the reporter enzyme is capable of catalyzing or initiating, and the selection in any given case will be readily apparent to those skilled in the art. As previously described, if the visual indicator is a chromogenic indicator, it is possible to employ either a liquid chromogen system or a solid chromogen system.

In yet another aspect of the present invention, a method is provided for detecting *Trichomonas vaginalis* by assaying for the presence of enzymatically active thiol protease in a sample, this method comprising: (a) contacting the sample with a solid support, the solid support having a reporter enzyme immobilized thereon in such a manner whereby the reporter enzyme is released upon action of the enzymatically active thiol protease; (b) combining the sample after having been contacted with the solid support with an indicator, the indicator being one which is susceptible to a detectable change upon action of the reporter enzyme; and (c) observing whether the indicator undergoes a detectable change, the detectable change being an indication of the presence of enzymatically active thiol protease in the sample and thus, *Trichomonas vaginalis*.

As with the previously described methods, the reporter enzyme or marker enzyme used in this method of the present invention can be any signal generating enzyme, i.e., an enzyme whose activity brings about a visible or detectable change, not subject to inactivation by any agent in the sample, including inactivating hydrolysis by any hydrolase activity present in the sample. Such reporter enzymes include, but are not limited to, the following: peroxidases, phosphatases, oxidoreductases, dehydrogenases, transferases, isomerases, kinases, reductases, deaminases, catalases, urease and glucuronidase. The selection of an appropriate reporter or marker enzyme will be readily apparent to those skilled in the art. In this method of the present invention, the preferred reporter enzymes are the peroxidases and, in particular, horseradish peroxidase.

The reporter enzyme is immobilized on a solid support, i.e., an insoluble matrix, gel or resin, in such a manner whereby the reporter enzyme is released from the solid support upon action of the enzymatically active thiol protease. Solid supports in accordance with the present invention include, but are not limited to, the following: cellulose, agarose, dextran, polyacrylate, polyacrylamide, or their derivatives, chitin, sepharose, oxirane acrylic beads, polymeric dialdehyde, starch, collagen, keratin, elastin, bovine hide powder, bacterial cell wall peptidoglycan or fragments thereof, nylon, polyethylene terephthalates, polycarbonates, and controlled pore glass. Presently preferred solid supports in this method of the claimed invention include chitin, polyacrylate, cellulose, and their derivatives, and sepharose. Immobilization of the reporter enzyme on the solid support is carried out using conventional methods and procedures known to and understood by those skilled in the art.

The reporter enzyme can be immobilized on the solid support through the use of a linker molecule which is a hydrolyzable substrate for the enzymatically active thiol protease. In this method of the present invention, such linker molecules include proteins and peptides, with proteins being the preferred linker molecules. If the linker molecule is a protein, preferred proteins include, but are not limited to, the following: azocasein, casein, κ-casein, immunoglobulins, hemoglobin, myoglobin, albumin, elastin, keratin and collagen. In preferred embodiments of this method of the claimed invention, the linker molecule is κ-casein, casein, hemoglobin, or myoglobin.

The indicator can be any chemical species which undergoes a detectable change as a result of the reaction or as a result of the culmination of reactions occurring when enzymatically active thiol protease is present in the sample or specimen. The resulting detectable change is an indication of the presence of enzymatically active thiol protease in the sample and, in trrn, the presence of enzymatically active thiol protease in the sample indicates the presence of *Trichomonas vaginalis*.

Preferred indicators are visual indicators and, in particular, chromogenic indicators, i.e., those in which the detectable change is a change in color, including the formation of color in an otherwise colorless material, upon action of the reporter or marker enzyme when it is released from the solid support by the enzymatically active aspartic protease. Alternatively, the reporter enzyme may be capable of catalyzing the formation of a fluorescent signal, a phosphorescent signal, a bioluminescent signal, a chemiluminescent signal, or an electrochemical signal upon its release from the solid support by the action of aspartic protease. Additionally, the reporter enzyme may be capable of producing other visible or detectable signals, such as, for example, a clot, an agglutination, a precipitation, or a clearing zone. In these cases, the indicator would be the chemical species or substrate required by the reporter enzyme in order to bring about the desired detectable change.

A wide variety of chromogenic indicators (i.e., chromogens) and other species having a similar effect may be used as visual indicators when peroxidases are used as the reporter or marker enzymes. Preferred chromogenic indicators in accordance with the present invention comprise a hydroperoxide and a chromogen including, but not limited to, one of the following: guaiac, 2-2'-azino-bis(3-ethyl-benthiazoline-6-sulfonic acid), tetramethylbenzidine, phenol, 4-aminoantipyrine, and 4,5-dihydroxynaphthalene-2,7-disulfonic acid. A particularly preferred chromogenic indicator is comprised of a hydroperoxide and guaiac, a chromogen which is colorless in its reduced state and deep blue in its oxidized state. The most appropriate chromogenic indicator for any given reporter enzyme will depend on the reaction or reactions which the reporter enzyme is capable of catalyzing or initiating, and the selection in any given case will be readily apparent to those skilled in the art. As previously described, if the visual indicator is a chromogenic indicator, it is possible to employ either a liquid chromogen system or a solid chromogen system.

As with the aspartic protease assays, certain reaction conditions and specific inhibitors can used to increase thiol protease activity and specificity. For example, one could add inhibitors (such as, for example, pepstatin to inhibit aspartic proteases, soybean trypsin inhibitor to inhibit trypsin, EDTA or other chelators to inhibit metallo-proteases, or any of the many known naturally occurring inhibitors of non-thiol protein proteases) to the test system so that only thiol proteases would function and thus, be detected. Additionally, by assaying at a pH of about 7.4, many thiol proteases will be active, but aspartic proteases will be inactivated.

It is important to note that the reporter enzyme release technology of the present invention can also be employed to detect the presence or absence of a hydrolase inhibitor in a sample. Many biological processes, including regulation of blood pressure, blood clotting, bacterial replication, etc., involve the use of very specific, carefully modulated hydrolases. Moreover, numerous drugs, pesticides and herbicides, etc., are known to function by virtue of inhibiting specific hydrolases. Under certain circumstances, it is highly desirable to determine the blood concentration of a hydrolase-inhibiting therapeutic drug or to determine the presence of a potential pesticide hydrolase inhibitor contamination in produce, etc. In these cases, it is, therefore, necessary to detect the inhibitor of a hydrolase, rather than the hydrolase itself.

Accordingly, in another aspect of the present invention, a method for assaying for the presence of an inhibitor of a target hydrolase in a sample is provided, the method comprising: (a) contacting the sample with the target hydrolase and a solid support, the solid support having a reporter enzyme immobilized thereon in such a manner whereby the reporter enzyme is released upon action of the target hydrolase if the target hydrolase is not inactivated by the presence of the inhibitor; (b) combining the sample after having been contacted with the target hydrolase and the solid support with an indicator, the indicator being one which is susceptible to a detectable change upon action of the reporter enzyme; and (c) observing whether the indicator undergoes a detectable change, the detectable change being an indication of the absence of the inhibitor of the target hydrolase in the sample.

To detect the presence of a hydrolase inhibitor in a sample, a defmed quantity of the target hydrolase is incorporated into the test system, and test performance involves detecting the ability of the sample to inhibit the target hydrolase. In the event that the target hydrolase inhibitor is not present in the sample, the target hydrolase will release the reporter enzyme from the solid support, thereby producing a detectable change in the indicator. Conversely, if the target hydrolase inhibitor is present in the sample, the target hydrolase will be inhibited, the reporter enzyme will not be released from the solid support, and a detectable change or response will not be produced in the indicator. It is not essential that the inhibitor in the sample completely inhibit the target hydrolase added to the test system. It is only required that a sufficient amount of target hydrolase inhibition occurs to produce a noticeable difference in the anticipated detectable response.

This method of the present invention can be used to assay for the presence or absence of any known iffhibitor of a hydrolytic enzyme, including, but not limited to, the following: inhibitors of the proteases or (interchangeably) proteinases, peptidases, lipases, nucleases, homo- or hetero-oligosaccharidases, homo- or hetero-polysaccharidases, phosphatases, sulfatases, neuraminidases and esterases. In a preferred embodiment, this method is used to assay for the presence protease inhibitors, including, but not limited to, the following: aspartic protease inhibitors, serine protease inhibitors, thiol protease inhibitors, metallo protease inhibitors, acid protease inhibitors and alkaline protease inhibitors. In a further preferred embodiment, this method is used to assay for the presence of aspartic protease inhibitors such as, for example, pepstatin, ovomacroglobulin, haloperidol, transition state mimetics, U-81749, H-261, MV7-101, A-75925, A-76928 and A-7003. U-81749, H-261, MV7-101, A-75925, A-76928 and A-7003 are experimental drugs which have previously been described in the literature. In an even further preferred embodiment of this method of the present invention, pepstatin is the aspartic protease inhibitor whose presence is being detected.

In accordance with this method of the present invention, target hydrolases include, but are not limited to, the following: proteases, proteinases, peptidases, lipases, nucleases, homo- or hetero-oligosaccharidases, homo- or hetero-polysaccharidases, phosphatases, sulfatases, neuraminidases and esterases. The particular target hydrolase used in the above method will depend upon which inhibitor is being detected, and the selection in any given case will be readily apparent to those skilled in the art. If, for example, pepstatin is the inhibitor being detected, then aspartic protease would be the target hydrolase used in the test system described above.

The reporter enzyme or marker enzyme used in this method of the present invention can be any signal generating enzyme, i.e., an enzyme whose activity brings about a visible or detectable change, not subject to inactivation by any agent in the sample, including inactivating hydrolysis by the target hydrolase which is incorporated into the test system. Such reporter enzymes include, but are not limited to, the following: peroxidases, phosphatases, oxidoreductases, dehydrogenases, transferases, isomerases, kinases, reductases, deaminases, catalases, urease and glucuronidase. The selection of an appropriate reporter or marker enzyme will be readily apparent to those skilled in the art. In this method of the present invention, the preferred reporter enzymes are the peroxidases, and, in particular, horseradish peroxidase.

The reporter enzyme is immobilized on a solid support, i.e., an insoluble matrix, gel or resin, in such a manner whereby the reporter enzyme is released from the solid support upon action of the target hydrolase if the target hydrolase is not inactivated by the presence of the inhibitor. Solid supports in accordance with the present invention include, but are not limited to, the following: cellulose, agarose, dextran, polyacrylate, polyacrylamide, or their derivatives, chitin, sepharose, oxirane acrylic beads, polymeric dialdehyde, starch, collagen, keratin, elastin, bovine hide powder, bacterial cell wall peptidoglycan or fragments thereof, nylon, polyethylene terephthalates, polycarbonates, and controlled pore glass.

The reporter enzyme can be immobilized on the solid support through the use of a linker molecule which is a hydrolyzable substrate for the enzymatically active target hydrolase. Such linker molecules include, but are not limited to, the following: proteins, carbohydrates, lipids, peptides, esters and nucleic acids. The particular linker molecule used to attach the reporter enzyme to the solid support will depend on which target hydrolase is added to the test system, and the selection in any given case will be readily apparent to those skilled in the art.

The indicator can be any chemical species which undergoes a detectable change as a result of the reaction or as a result of the culmination of reactions occurring if the enzymatically active target hydrolase is not inactivated by the presence of the inhibitor in the sample or specimen. Preferred indicators are visual indicators and, in particular, chromogenic indicators, i.e., those in which the visible change is a change in color, including the formation of color in an otherwise colorless material, upon action of the reporter or marker enzyme when it is released from the solid support by the enzymatically active target hydrolase provided it is not inactivated by the presence of the inhibitor in the sample or specimen.

A wide variety of chromogenic indicators (i.e., chromogens) and other species having a similar effect may be used as visual indicators. Preferred chromogenic indicators for peroxidase-like reporter enzymes in accordance with the present invention comprise a hydroperoxide and a chromogen including, but not limited to, one of the following: guaiac, 2-2'-azino-bis(3-ethyl-benthiazoline-6-sulfonic acid), tetramethylbenzidine, phenol, 4-aminoantipyrine, and 4,5-dihydroxynaphthalene- 2,7-disulfonic acid. A particularly preferred chromogenic indicator is comprised of a hydroperoxide and guaiac, a chromogen which is colorless in its reduced state and deep blue in its oxidized state. As previously described, if the visual indicator is a chromogenic indicator, it is possible to employ either a liquid chromogen system or a solid chromogen system.

In yet another aspect of the present invention, a test device for assaying for the presence of an enzymatically active hydrolase in a sample is provided, the test device comprising: a receptacle defined at least in part by first and second opposing walls having interior-facing surfaces with a gap therebetween, the first, second, or both walls being of light-transmitting material; a reporter enzyme immobilized on a solid support on the interior-facing surface of one of the first and second walls in such a manner whereby the reporter enzyme is released upon action of the hydrolase; an indicator contained on the interior-facing surface of one of the first and second walls, the indicator being one which is susceptible to a detectable change upon action of the reporter enzyme; and an opening in the receptacle for introduction of the sample.

In accordance with this aspect of the present invention, the receptacle is preferably flat and thin and of a size which can be easily held by hand. Accordingly, the chamber is preferably flat and shallow as well, with a width and length much greater than its depth, the depth being substantially constant. The chamber is preferably shallow enough to promote spontaneous wetting of the chamber walls with the specimen to achieve the maximum contact between the specimen and the dry reagent coatings on the upper and lower surfaces. This is of particular interest when reagent coatings are present on both the upper and lower surfaces of the chamber. In such cases, a small constant distance between these surfaces will also miniize the distance over which the reagents on the surface opposite that to which the visual indicator has been applied will need to diffuse in order to reach the indicator.

Within these considerations, the chamber depth is not critical to the invention and may vary. In most cases, a chamber ranging from about 3 mil to about 50 mil (0.003–0.050 inch; 0.0076–0.127 cm) in depth, preferably from about 5 mil to about 15 mil (0.005–0.0.015 inch; 0.0127–0.0381 cm), will give the best results. For any given depth, the lateral dimensions of the chamber (i.e., the spacing between its side walls) will defme the size of the sample which the device will accommodate, and are otherwise unimportant except to define the size and shape of the visible test area on the outer surface of the device. The lateral dimensions should thus provide a test area which is large enough to be seen, and yet small enough that the chamber which will be completely filled by a specimen of reasonable size. The specimen size will vary with the type of specimen and its source and method of sampling. In typical structures, it is contemplated that the lateral area of the chamber will range from about 0.1 $cm^2$ to about 10 $cm^2$, or preferably from about 0.3 $cm^2$ to about 3 $cm^2$. The internal volume of the chamber in typical structures will likewise vary, and for most tppes of samples, volumes ranging from about 3 $\mu L$ to about 300 $\mu L$ will be the most appropriate and convenient.

The test device of the present invention can be used to assay for the presence of any known hydrolytic enzyme including, but not limited to, the following: proteases or (interchangeably) proteinases, peptidases, lipases, nucleases, homo- or hetero-oligosaccharidases, homo- or hetero-polysaccharidases, phosphatases, sulfatases, neuraminidases and esterases. In a preferred embodiment, the test device of the present invention can be used to assay for the presence of proteases, including, but not limited to, the following: aspartic proteases, serine proteases, thiol proteases, metallo proteases, and acid or alkaline proteases. In another preferred embodiment, the test device of the present invention can be used to assay for the presence of homo- or hetero-oligosaccharidases or homo- or hetero-polysaccharidases, including, but not limited to, chitinase, cellulase, amylase and lysozyme.

The reporter enzyme or marker enzyme used in the test device can be any signal generating enzyme, i.e., an enzyme whose activity brings about a detectable change, not subject to inactivation by any agent in the sample, including inactivating hydrolysis by any hydrolase activity present in the sample. Such reporter enzymes include, but are not limited to, the following: peroxidases, phosphatases, oxidoreductases, dehydrogenases, transferases, isomerases, kinases, reductases, deaminases, catalases, urease and glucuronidase. The selection of an appropriate reporter or marker enzyme will be readily apparent to those skilled in the art. Presently preferred reporter enzymes are the peroxidases, such as, for example, horseradish peroxidase.

The reporter enzyme is immobilized on a first solid support, i.e., an insoluble matrix, gel or resin, in such a manner whereby the reporter enzyme is released from the solid support upon action of the hydrolase whose presence is being detected. Preferred solid supports in accordance with the present invention include, but are not limited to, the following: cellulose, agarose, dextran, polyacrylate, polyacrylamide, or their derivatives, chitin, sepharose, oxirane acrylic beads, polymeric dialdehyde, starch, collagen, keratin, elastin, bovine hide powder, bacterial cell wall peptidoglycan or fragments thereof, nylon, polyethylene terephthalates, polycarbonates, and controlled pore glass. Immobilization of the reporter enzyme on the first solid support is carried out using conventional methods and procedures known to and understood by those skilled in the art.

The reporter enzyme can be attached directly to the first solid support or, alternatively, the reporter enzyme can be immobilized on the first solid support through the use of a linker molecule having a hydrolyzable linkage which is a substrate for the enzymatically active hydrolase being detected. Such linker molecules include, but are not limited to, the following: proteins, carbohydrates, lipids, peptides, esters and nucleic acids. The particular linker molecule used to attach the reporter enzyme to the first solid support will depend on which hydrolase is being detected, and the selection in any given case will be readily apparent to those skilled in the art.

In the test device of the present invention, the indicator is immobilized on a second solid support which is not in contact with the first solid support. Preferred solid supports in accordance with the present invention include, but are not limited to, the following: cellulose, agarose, dextran, polyacrylate, or their derivatives, chitin, sepharose, oxirane acrylic beads, polymeric dialdehyde, starch, collagen, keratin, elastin, bovine hide powder, bacterial cell wall peptidoglycan, or fragments thereof, polyacrylamide, nylon, polyethylene terephthalates, polycarbonates, and controlled pore glass. Immobilization of the indicator on the second solid support is carried out using conventional methods and procedures known to those skilled in the art.

The indicator can be any chemical species which undergoes a detectable change as a result of the reaction or as a result of the culmination of reactions occurring when the enzymatically active hydrolase is present in the sample or specimen. This detectable change is, therefore, an indication that the enzymatically active hydrolase being assayed is present in the sample or specimen. Preferred indicators are visual indicators and, in particular, chromogenic indicators, i.e., those in which the visible change is a change in color, including the formation of color in an otherwise colorless material, upon action of the reporter or marker enzyme when it is released from the solid support by the hydrolase whose presence is being detected. Alternatively, the reporter enzyme may be capable of catalyzing the formation of a fluorescent signal, a phosphorescent signal, a bioluminescent signal, a chemiluminescent signal, or an electrochemical signal upon its release from the solid support by the action of the hydrolase. Additionally, the reporter enzyme may be capable of producing other visible or detectable signals, such as, for example, a clot, an agglutination, a precipitation, or a clearing zone. In these cases, the indicator would be the chemical species or substrate required by the reporter or marker enzyme in order to bring about the desired detectable change.

A wide variety of chromogenic indicators (i.e., chromogens) and other species having a similar effect may be used as visual indicators. When peroxidases are used as reporter or marker enzymes, preferred chromogenic indicators comprise a hydroperoxide and a chromogen including, but not limited to, one of the following: guaiac, 2-2'-azino-bis(3-ethyl-benthiazoline-6-sulfonic acid), tetramethylbenzidine, phenol, 4-aminoantipyrine, and 4,5-dihydroxynaphthalene-2,7-disulfonic acid. A particularly preferred chromogenic indicator is comprised of a hydroperoxide and guaiac, a chromogen which is colorless in its reduced state and deep blue in its oxidized state. Optionally, the guaiac may be purified prior to use, e.g., by solvent extraction. The most appropriate chromogenic indicator for any given reporter enzyme will depend on the reaction or reactions which the reporter enzyme is capable of catalyzing or initiating, and the selection in any given case will be readily apparent to those skilled in the art.

If the visual indicator is a chromogenic indicator, a solid chromogen system is employed. This solid chromogen system comprises a hydroperoxide, a chromogen capable of being oxidized by hydroperoxides in the presence of a peroxidase, and a solid support onto which the chromogen has been impregnated or immobilized and dried. In this system, the chromogen can be impregnated onto a bibulous paper or support as is done with Hemoccult® slides or, alternatively, the chromogen can be deposited onto a plastic or other sheet in the form of a thin layer. In this latter format, the chromogen could be layered as a solution containing a polymeric material (such as, for example, hydroxypropyl cellulose, ethyl cellulose, etc.). If the chromogen itself is a water soluble chromogen, it can be trapped in a matrix of material which is insoluble in water. Alternatively, if the chromogen itself is insoluble in water, it can be layered as a solution in an organic solvent either alone or in combination with a water soluble or water insoluble polymer.

In this particular chromogen system, the hydroperoxide can be provided either in a solid form (such as, for example, titanium hydroperoxide) or it can be generated in situ in the device. Hydrogen peroxide, for example, can be generated in situ by layering dried glucose and glucose oxidase on the interior-facing surfaces of the test device. Alternatively, hydrogen peroxide can be generated in situ by layering a suspension of sodium perborate in alcohol on the interior-facing surfaces of the test device. At low pH, sodium perborate releases hydrogen peroxide spontaneously. In the presence of the hydrogen peroxide and the peroxidase (e.g., horseradish peroxidase) upon its release from the first solid support by the hydrolase, the chromogen will be oxidized and a visually detectable change in color will result. As previously mentioned, this resulting change in color is an indication that the enzymatically active hydrolase is present in the sample or specimen.

It will be readily apparent to those skilled in the art that the reactions conditions (such as, for example, the selection of the solid support and linker molecule, pH, buffer capacity, buffer identity, salts, etc.) of the presently claimed test device can be modified and regulated to increase hydrolase activity and specificity, and to differentiate between the different hydrolases which may be present in a sample. Additionally, it will be readily apparent to the skilled artisan that specific enzyme inhibitors can be added to the presently claimed test devices to increase hydrolase activity and specificity, and to differentiate between the different hydrolases in a sample.

The test device is provided with a sample introduction port by which the specimen is placed in the chamber. The port is preferably in the same wall through which changes in the visual indicator are observed, i.e., the light-transmitting wall. The port will be shaped to accommodate the transfer device which is used to convey the sample from its source, and the port may thus be varied to suit any of the various types of transfer devices which might be used. Examples of transfer devices are syringes, pipettes, swabs and specula. Others will readily occur to those skilled in the art. A circular port is generally adequate, although for transfer devices such as swabs, the port may contain a straight edge along which the transfer device can be scraped to more easily release the specimen.

Preferred embodiments of the test device contain additional features which further promote the fluid migration needed to fill the chamber and thereby place all reagents in contact with the specimen. One such feature is the inclusion of one or more vent holes in the chamber to permit the escape of air. The vent holes will be adequately distanced from the sample introduction port to maximize the surface area wetted by the specimen. In devices where specimen-activated positive and negative controls are included inside the chamber in positions horizontally adjacent to the test area, the vent holes will be arranged to assure that the specimen reaches both controls and fills them to avoid any false or ambiguous readings. As discussed below, one preferred arrangement of the device is the placement of the test area between the control areas such that the positive and negative control areas do not share a common boundary although each does share a common boundary with the test area. In this arrangement, the sample introduction port is most conveniently placed at a location in the wall directly above the test area, and one vent hole is placed above each of the two control areas at or near the outer extremities of these areas, thereby causing the specimen to fill first the test area and then both control areas.

Another feature promoting fluid migration in preferred embodiments of the invention is the placement of a surface-active agent along the interior surface of the chamber. The agent may be along one or the other of the upper and lower surfaces of the chamber, preferably both, and may be included as a dry solute in a support matrix comprising the innermost lamina or coating on the surface. In some cases, the lamina will also contain one or more reagents taking part in the test reactions. In other cases, the surface-active agent will be the sole functional component of the lamina.

Surface-active agents will be useful for specimens which are water-based, as most biological specimens are. Suitable surface-active agents will be those which can be rendered in solid form, and a wide variety of substances which have a surface-active effect may be used. The substances will generally be detergents, wetting agents or emulsifiers, and will vary widely in chemical structure and electronic character, including anionic, cationic, zwitterionic and non-ionic substances. Examples are alkyl-alkoxy sulfates, alkyl aryl sulfonates, glycerol fatty acid esters, lanolin-based derivatives, polyoxyethylene alkyl phenols, polyoxyethylene amines, polyoxyethylene fatty acids and esters, polyoxyethylene fatty alcohols and ethers, poly(ethylene glycol) fatty acids and esters, polyoxyethylene fatty esters and oils, polyoxypropylene/polyoxyethylene condensates and block polymers, sorbitan fatty acid esters, sulfo derivatives of succinates, alkyl glucosides, and cholic acid derivatives. Trade names of products falling within some of these classes are Lubrol, Brij, Tween, Tergitol, Igepal, Triton, Teepol and many others.

Formation of the solid laminae, both indicator and reagent laminae, may be done by applying the lamina material in liquid form followed by drying or other solidification. The liquid form of the substance may be, for example, a solution, a suspension, or an uncured liquid state of the substance, and the solidification step may thus be an evaporation of the solvent or a curing of the substance. The substance of interest may be combined with additional materials for any of a variety of purposes, such as for example:

(1) to facilitate the application of the liquid to the surface by modifying the viscosity of the liquid, (2) to help form a continuous smooth solid layer which remains uniform and does not disintegrate or granulate over time or upon the application of additional layers over it, (3) to modify the solubility of the layer with solvents used in layers to be applied over it or to make the layer soluble in solvents which do not dissolve layers applied underneath, or all of these at the same time. Soluble polymeric materials are preferred additives to serve one or all of these purposes. Examples are cellulose and various cellulose derivatives, with the substitutions appropriately selected to achieve the desired solubility characteristics. For those test devices designed for aqueous or other water-based samples, the indicator lamina preferably contains the indicator retained in a matrix of solid material which is insoluble in water. This prevents the indicator from migrating out of the lamina and away from the light-transmitting surface. Alternatively, however, the indicator itself is insoluble in water and will by itself form a coherent lamina which will remain intact.

For those embodiments of the invention in which a positive control indicator, a negative control indicator or both are included in the device, one or more additional reagents will be included for each control. These additional reagents will either be incorporated within one of the existing laminae in a horizontally defined portion of that lamina or applied as a separate, vertically adjacent lamina over a horizontally defined portion of the existing lamina. By virtue of their position in the chamber, therefore, these additional reagents define control areas which are horizontally separated from each other and from the test area.

The selection of an appropriate reagent for a positive or negative control will depend on the hydrolase toward which the overall test is directed, the type of visual indicator used to detect the presence of the hydrolase, and whether the reagent is intended to serve as a positive control or a negative control. By utilizing known chemistries, the selection of an appropriate reagent will in most cases be apparent to those skilled in the art. The reagent for a positive control, for example, may be a sample of the hydrolase itself, an analogue of the hydrolase, or any other species with a parallel mode of action which initiates or induces the reaction or reaction sequence which culminates in a detectable change in the indicator. The lamina containing this reagent will be on either the upper or lower surface of the chamber provided that the reagent will not initiate or induce the detectable change until the specimen is present, but will do so independently of the presence or absence of the enzymatically active hydrolase in the specimen. The reagent for a negative control may likewise be an inhibiting species such as a denaturing, inhibiting or otherwise inactivating agent which prevents or blocks the reaction or reaction sequence, and thereby prevents the detectable change from occurring regardless of whether or not the enzymatically active hydrolase is present in the sample or specimen.

Both controls are activated when the specimen is applied to the test device. In some cases, this is achieved most effectively by placing the control reagents in laminae on the same surface as the lamina(e) containing the other reagent (s). In others, best results are achieved when the control reagents are placed in laminae on the chamber surface opposite that which bears the other reagent(s), such that the control reagent and the remaining reagent(s) are separated by the air gap. In preferred embodiments, the control areas of the device will contain all components and reagents used in the test area with the addition of the control reagents, either incorporated in horizontally delineated sections of one or more of the same laminae used in the test area or applied as separate laminae over such horizontally delineated sections. To achieve sharp boundaries for the control areas and to prevent the control reagents from activating or deactivating the test area, it is often beneficial to place discontinuities in the laminae at the boundaries separating the control areas from the test area to minimize or eliminate the possibility of lateral diffusion of the control reagents out of their respective control areas. These discontinuities may be in laminae along the upper surface, the lower surface, or both.

As indicated above, the controls are preferably activated by the same specimen sample used for the test. This is conveniently done by arranging the control areas as extensions of the test area, all contained in the same chamber in the test device, with unobstructed fluid communication between the various areas. In preferred embodiments where both positive and negative control areas are included, the control areas are isolated from each other by the test area which is positioned in between the two. Filling of all areas with a single application can be accomplished with the arrangement of the sample introduction port and vent holes described above. Since the detectable changes, or absence thereof, are detectable through the light-transmitting wall of the device, the identification of areas as positive and negative controls is conveniently achieved by placing appropriate indicia on the outer surface of the device.

The light-transmitting wall may be any material which is inert and sufficiently rigid to support the indicator lamina, and yet sufficiently transmissive of light to show the change in the indicator as soon as it occurs. Translucent or transparent materials, preferably nonabsorptive materials, may be used; transparent materials are preferred. Examples of transparent polymeric materials suitable for this use are polyethylene terephthalates (such as, for example, Mylar®) and polycarbonates (such as, for example, Lexan®). The opposing (i.e., bottom) wall of the device may likewise be made of transparent or translucent material, although it may also be of opaque material since visualization of the test results as well as the positive and negative controls is required only from one side of the device. When the bottom wall is transparent, detection of the change in the test area, control areas or both through the top wall can be enhanced by applying a printing or coating to either surface of the bottom wall with a colored or reflective material to heighten the color contrast.

The test device may be formed in a variety of ways. Sheets of polymeric material may be laminated together, with appropriate cutouts to define the shape of the chamber and holes for the sample introduction port and the vent holes. The depth of the chamber as well as its shape and lateral dimensions will then be defined by the thickness of the central sheet, while the placement of the holes will be controlled by the top sheet. The indicator and reagent coatings may be applied to the top sheet, bottom sheet or both, as required, before the sheets are assembled into the laminate. The sheets may then be secured together by any conventional means, such as, for example, by heat sealing or through the use of adhesives.

A particularly preferred method of forming the device is by the use of a single sheet of transparent or otherwise light-transmitting polymeric material, with a section of the sheet embossed or otherwise processed, mechanically or chemically, to contain a depression or indentation of constant depth in the inner surface of the chamber. The depression is located on one half of the sheet, with the holes for sample introduction and venting on the other half. The indicator and reagent coatings are applied at appropriate locations on the sheet, and the half containing the holes is then folded over the other half to form the enclosed chamber and to achieve correct alignment of the areas representing the upper and lower surfaces of the chamber. The facing surfaces of the sheet are bonded together as in the laminate of the preceding paragraph.

A preferred method for bonding the two halves together is through the use of a heat-sensitive, pressure-sensitive, water-based or solvent-based adhesive. The adhesive may be restricted to the areas peripheral to the chamber to avoid contact with the test reagents, or it may cover the entire surface of the sheet, having been applied prior to application of the indicator and reagent coatings. In the latter case, appropriate adhesives will be those which are transparent, inert, wettable by, and otherwise compatible with the layers to be applied over it. Many types of adhesives suitable for this application exist, and the most appropriate choice will vary from one system to the next depending on the layers to be applied above it.

In yet another aspect of the present invention, a test device for testing a sample for the presence of candidiasis by assaying for the presence of enzymatically active aspartic protease is provided, the test device comprising: a receptacle defined at least in part by first and second opposing walls having interior-facing surfaces with a gap therebetween, the first, second, or both walls being of light-transmitting material; a reporter enzyme immobilized on a solid support on the interior-facing surface of one of the first and second walls in such a manner whereby the reporter enzyme is released upon action of the aspartic protease; an indicator immobilized on the interior-facing surface of one of the first and second walls, the indicator being one which undergoes a detectable change upon action of the reporter enzyme; and an opening in the receptacle for introduction of the sample.

The reporter enzyme or marker enzyme used in this test device can be any signal generating enzyme not subject to inactivation by any agent in the sample, including hydrolysis by any aspartic protease activity or any other hydrolase activity present in the sample. Such reporter enzymes include, but are not limited to, the following: peroxidases, phosphatases, oxidoreductases, dehydrogenases, transferases, isomerases, kinases, reductases, deaminases, catalases, urease and glucuronidase. Presently preferred reporter enzymes are the peroxidases, such as, for example, horseradish peroxidase.

The reporter enzyme is immobilized on a first solid support, i.e., an insoluble matrix, gel or resin, in such a manner whereby the reporter enzyme is released upon action of aspartic protease. The reporter enzyme can be immobilized on the solid support through the use of a linker molecule having a hydrolyzable linkage which is a substrate for aspartic protease. In this test device, such linker molecules include proteins and peptides, with proteins being the preferred linker molecules. If the linker molecule is a protein, preferred proteins include, but are not limited to, the following: azocasein, casein, κ-casein, immunoglobulins, hemoglobin, myoglobin, albumin, elastin, keratin and collagen. In preferred embodiments of this test device, the linker molecule is κ-casein, casein, hemoglobin, or myoglobin.

In this test device of the present invention, the indicator is immobilized on a second solid support which is not in contact with the first solid support. Preferred solid supports in accordance with the present invention include, but are not limited to, the following: cellulose, agarose, dextran, polyacrylate, or their derivatives chitin, sepharose, oxirane acrylic beads, polymeric dialdehyde, starch, collagen, keratin, elastin, bovine hide powder, bacterial cell wall peptidoglycan or fragments thereof, polyacrylamide, nylon, polyethylene terephthalates, polycarbonates, and controlled pore glass. Immobilization of the indicator on the second solid support is carried out using conventional methods and procedures known by those skilled in the art.

The indicator can be any chemical species which undergoes a detectable change as the result of the reaction or as a result of the culmination of reactions occurring when the enzymatically active hydrolase is present in the sample or specimen. The resulting detectable change is an indication of the presence of enzymatically active aspartic protease in the sample and, in turn, the presence of enzymatically active aspartic protease in the sample indicates the presence of candidiasis. Preferred indicators are visual indicators and, in particular, chromogenic indicators, i.e., those in which the visible change is a change in color, including the formation of color in an otherwise colorless material, upon action of the reporter or marker enzyme when it is released from the solid support by the enzymatically active aspartic protease whose presence is being detected.

A wide variety of chromogenic indicators (i.e., chromogens) and other species having a similar effect may be used as visual indicators. Preferred chromogenic indicators in accordance with the present invention when peroxidase is the releasable reporter enzyme being used, comprise a hydroperoxide and a chromogen including, but not limited to, one of the following: guaiac, 2-2'-azino-bis(3-ethylbenthiazoline-6-sulfonic acid), tetramethylbenzidine, phenol, 4-aminoantipyrine, and 4,5-dihydroxynaphthalene-2,7-disulfonic acid. A particularly preferred chromogenic indicator is comprised of a hydroperoxide and guaiac, which is colorless in its reduced state and deep blue in its oxidized state.

If the visual indicator is a chromogenic indicator for peroxidases or pseudoperoxidases, a solid chromogen system is employed, and such a system comprises a hydroperoxide, a chromogen capable of being oxidized by hydroperoxides in the presence of a peroxidase, and a solid support onto which the chromogen has been impregnated or immobilized and dried. In this system, the chromogen can be impregnated onto a bibulous paper or support as is done with Hemoccult® slides or, alternatively, the chromogen can be deposited onto a plastic or other sheet in the form of a thin layer. In this latter format, the chromogen would be layered as a solution containing a polymeric material (such as, for example, hydroxypropyl cellulose, ethyl cellulose, etc.). If the chromogen itself is a water soluble chromogen, it can be trapped in a matrix of material which is insoluble in water. Alternatively, if the chromogen itself is insoluble in water, it can be layered as a solution in an organic solvent either alone or in combination with a water soluble or water insoluble polymer.

In this solid chromogen system, the hydroperoxide can be provided either in a solid form (such as, for example, titanium hydroperoxide) or it can be generated in situ in the test device. In the presence of the hydroperoxide and the peroxidase upon its release from the first solid support by the enzymatically active aspartic protease, the chromogen will be oxidized and a visually detectable change in color will result. As previously mentioned, this resulting change in color is an indication of the presence of enzymatically active aspartic protease in the sample or specimen and, in turn, the presence of enzymatically active aspartic protease indicates the presence of candidiasis.

In a final aspect of the present invention, a test device for testing a sample for the presence of an inhibitor of a target hydrolase is provided, the test device comprising: a receptacle defined at least in part by first and second opposing walls having interior-facing surfaces with a gap therebetween, the first wall, the second wall, or both being of light-transmitting material; a target hydrolase contained on the interior-facing surface of one of the first and second walls, the target hydrolase being susceptible to inactivation by the presence of the inhibitor; a reporter enzyme immobilized on a solid support on the interior-facing surface of one of the first and second walls in such a manner whereby the reporter enzyme is released upon action of the target hydrolase if the target hydrolase is not inactivated by the presence of the inhibitor; an indicator contained on the interior-facing surface of one of the first and second walls, the indicator being one which is susceptible to a detectable change upon action of the reporter enzyme; and an opening in the receptacle for introduction of the sample.

To detect the presence of a hydrolase inhibitor in a sample, a defined quantity of the target hydrolase is incorporated into the test device either immediately prior to performing the test, or, preferably, during the manufacture of the test device. Test performance involves detecting the ability of the sample to inhibit the target hydrolase. In the event that the target hydrolase inhibitor is not present in the sample, the target hydrolase will release the reporter enzyme from the solid support, thereby producing a detectable response in the indicator. Conversely, if the target hydrolase inhibitor is present in the sample, the target hydrolase will be inhibited, the reporter enzyme will not be released from the solid support, and a detectable change or response will not be produced in the indicator. It is not essential that the inhibitor in the sample completely inhibit the target hydrolase added to the test device. It is only required that a sufficient amount of target hydrolase inhibition occurs to produce a noticeable difference in the anticipated detectable response. The positive and negative control elements of the test device provide comparison responses to illustrate the appearances of completely inhibited target hydrolase and target hydrolase free of inhibition.

The sensitivity of this enzyme release technology can be adjusted as needed by incorporating defined quantities of the target hydrolase into the test device. Similarly, if desired, exposure time of the target hydrolase to any inhibitor in the sample can be regulated by physically or chemically separating the target hydrolase from the immobilized reporter enyyme. For example, by coating the immobilized reporter enzyme in a timed-release matrix, a pH degradable coating, or other controlled-release material which dissolves comparatively slowly, temporal access of the target hydrolase to the immobilized reporter enzyme can be controlled. Alternatively, the target hydrolase can be present in a location or chemical form which is immediately accessible to any inhibitor which may be present in the sample. Hence, prior to its gaining access to the immobilized reporter enzyme, the target hydrolase can first be exposed to the inhibitor for sufficient time for inhibition to take place. Since access to the immobilized reporter enzyme can be temporally regulated, the test results can detect the presence of even slowly acting inhibitors.

This test device of the present invention can be used to test a sample for the presence or absence of any known inhibitor of a hydrolytic enzyme, including, but not limited to, the following: inhibitors of the proteases or (interchangeably) proteinases, peptidases, lipases, nucleases, homo- or hetero-oligosaccharidases, homo- or hetero-polysaccharidases, phosphatases, sulfatases, neuraminidases and esterases. In a preferred embodiment, this test device is used to assay for the presence protease inhibitors, including, but not limited to, the following: aspartic protease inhibitors, serine protease inhibitors, thiol protease inhibitors, metallo protease inhibitors, acid protease inhibitors and alkaline protease inhibitors. In a further preferred embodiment, this test device is used to assay for the presence of aspartic protease inhibitors such as, for example, pepstatin, ovomacroglobulin, haloperidol, transition state mimetics, U-81749, H-261, MV7-101, A-75925, A-76928 and A-7003. U-81749, H-261, MV7-101, A-75925, A-76928 and A-7003 are experimental drugs which have previously been described in the literature. In an even further preferred embodiment of this test device of the present invention, pepstatin is the aspartic protease inhibitor whose presence is being detected.

In accordance with this test device of the present invention, target hydrolases include, but are not limited to, the following: proteases, proteinases, peptidases, lipases, nucleases, homo- or hetero-oligosaccharidases, homo- or hetero-polysaccharidases, phosphatases, sulfatases, neuraminidases and esterases. The particular target hydrolase used in this test device will depend upon which inhibitor is being detected, and the selection in any given case will be readily apparent to those skilled in the art. If, for example, pepstatin is the inhibitor being detected, then aspartic protease would be the target hydrolase used in the test device described above. Moreover, the appropriate concentrations of the target hydrolase, the geometric location of the target hydrolase in the test device, and the appropriate timed- and controlled-release technologies and matrices are known to those skilled in the art.

As with the other test devices presently claimed, the reporter enzyme or marker enzyme used in this particular test device can be any signal generating enzyme, i.e., an enzyme whose activity brings about a visible or detectable change, not subject to inactivation by any agent in the sample, including inactivating hydrolysis by the target hydrolase present in the test device. Such reporter enzymes include, but are not limited to, the following: peroxidases, phosphatases, oxidoreductases, dehydrogenases, transferases, isomerases, kinases, reductases, deaminases, catalases, urease and glucuronidase. The selection of an appropriate reporter or marker enzyme will be readily apparent to those skilled in the art. In this test device of the present invention, the preferred reporter enzymes are the peroxidases, and, in particular, horseradish peroxidase.

The reporter enzyme is immobilized on a solid support, i.e., an insoluble matrix, gel or resin, in such a manner whereby the reporter enzyme is released upon action of the target hydrolase if the target hydrolase is not inactivated by the presence of the inhibitor in the sample. Solid supports in accordance with the present invention include, but are not limited to, the following: cellulose, agarose, dextran, polyacrylate, polyacrylamide, or their derivatives, chitin, sepharose, oxirane acrylic beads, polymeric dialdehyde, starch, collagen, keratin, elastin, bovine hide powder, bacterial cell wall peptidoglycan or fragments thereof, nylon, polyethylene terephthalates, polycarbonates, and controlled pore glass.

As previously explained, the reporter enzyme can be immobilized on the solid support through the use of a linker molecule which is a hydrolyzable substrate for the enzymatically active target hydrolase. Such linker molecules include, but are not limited to, the following: proteins, carbohydrates, lipids, peptides, esters and nucleic acids. The particular linker molecule used to attach the reporter enzyme to the solid support will depend on which target hydrolase is incorporated in the test device, and the selection in any given case will be readily apparent to those skilled in the art.

The indicator can be any chemical species which undergoes a detectable change as a result of the reaction or as a result of the culmination of reactions occurring if the enzymatically active target hydrolase is not inactivated by the presence of the inhibitor in the sample or specimen. Preferred indicators are visual indicators and, in particular, chromogenic indicators, i.e., those in which the visible change is a change in color, including the formation of color in an otherwise colorless material, upon action of the reporter or marker enzyme when it is released from the solid support by the enzymatically active target hydrolase provided it is not inactivated by the presence of the inhibitor in the sample or specimen.

A wide variety of chromogenic indicators (i.e., chromogens) and other species having a similar effect may be used as visual indicators. Preferred chromogenic indicators for peroxidase-like reporter enzymes in accordance with the present invention comprise a hydroperoxide and a chromogen including, but not limited to, one of the following: guaiac, 2-2'-azino-bis(3-ethyl-benthiazoline-6-sulfonic acid), tetramethylbenzidine, phenol, 4-aminoantipyrine, and 4,5-dihydroxynaphthalene-2,7-disulfonic acid. A particularly preferred chromogenic indicator is comprised of a hydroperoxide and guaiac, a chromogen which is colorless in its reduced state and deep blue in its oxidized state. As previously described, if the visual indicator is a chromogenic indicator, it is possible to employ either a liquid chromogen system or a solid chromogen system.

It should be understood that the prior discussion pertaining to the structure of the test device for assaying for the presence of a hydrolase, its construction and its preferred embodiments is fully applicable to the test device for testing a sample for the presence of candidiasis by assaying for the presence of enzymatically active aspartic protease, and to the test device for testing a sample for the presence of an inhibitor of a target hydrolase.

While the invention is not intended to be limited to any particular construction of a test device, the attached Figures, which are not drawn to scale, illustrate how one such device may be constructed.

FIG. 1 depicts the support structure of the device in a perspective view, prior to the indicator and reagents being applied and the chamber being enclosed. The support structure consists of a single sheet 11 of relatively stiff, transparent, chemically inert plastic material, with a score line 12 defining a fold separating the sheet into two halves 13, 14, each having the same length and width. The lower half 13 contains an indentation of a composite shape consisting of a circle 15 at the center with two rectangular extensions 16, 17 extending to opposite sides. The upper half 14 contains three holes including a central hole 18 which serves as the sample introduction port, and two side holes 19, 20 which serve as vent holes. The two vent holes 19, 20 are circular, while the sample introduction port 18 is circular with one straight edge to facilitate scraping of the specimen from the swab which is used as a transfer device. The holes are positioned such that when the plastic is folded at the score line 12 and the top half 14 is placed in contact with the bottom half 13, the sample introduction port 18 is above the center of the circular part 15 of the indentation, and the vent holes 19, 20 are above the two rectangular extensions 16, 17 at the outermost edge of each. The two rectangular extensions 16, 17 represent the positive and negative control areas of the device.

Many variations of the device of FIG. 1 may be made. The two halves 13, 14 may be of differing lengths, widths or both for various reasons. The only critical feature is that the indentations in the lower half and the holes in the upper half be positioned relative to the score line such that the holes and indentations are in proper registration when the two halves are folded at the score line. As another example, the rectangular extensions 16, 17 in the lower half of the structure may terminate in circular (or half-circular) areas to match the vent holes 19, 20 in the top half. The vent holes themselves may be of any shape. In fact, vent holes which are shaped differently from the sample introduction hole 18 have the advantage of preventing user confusion as to where to introduce the sample.

Figure 2:
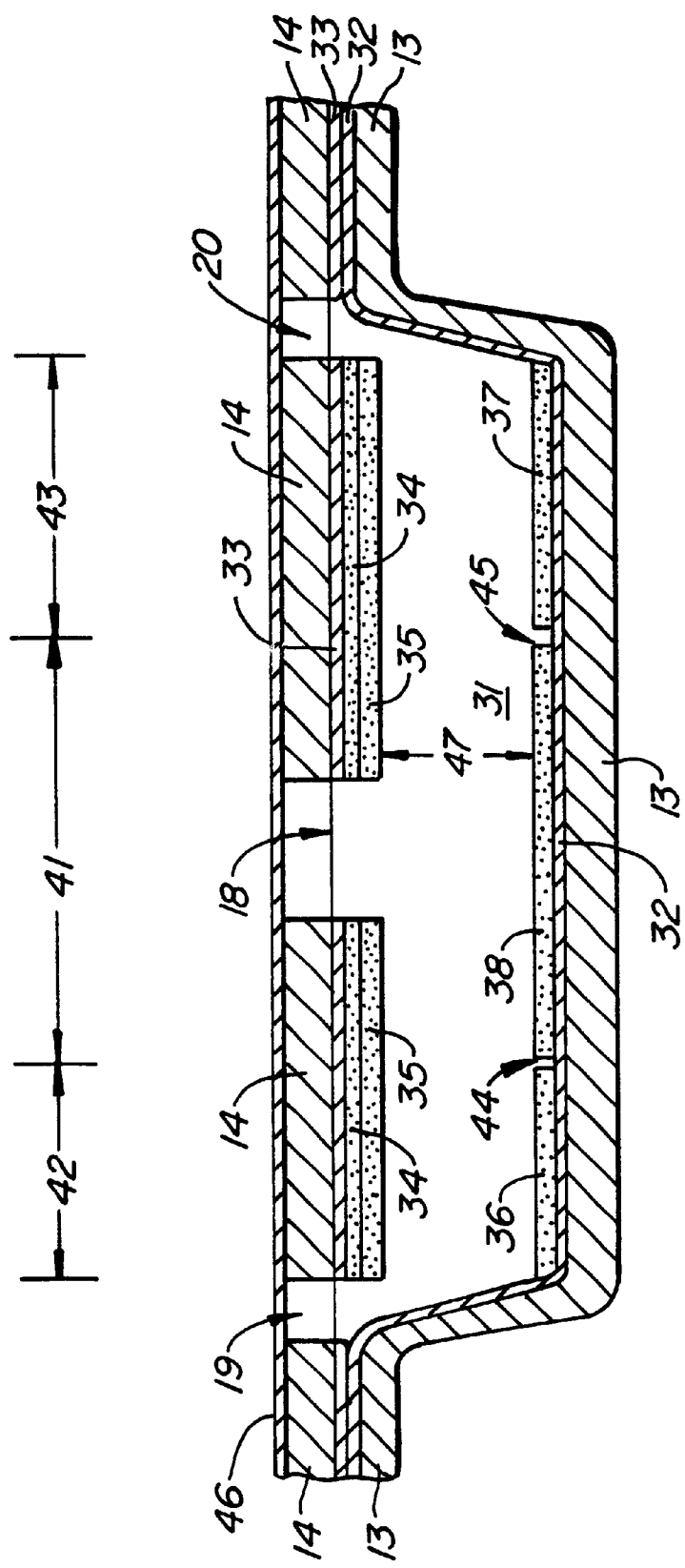
FIG. 2 is a side view in cutaway of a portion of the test device shown in FIG. 1.

FIG. 2 is a side cutaway view of the device of FIG. 1, showing the chamber 31 in cutaway after the coatings have been applied and the two halves folded over and sealed to one another. The inner surfaces of each of the two halves 13, 14 of the transparent polymer are coated with an adhesive 32, 33, respectively. Directly underneath the upper adhesive layer 33 is the layer containing the visual indicator 34, and beneath the latter is a layer of reagent 35. It will be noted that both the visual indicator layer 34 and the reagent layer 35 can extend the full length and width of the chamber, surrounding the sample introduction port 18 and extending into all areas of the chamber.

The test and control areas of the chamber are defined by the horizontal locations of the coatings on the lower wall 13 of the chamber. A reagent for the negative control is contained in one coating 36 which occupies the lower surface of one of the two rectangular extensions 16 of the chamber (see FIG. 1), and a reagent for the positive control is contained in a second coating 37 similarly situated in the other rectangular extension 17. Alternatively, reagents for the controls may be placed on the upper surface of the chamber rather than the lower. This is in fact preferred for certain assays. The portion of the lower surface under the central circular portion 15 of the chamber (see FIG. 1) is coated with a layer 38 which may either contain an additional reagent used in the test reaction or no reagent at all. Thus, as viewed from the top of the closed device, the circular test area 41 is flanked by a rectangular negative control area 42 and a rectangular positive control area 43. The three segments 36, 37, 38 can be separated by gaps or discontinuities 44, 45 to retard or minimize diffusion between, or contact of, the contents of these segments. Similar discontinuities may also be placed in either or both of the visual indicator and reagent layers 34, 35, directly above the discontinuities 44, 45 in the lower layer. The discontinuities in the visual indicator and reagent layers will further prevent diffusion of control components or other reagents from the control areas into the test area. The most inward-facing of the layers 35, 36, 37, 38 all may contain, in addition to any reagents present, a wetting agent or detergent to promote the rapid and complete spreading of the specimen along the upper and lower surfaces to fill the chamber. In some cases, the same effect is achieved by a layer of protein.

In certain embodiments of the invention, the reagents tend to deteriorate upon prolonged exposure to air or to air-borne moisture. In the device shown in FIG. 2, this is prevented by a thin sheet of material 46 which is both moisture-impermeable and air-impermeable. The sheet covers the sample injection port and both vent holes, sealing the chamber interior from the environment until the device is ready for use, whereupon the sheet is readily peeled off. For materials which are particularly water-sensitive or air-sensitive, it may also be desirable to place a moisture- and air-impermeable sheet on the bottom of the device, the sheet being either permanently attached or capable of being peeled off. Further protection against moisture and air can be achieved by placing the device in a pouch which completely surrounds the device.

As indicated above, each of the dimensions of the device shown in FIGS. 1 and 2 may vary, as may their arrangements and shapes. A typical example, however, is one in which the support sheet is Mylar 5 mil in thickness (0.005 inch, 0.0127 cm), and the adhesive layer is low density polyethylene 2 mil in thickness (0.002 inch, 0.0051 cm), the gap width 47 is 7.5 mil (0.0075 inch, 0.019 cm), the test area is a circle 5/16 inch in diameter (area: 0.0766 square inch, 0.494 cm$^2$), and the negative and positive control areas each measure 1/8 inch×1/16 inch (area: 0.0078 square inch, 0.0504 cm$^2$). The air vents in this example are each circular, and they and the sample introduction port are each 1/8 inch (0.32 cm) in diameter. The chamber volume is approximately 12 $\mu$L.

The test device of the present invention is useful for testing samples for the presence of a hydrolase from a wide range of sources, including biological sources and otherwise. Bodily fluids such as blood, serum, plasma, urine, urethral discharge, tears, vaginal fluid, cervical exudate, spinal fluid and saliva, as well as non-bodily fluids such as foods, pond or swimming pool water and liquid wastes are examples.

EXAMPLES

I. PREPARATIONS

A. PREPARATION OF CYANOGEN BROMIDE ACTIVATED SOLID SUPPORTS

1. MATERIALS
   a. Solid, insoluble supports (Sepharose 4B, chitin, and Sigmacell® 20 [purchased from Sigma Chemical Co.])
   b. Distilled water and ice made with distilled water
   c. 4.0 M NaOH
   d. Solid CNBr
   e. Coupling buffer (0.1 M NaHCO$_3$ containing 0.5 M NaCl)
   f. Magnetic stiring motor and stirring bar; pH meter; chemical fume hood

2. PROCEDURE

Ten milliliters (10 mL) of cold distilled water were added to 5 grams moist, washed solid support, and the mixture was chilled to 10° C.–15° C. The pH of the suspension was adjusted to 10.8 with 4.0 M NaOH, and 100 mg solid, crushed CNBr were added per gram moist solid support. The pH was maintained at 10.8 by adding 4.0 M NaOH as necessary, and the temperature of the suspension was allowed to increase to 18° C.–20° C. during the activation process. Activation was considered complete when no further additions of 4.0 M NaOH were needed to maintain pH at 10.8. At this time, crushed ice was added to cool the reaction mixture, and the suspension filtered on a pre-chilled sintered funnel. The filtrate was collected in a suction flask containing solid ferrous sulfate which inactivated residual CNBr and cyanide remaining in the reaction mixture. The solid support was washed with 1 liter cold distilled water and 1 liter coupling buffer under suction and stored as a moist paste at 4° C.

B. PREPARATION OF [KAPPA-CASEIN-HRPO] CONJUGATES (HYDRAZIDE METHOD)
1. MATERIALS
   a. Kappa-Casein and Horse Radish Peroxidase (HRPO) Hydrazide [purchased from Sigma Chemical Co.]
   b. Distilled water
   c. Buffers:
      i. 50 mM 2-[Morpholino] ethane sulfonic acid] (MES) buffer, pH 6.0
      ii. 100 mM Sodium acetate buffer, pH 4.0 containing 0.5 M NaCl
      iii. 100 mM Sodium borate, pH 9.0 containing 0.5 M NaCl
   d. Solid sodium periodate
   e. 100 mM Formaldehyde
2. PROCEDURE
   a. Periodate Activation of Kappa-Casein Twenty mg of Kappa-Casein were dissolved in 2 mL MES buffer and 8.6 mg solid sodium periodate were added to the solution. The mixture was incubated on a rotor for 30 minutes in the dark at room temperature. The reaction mixture was then dialyzed against approximately 300 mL 50 mM MES, pH 6.0 for approximately 45 minutes at room temperature, after which the dialysis fluid was replaced and dialysis continued for an additional 45 minutes.

b. Covalent Linking of HRPO to Kappa-Casein

Five mg HRPO hydrazide (approximately 175 Units/mg protein) were added to the activated, dialyzed Kappa-Casein, and the mixture incubated with agitation for 4 hours at room temperature. Two hundred microliters of 100 mM formaldehyde were added to the mixture, and incubation continued at room temperature for and additional 30 minutes. Two mL 1 M cold acetate buffer, pH 4.0 were added, and the conjugate allowed to precipitate for 30 minutes at 4° C. The pellet was removed by centrifugation, redissolved in 2 mL 100 mM borate buffer, pH 9.0, and stored at 4° C. until used.

C. ATTACHMENT OF [KAPPA-CASEIN-HRPO] CONJUGATES (HYDRAZIDE METHOD) TO CYANOGEN BROMIDE ACTIVATED SUPPORTS
1. MATERIALS
   a. [Kappa-Casein-HRPO] conjugates (PREPARATION B)
   b. Distilled water
   c. Buffers:
      i. Coupling Buffer (0.1 M NaHCO₃ containing 0.5 M NaCl)
      ii. 1.0 M Tris buffer, pH 8.0
      iii. 100 mM Sodium acetate buffer, pH 4.0 containing 0.5 M NaCl
      iv. 100 mM Sodium borate buffer, pH 9.0, containing 0.5 M NaCl
   d. Cyanogen bromide activated Sepharose 4B and Sigmacell® 20 (PREPARATION A)
   e. Cyanogen bromide activated Sepharose 6 MB (from Sigma Chemical Co.)
2. PROCEDURE
   a. Cyanogen Bromide Activated Sepharose 4B and Sigmacell® 20

Two milliliters [Kappa-Casein-HRPO] conjugate prepared from the hydrazide of HRPO as described in PREPARATION B were diluted with 3 mL coupling buffer and added to one gram moist cyanogen bromide-activated Sepharose 4B or Sigmacell®. The suspension was mixed end-over-end at room temperature for two hours. The solid support was washed with coupling buffer and water and 3 mL 1.0 M Tris buffer, pH 8 were added. The suspension was incubated for 2 hours at room temperature to inactivate remaining active sites on the solid support. Three washing cycles, each consisting of pH 4.0 acetate buffer followed by coupling buffer, were used to remove unbound materials from the support. A fmal wash with distilled water was used, and the moist suspension stored at 4° C. until used.

b. Commercially Activated Sepharose 6 MB (Sigma Chemical Co.)

The moist gel (1 gram moist weight) was washed with 200 mL 1 mM HCl prior to use as described above.

c. Activated Chitin

The procedure described in A above was employed, except that 500 mg of moist, activated chitin were used, instead of 1 gram.

D. PREPARATION OF HORSE RADISH PEROXIDASE (HRPO) ALDEHYDE
1. MATERIALS
   a. HRPO, Type II, 200 Units/mg (from Sigma Chemical Co.)
   b. 20 mM 2-(N-morpholino)ethanesulfonic acid (MES) buffer, pH 5.0
   c. Solid sodium periodate
   d. Biogel$^R$ P-30 spherical polyacrylamide gel purchased from Bio-Rad
2. PROCEDURE 25.7 mg solid sodium periodate (40 millimoles) were added to 30 mg HRPO in 3 mL MES buffer. The solution was incubated in the dark for 30 minutes at room temperature with continuous rotation. The solution was passed through a P-30 column in MES buffer to remove excess sodium periodate, and the colored HRPO collected in a total volume of 3 ml. The HRPO aldehyde was immediately coupled to the desired protein (hemoglobin, myoglobin, or casein).

E. ATTACHMENT OF HEMOGLOBIN AND MYOGLOBIN TO CYANOGEN BROMIDE ACTIVATED SOLID SUPPORTS
1. MATERIALS
   a. Solid, insoluble supports
      i. Cyanogen bromide activated sepharose 6MB (from Sigma Chemical Co.)
      ii. Sigmacell® 20 (as described in PREPARATION A)
   b. Distilled water
   c. Buffers:
      i. Coupling Buffer (0.1 M NaHCO₃ containing 0.5 M NaCl)
      ii. 1.0 M Tris buffer, pH 8.0
      iii. 100 mM Sodium acetate buffer, pH 4.0 containing 0.5 M NaCl
      iv. 100 mM Sodium borate buffer, pH 8.0 containing 0.5 M NaCl v. 0.1 Percent (v/v) glutaraldehyde solution in water

2. PROCEDURES

One hundred milligrams of either hemoglobin or myoglobin dissolved in 5 mL of coupling buffer were added to 1 gram moist solid support. The suspension was mixed end-over-end at room temperature for two hours. The solid support was washed with coupling buffer and water and 3 mL 1.0 M Tris buffer, pH 8 were added and the suspension incubated for 2 hours at room temperature to inactivate remaining active sites on the solid support. Three washing cycles, each consisting of pH 4.0 acetate buffer followed by borate buffer, both containing sodium chloride, were used to remove unbound materials from the support. For myoglobin derivatized supports, a final wash with distilled water was used, and the moist suspension stored at 4° C. until used. For hemoglobin derivatized supports, 5 mL 0.1% glutaraldehyde solution were added to the moist suspension resulting from the above procedure, and the suspension was incubated overnight at 4° C. Three washing cycles, each consisting of pH 4.0 acetate buffer followed by borate buffer at pH 8.0, were used to remove unbound materials from the support. A fmal wash was done with distilled water, and the moist suspension stored at 4° C. until used.

F. ATTACHMENT OF HORSE RADISH PEROXIDASE (HRPO) ALDEHYDE TO HEMOGLOBIN OR MYOGLOBIN DERIVATIZED SUPPORTS

1. MATERIALS
   a. HRPO aldehyde prepared as described in PREPARATION D
   b. Hemoglobin or myoglobin derivatized solid supports prepared as described in PREPARATION E
   c. 100 mM Sodium cyanoborohydride
   d. 1.0 M NaCl
   e. distilled water

2. PROCEDURE

The three mL HRPO aldehyde (30 mg) recovered from the P-30 column in PREPARATION D were added to 1 gram of the hemoglobin or myoglobin derivatized solid supports described in PREPARATION E. The suspension was incubated for 16 hours at 4° C. followed by 4 hours at room temperature. Three washing cycles, each consisting of distilled water and 1.0 M NaCl, were used to remove unbound materials from the support. The solid support was then incubated with 5 mL 100 mM cyanoborohydride overnight at 4° C. A fmal wash was done with distilled water, and the moist suspension stored at 4° C. until used.

G. PREPARATION OF ALDEHYDE-ACTIVATED Sigmacell® 20

1. MATERIALS
   a. Sigmacell® 20 (from Sigma Chemical Co.)
   b. Distilled Water
   c. Solid Sodium periodate
   d. 20 mM Sodium bicarbonate, pH 9.5

2. PROCEDURE

Solid sodium periodate (428 mg) was added to one gram Sigmacell® suspended in 10 mL distilled water. The mixture was rotated continuously at room temperature for 2 hours. The pellet was removed by centrifugation, washed five times with 10 mL distilled water and once with 10 mL 20 mM sodium bicarbonate, pH 9.5. The resin was used immediately after preparation.

H. COVALENT ATTACHMENT OF HEMOGLOBIN AND MYOGLOBIN TO ALDEHYDE-ACTIVATED SIGMACELL® 20

1. MATERIALS
   a. Aldehyde-activated Sigmacell® 20 (PREPARATION G)
   b. Distilled Water
   c. 100 mM Sodium cyanoborohydride
   d. Human hemoglobin and horse heart Myoglobin (both from Sigma Chemical Co.)
   e. Buffers
      i. 20 mM Sodium bicarbonate, pH 9.5
      ii. 50 mM Ethanolamine, pH 9.5
      iii. 100 mM M Tris buffer, pH 8.0 containing 0.5 M NaCl
      iv. 100 mM Sodium acetate buffer, pH 4.0 containing 0.5 M NaCl
      v. 20 mM MES buffer, pH 5.0

2. PROCEDURE

Fifty mg of either myoglobin or hemoglobin dissolved in 9 mL sodium bicarbonate, pH 9.5 were added to 1 mL of aldehyde-activated Sigmacell® 20 (PREPARATION G). The suspension was rotated overnight at room temperature, and the pellet removed by centrifugation. The pellet was washed with 10 mL water. Nine mL 50 mM ethanolamine, pH 9.5 were added, and the mixture rotated continuously at room temperature for one hour. The pellet was isolated by centrifugation and washed sequentially with 10 mL each of acetate buffer, Tris buffer, and MES buffer. Twenty mL of an aqueous solution of 100 mM sodium cyanoborohydride were added, and the mixture incubated for one hour with continuous rotation at room temperature, followed by overnight incubation at 4° C. After the overnight incubation, the derivatized support was washed five times with 10 mL aliquots of dislled water and twice with 10 mL aliquots MES buffer.

I. COVALENT ATTACHMENT OF HRPO ALDEHYDE TO HEMOGLOBIN OR MYOGLOBIN IMMOBILIZED ON ALDEHYDE-ACTIVATED SIGMACELL® 20

1. MATERIALS
   a. Hemoglobin or myoglobin derivatized Sigmacell® 20 (PREPARATION H)
   b. Distilled Water
   c. 100 mM sodium cyanoborohydride
   d. Buffers
      i. 100 mM M Tris buffer, pH 8.0 containing 0.5 M NaCl
      ii. 100 mM Sodium acetate buffer, pH 4.0 containing 0.5 M NaCl
      iii. 20 mM MES buffer, pH 5.0
   e. Aldehyde-Activated HRPO (PREPARATION D)

2. PROCEDURE

Twenty milligrams desalted HRPO aldehyde (PREPARATION D) dissolved in 2 mL MES buffer, pH 5.0 were added to 1 gram hemoglobin or myoglobin derivatized Sigmacell® 20 (PREPARATION H), and the suspension rotated for 1 hour at room temperature followed by overnight incubation at 4° C. The support was isolated by centrifugation, and washed twice with 10 mL aliquots of distilled water. Twenty mL 100 mM sodium cyanoborohydride were added, and the suspension incubated for 60 hours at 4° C. The pellet was washed sequentially twice with each of the following: distilled water; acetate buffer; Tris buffer; and MES buffer.

J. COVALENT ATTACHMENT OF HEMOGLOBIN TO COMMERCIAL EUPERGIT® C ACRYLIC BEADS

1. MATERIALS
   a. Oxirane acrylic beads (Eupergit® C, from Sigma Chemical Co.)
   b. Human hemoglobin (type IV from Sigma Chemical Co.)
   c. Buffers and solutions i. 1.0 M Potassium Phosphate buffer, pH 7.5 containing 0.1% sodium azide (w/v)
ii. 1.0 M NaCl
iii. 5% (v/v) Mercaptoethanol, adjusted to pH 8.0 with 0.5 M NaOH
iv. 100 mM Potassium phosphate buffer, pH 7.4
v. 500 mM Potassium phosphate buffer, pH 7.4
vi. 3.5 M Sodium thiocyanate
vii. Phosphate buffered saline (PBS) (0.01 M sodium phosphate, pH 7.2 containing 0.15 M NaCl)
d. Distilled water

2. PROCEDURE

Hemoglobin (125 mg) was dissolved in 5 mL 1.0 M phosphate buffer, pH 7.5 containing sodium azide and added to 1 gram Eupergit® C. The mixture was allowed to incubate without agitation for 72 hours at room temperature. The support was washed three times with 1.0 M NaCl and five times with distilled water. The support was mixed with 2.5 mL mercaptoethanol previously adjusted to pH 8.0, and the suspension allowed to stand overnight at room temperature. The beads were washed 10 times with distilled water, placed on a small sintered glass funnel, and washed sequentially with 50 mL of each of the following: 0.5 M potassium phosphate buffer, pH 7.5; 0.1 M potassium phosphate buffer pH 7.5; 3.5 M sodium thiocyanate; and fially with large volumes of phosphate buffered saline (PBS) (0.01 M sodium phosphate, pH 7.2 containing 0.15 M NaCl). The derivatized beads were treated with 0.1% (v/v) glutaraldehyde with rotation for 2 hours at room temperature, overnight at 4° C., and then washed with distilled water.

K. COVALENT ATTACHMENT OF HRPO ALDEHYDE (PREPARATION D) TO HEMOGLOBIN DERIVATIZED Eupergit® C (PREPARATION J)

1. MATERIALS
a. HRPO aldehyde (PREPARATION D)
b. Hemoglobin derivatized Eupergit® C (PREPARATION J)
c. 100 mM Sodium cyanoborohydride
d. 1.0 M NaCl
e. Distilled water

2. PROCEDURES

Thirty milligrams of HRPO aldehyde (PREPARATION D) in three mL MES buffer were added to 1 gram hemoglobin derivatized Eupergit® C (PREPARATION J). The suspension was incubated for 16 hours at 4° C. followed by 4 hours at room temperature. Three washing cycles, each consisting of distilled water and 1.0 M NaCl were used to remove unbound materials from the support. The solid support was then incubated with 5 mL 100 mM cyanoborohydride for 60 hours at 4° C. A final wash was done with distilled water, and the moist suspension stored at 4° C. until used.

L. COVALENT ATTACHMENT OF CASEIN-HRPO TO POLYMERIC DIALDEHYDE

1. MATERIALS
a. 25 mg Kappa-Casein-HRPO conjugate prepared by the hydrazide method (PREPARATION B) dissolved in 2 mL 100 mM borate buffer, pH 9.0
b. Polymeric dialdehyde (from Sigma Chemical Co.)
c. Buffers:
i. 100 mM Ethanolamine, pH 9.5
ii. 100 mM Sodium borate buffer, pH 9.0 containing 0.5 M NaCl
iii. 100 mM Sodium acetate buffer, pH 4.0 containing 0.5 M NaCl
iv. 50 mM MES buffer, pH 6.0
d. 100 mM Formaldehyde
e. 100 mM Sodium cyanoborohydride

2. PROCEDURE

Two mL of Kappa-Casein-HRPO conjugate were prepared as described in PREPARATION B with one modification: the formaldehyde treatment was omitted. This solution was mixed with three mL MES buffer, and the solution added to 1 gram polymeric dialdehyde. The suspension was rotated at room temperature for 6 hours, and incubated overnight at 4° C. Two hundred microliters of 100 mM formaldehyde were added to the suspension and the mixture incubated for 1 hour at room temperature. The resin was removed by centrifugation, washed with water, and resuspended in 3 mL 100 mM ethanolamine, pH 8.5. After a two hour incubation with rotation at room temperature, the resin was sequentially washed acetate buffer, borate buffer, and water. The solid support was then incubated with 5 mL 100 mM cyanoborohydride overnight at 4° C. A final wash was done with distilled water, and the moist suspension stored at 4° C. until used.

M. ATTACHMENT OF HRPO-LABELED (ALDEHYDE METHOD) WHOLE CASEIN OR KAPPA-CASEIN TO EUPERGIT® C ACRYLIC BEADS

1. MATERIALS
a. Oxirane acrylic beads (Eupergit® C, from Sigma Chemical Co.)
b. Bovine whole Casein or Kappa-Casein (from Sigma Chemical Co.)
c. Buffers and solutions
i. 100 mM Sodium bicarbonate, pH 8.5 containing 0.5 M NaCl
ii. 100 mM Sodium acetate buffer pH 4.0 containing 0.5 M NaCl
iii. 100 mM Tris buffer pH 8.0, containing 0.5 M NaCl
iv. 20 mM MES buffer, pH 5.0
v. 5% (v/v) mercaptoethanol in water
vi. 200 mM Sodium borohydride in water
d. Distilled water

2. PROCEDURES a. Covalent Attachment of Casein or Kappa-Casein to Eupergit® C Beads 2 mL of a solution containing either whole casein or Kappa-Casein (10 mg/mL) in 100 mM sodium bicarbonate buffer, pH 8.5 and containing 0.5 M NaCl were added to 1 mL of Eupergit® C beads suspended in water. The mixture was incubated with rotation for 48 hours at room temperature. The pellet was isolated by centrifugation, and washed sequentially with 9 mL aliquots of Acetate and Tris buffers, followed by two washings with 9 mL aliquots of MES buffer. Ten mL 5% mercaptoethanol were added and the mixture incubated with rotary mixing overnight at room temperature. The casein-derivatized support was isolated by centrifugation, and washed four times with 9 mL MES buffer.

b. Labeling of Casein immobilized on Eupergit® C with HRPO

Three mL aldehyde activated HRPO (PREPARATION D) were added to the casein-derivatized Eupergit® C from section A above, and the mixture incubated with rotation for 1 hour at room temperature, and 60 hours at 4° C. The pellet was isolated by centrifugation, and washed with two 10 mL aliquots of water. An aqueous solution of sodium borohydride (5 mL) was added to the pellet, and the suspension incubated for 6 hours at room temperature. The pellet was isolated by centrifugation, and washed sequentially with 9 mL aliquots of Acetate, Tris, Acetate, Tris, and MES buffer.

N. COVALENT ATTACHMENT OF MYOGLOBIN-HRPO TO POLYMERIC DIALDEHYDE

1. MATERIALS
a. 30 mg horse heart myoglobin dissolved in 2 mL 20 mM sodium bicarbonate buffer, pH 9.5
b. Polymeric dialdehyde (cellulose dialdehyde, purchased from Sigma Chemical Co.)
c. Buffers:
   i. 50 mM Ethanolamine, pH 9.5
   ii. 100 mM Sodium borate, pH 9.0 containing 0.5 M NaCl
   iii. 100 mM Sodium acetate buffer, pH 4.0 containing 0.5 M NaCl
   iv. 50 mM MES buffer, pH 6.0
   v. 100 mM Tris buffer, pH 8.0 containing 0.5 M Nacl
d. 100 mM Formaldehyde
e. 100 mM Sodium cyanoborohydride in water

2. PROCEDURE
a. Covalent Binding of Myoglobin to Polymeric Dialdehyde

Two mL of the myoglobin solution were mixed with 1 mL of a suspension of polymeric dialdehyde and the suspension was rotated at room temperature overnight. The resin was separated by centrifugation and washed twice with 10 mL aliquots of water. Nine mL ethanolamine solution were added and the suspension incubated with rotation for 1 hour at room temperature. The resin was isolated by centrifugation, and washed sequentially with 10 mL aliquots of acetate, Tris, and MES buffer. Twenty mL of sodium cyanoborohydride were added. The suspension incubated overnight at 4° C. The Myoglobin-derivatized polymeric dialdehyde was washed five times with 10 mL aliquots of water, and twice with MES buffer.

b. Labelling of Myoglobin-Derivatzed Beads with HRPO Aldehyde (PREPARATION D).

Two mL desalted HRPO aldehyde (PREPARATION D) were added to the resin, and the suspension incubated with rotation at room temperature for 1 hour, and overnight a 4° C. The resin was then isolated by centrifugation, washed twice with 10 mL aliquots of water, suspended in 20 mL sodium cyanoborohydride, and incubated 60 hours at 4° C. The resin was isolated by centrifugation, washed twice with 10 mL aliquots of water, then twice sequentially with four 10 mL aliquots of acetate/NaCl and Tris/NaCl buffers. Finally, the resin was washed with 10 mL MES buffer and stored at 4° C. until used.

O. PREPARATION OF HRPO LABELED CHITIN AND ITS USE TO ASSAY CHITINASE

1. MATERIALS
a. Cyanogen bromide activated chitin (PREPARATION A)
b. HRPO (Type II from Sigma Chemical Co., 78 units/mg)
c. Chitinase (EC 3.2.1.14, isolated from *Streptomyces grisius* and purchased from Sigma Chemical Co.)
d. Buffers:
   i. 500 mM Tris/MES buffer, pH 5.4
   ii. Coupling buffer, 100 mM sodium bicarbonate containing 0.5 M NaCl
   iii. 100 mM Sodium acetate buffer, pH 4.0, containing 0.5 M NaCl
   iv. 100 mM Sodium borate buffer, pH 8.0, containing 0.5 M NaCl
   v. 1.0 M Tris buffer, pH 8.0
e. ABTS assay mix: 40 microliters 25 mg/mnL ABTS (2,2'-Azino-di[3-ethylbenzthiazoline sulfonic acid, diammonium salt]; 10 microliters 1% (v/v) hydrogen peroxide; 950 microliters water

2. Procedure
a. Preparation of HRPO-Derivatized Chitin

Five hundred mg cyanogen bromide activated chitin (PREPARATION A) were suspended in 5 mL coupling buffer, 5 mg HRPO were added, and the suspension mixed end-over-end for 2 hours at room temperature. The solid material was washed with distilled water and coupling buffer. Three mL 1.0 M Tris, pH 8.0 buffer were added to the support, and the suspension stirred at room temperature for 2 hours before being washed 3 times sequentially with acetate and borate buffers, and finally with water.

b. Chitinase Assay

Fifty mg HRPO labeled chitin were suspended in 200 microliters MES/Tris buffer. Fifty microliters of a solution of Chitinase (50 units/mL) were added, and the mixture incubated for 4 hours at 37° C. The reaction mixture was centrifuged to sediment the chitin, and a 10 microliter aliquot of the supernatant was mixed with 100 microliters of the ABTS assay mix. The chitinase-catalyzed release of chitin-bound HRPO was detected by the generation of a green color in the solution.

P. PREPARATION OF CYANOGEN BROMIDE ACTIVATED SEPHAROSE-CASEIN OR KAPPA-CASEIN-HRPO ALDEHYDE

1. MATERIALS
a. Cyanogen bromide activated Sepharose (PREPARATION A)
b. Casein or Kappa-Casein at 10 mg/mL in coupling buffer (0.1 M sodium bicarbonate containing 0.5 M NaCl)
c. Buffers and Solutions:
   i. 50 mM Ethanolamine, pH 9.5
   ii. 100 mM Sodium borate, pH 9.0 containing 0.5 M NaCl
   iii. 100 mM Sodium acetate buffer, pH 4.0 containing 0.5 M NaCl
   iv. 20 mM MES buffer, pH 5.0
   v. 100 mM Tris buffer, pH 8.5 containing 0.5 M NaCl
   vi. 100 mM sodium borohydride in water
d. HRPO aldehyde (PREPARATION D)

2. PROCEDURE

Two mL Casein or Kappa-Casein solution were added to one mL cyanogen bromide activated Sepharose and the suspension incubated for 2 hours with rotation at room temperature. Seven mL ethanolamine solution were added, and the mixture incubated for 1 hour at room temperature. The resin was isolated by centrifugation, and washed sequentially with 9 mL aliquots of acetate and Tris buffers containing sodium chloride, followed by two washes with 9 mL of MES buffer.

3 mL desalted HRPO aldehyde (PREPARATION D) were added, and the mixture rotated for 1 hour at room temperature, followed by overnight incubation at 4° C. The resin was isolated by centrifugation, and washed twice with 10 mL water. The resin was suspended in 10 mL sodium borohydride, and the mixture incubated for 2 hours at room temperature. Finally, the resin was isolated by centrifugation, and washed sequentially with 9 mL of each of the following buffers containing 0.5 M NaCl: acetate; Tris; acetate; and Tris. The resin was finally washed with 9 mL MES buffer, and stored in MES buffer at 4° C. until used.

Q. COVALENT ATTACHMENT OF MYOGLOBIN AND BOVINE SERUM ALBUMIN TO FINELY PULVERIZED EUPERGIT® C ACRYLIC BEADS (Eupergit® C) AND

SUBSEQUENT COVALENT LABELING WITH HORSE RADISH PEROXIDASE (ALDEHYDE METHOD)

Step 1: Covalent Attachment of Myoglobin and Bovine Serum Albumin to Eupergit® C Acrylic Beads (Eupergit® C)

1. MATERIALS
   a. Oxirane acrylic beads (Eupergit® C, 150 micron beads from Sigma Chemical Co.)
   b. Horse heart myoglobin (type IV) or bovine serum albumin (from Sigma Chemical Co.)
   c. Buffers and solutions
      i. 1.0 M Potassium Phosphate buffer, pH 7.5 containing 0.1% sodium azide (w/v)
      ii. 1.0 M NaCl
      iii. 5% (v/v) Mercaptoethanol, adjusted to pH 8.0 with 0.5 N NaOH
      iv. 100 mM Potassium phosphate buffer, pH 7.5
      v. 500 mM Potassium phosphate buffer, pH 7.5
      vi. 3.5 M Sodium thiocyanate
      vii. Phosphate buffered saline (PBS) (0.01 M sodium phosphate, pH 7.2 containing 0.15 M NaCl
   d. Distilled water

2. PROCEDURE

One gram of oxirane acrylic beads were ground to a fine powder manually with a mortar and pestle. Myoglobin or bovine serum albumin (125 mg) were dissolved in 5 mL 1.0 M phosphate buffer, pH 7.5 containing sodium azide and added to 1 gram finely ground Eupergit® C. The mixture was allowed to incubate without agitation for 72 hours at room temperature. Using centrifugation, the support was washed three times with 1.0 M NaCl and five times with 20 mL distilled water. The support was mixed with 2.5 mL mercaptoethanol previously adjusted to pH 8.0, and the suspension allowed to stand overnight at room temperature. The beads were washed 10 times, using centrifugation, with distilled water and washed sequentially with 50 mL of each of the following: 0.5 M potassium phosphate buffer, pH 7.5; 0.1 M potassium phosphate buffer, pH 7.5; 3.5 M sodium thiocyanate; and fmally with large volumes of phosphate buffered saline (PBS) (0.01 M sodium phosphate, pH 7.2 containing 0.15 M NaCl).

Step 2: Covalent Labeling with Horse Radish Peroxidase (ALDEHYDE METHOD) Horse Radish Peroxidase aldehyde (PREPARATION D) was used to label the above myoglobin or albumin derivatized acrylic beads from step 1 above using PROCEDURE F.

R. COUPLING OF SIGMACELL®-20 MYOGLOBIN TO HRPO WITH GLUTARALDEHYDE

1. MATERIALS
   a. Myoglobin covalently attached to cyanogen bromide activated Sigmacell® 20 (PREPARATION E)
   b. 0.5 M MES buffer, pH 5.0
   c. 1% (v/v) glutaraldehyde in water
   d. HRPO-hydrazide (from Sigma Chemical Co., 200 units/mg)
   e. 100 mM formaldehyde
   f. 100 mM sodium cyanoborohydride
   g. 0.5 M NaCl

2. PROCEDURES

One mL of glutaraldehyde solution was added to 1 gram of myoglobin conjugated Sigmacell® 20, and the suspension rotated at room temperature for 30 minutes and washed with water. Five mg HRPO hydrazide in 2 mL of 100 mM MES buffer were added to the washed resin and the suspension rotated for 4 hours at room temperature. Two hundred microliters of 100 mM formaldehyde solution were added, and the mixture allowed to incubate for 30 minutes at room temperature. The resin was washed with water, suspended in 5 mL of 100 mM sodium cyanoborohydride, and incubated overnight at 4° C. The resin was then washed with distilled water and 0.5 M NaCl and stored as a moist paste until used.

S. PREPARATION OF GUAIAC SOLUTION AND GUAIAC SHEETS

1. Guaiac, Hydroxypropyl Cellulose Solution (i.e., Guaiac Ink)

150 grams of powdered guaiac are dissolved in 660 mL warm, stirred ethanol. To the resulting solution 1330 mL of distilled water are added and the resulting suspension allowed to cool to room temperature. After two hours, the supernatant is decanted and the residual suspension retained.

250 mL of a 10% (w/w) solution of hydroxypropyl cellulose in ethanol is mixed with an additional 250 mL of ethanol, and the resulting solution is added to the guaiac slurry. The mixture is stirred until the guaiac residue has completely dissolved.

2. Guaiac Sheets

One mL of the above guaiac solution is pipetted onto the polyethylene side of a 10 inch×10 inch sheet of a Mylar/polyethylene laminate (7 mils Mylar/3 mL polyethylene). The guaiac solution is spread over the surface of the sheets by means of a standard wound-wire testing bar, and allowed to dry at room temperature.

T. PREPARATION OF SODIUM PERBORATE SUSPENSION (i.e., SODIUM PERBORATE INK)

Twenty grams of finely ground solid sodium perborate is mixed with a sufficient volume of 10% (w/w) solution of hydroxypropyl cellulose solution in anhydrous alcohol to produce one liter of suspension.

II. EXPERIMENTS

EXPERMENT I

This experiment involves the release of HRPO from [SEPHAROSE-CASEIN-HRPO] and [SEPHAROSE-KAPPA-CASEIN-HRPO] by aspartic protease released into *Candida albicans* culture.

A. MATERIALS: (CYANOGEN BROMIDE ACTIVATED SEPHAROSE) (HRPO ALDEHYDE COUPLING METHOD)

1. Cyanogen bromide activated Sepharose 4B (PREPARATION A) first derivatized with covalently bound casein or Kappa-Casein (PREPARATION P) and subsequently labeled with HRPO aldehyde (PREPARATION D)
2. Aspartic Protease producing *Candida albicans* (ATCC 28366) culture propagated and grown in liquid culture as described in *Journal of General Microbiology*, (1983) 129:431–438.
3. Guaiac layered sheets (PREPARATION S)
4. Buffers and solutions
   a. 20 mM hydrogen peroxide
   b. 500 mM MES buffer, pH 6.0

B. PROCEDURES 10 mg (wet weight) [Sepbarose-Casein-HRPO] conjugate (or the Kappa-Casein equivalent) were suspended in 300 microliters of either *Candida albicans* culture containing active secreted aspartic protease, or 300 microliters of the same *Candida albicans* culture which had been boiled for 20 minutes to inactivate the aspartic protease. The mixture was rotated for 15 minutes at room temperature, and the suspension centrifuged to sediment the solid conjugate and *Candida albicans* cells.

Eighty microliters of the clear supernatant were mixed with 10 microliters of hydrogen peroxide solution and 10 microliters of MES buffer. Twenty microliters of each solution were added to the surface of a guaiac layered sheet, and the sheet examined for formation of a blue color.

| COLOR SCORE: | INTERPRETATION |
| --- | --- |
| 0 | NO VISIBLE BLUE COLOR FORMATION |
| +/− | POSSIBLE BLUE COLOR |
| 0.25 | FAINTEST BLUE COLOR DETECTABLE VISUALLY |
| 0.5 | DISTINCT BLUE COLOR |
| 1.0 | DARK BLUE COLOR |
| 1.5 | BLUE COLOR BETWEEN 1.0 AND 2.0 IN INTENSITY |
| 2.0 | DARKEST BLUE COLOR POSSIBLE IN TEST SYSTEM |

C. RESULTS

A dark blue color formed on the guaiac layered sheet in the area to which *Candida albicans* treated Sepharose-protein-HRPO supernatant was added. No color was seen in the area to which boiled culture treated Sepharose-protein-HRPO supernatant was added.

| ENZYME SOURCE | COLOR SCORE |
| --- | --- |
| *Candida albicans* culture | 1.5 |
| Boiled culture | 0 |

D. INTERPRETATION

Active aspartic protease secreted into the growth medium by *Candida albicans* cells hydrolyzed Sepharose bound Casein or Kappa-Casein, releasing soluble, active HRPO. Centrifugation sedimented Sepharose bound HRPO, leaving only aspartic protease-solubilized HRPO in solution. The soluble HRPO catalyzed the oxidation of guaiac by hydrogen peroxide, producing a blue color. Hence, blue color formation on the guaiac layered sheets provides a convenient method for detecting aspartic protease.

Boiling the culture inactivated aspartic protease secreted into the growth medium by *Candida albicans* cells. Hence, Sepharose bound casein or Kappa-Casein was not hydrolyzed, and soluble, active HRPO was not released from the support. Centrifugation sedimented Sepharose bound HRPO, leaving no aspartic protease-solubilized HRPO in solution. The oxidation of guaiac by hydrogen peroxide was not catalyzed, and a barely detectable blue color formed. Release of HRPO from the support was not simply the result of non specific release of HRPO by salts or other components present in the growth medium.

EXPERIMENT H

This experiment involves the release of HRPO from [EUPERGIT® C ACRYLIC BEADS-CASEIN-HRPO] conjugates and [EUPERGIT® C ACRYLIC BEADS-KAPPA-CASEIN-HRPO] conjugates by aspartic protease released into *Candida albicans* culture:

A. MATERIALS: (EUPERGIT® C ACTIVATED ACRYLIC BEADS) (HRPO ALDEHYDE COUPLING METHOD)

1. Oxirane acrylic beads (Eupergit® C) were treated with Casein or Kappa-Casein (PREPARATION M) and subsequently labeled with HRPO aldehyde (PREPARATION D)
2. Aspartic Protease producing *Candida albicans* (ATCC 28366) culture propagated and grown in liquid culture as described in *Journal of General Microbiology*, (1983) 129: 431–438.
3. Guaiac layered sheets (PREPARATION S)
4. Buffers and solutions
   a. 20 mM hydrogen peroxide
   b. 500 mM MES buffer, pH 6.0

B. PROCEDURES 10 mg (wet weight) [Eupergit® C-Casein-HRPO] conjugate (or the Kappa-Casein equivalent) were suspended in 300 microliters of either *Candida albicans* culture containing secreted active aspartic protease, or 300 microliters of the same *Candida albicans* culture which had been boiled for 20 minutes to inactivate the aspartic protease. The mixture was rotated for 15 minutes at room temperature, and the suspension centrifuged to sediment the solid conjugate and *Candida albicans* cells.

Eighty microliters of the clear supernatant were mixed with 10 microliters of hydrogen peroxide solution and 10 microliters of MES buffer. Twenty microliters of each solution were added to surface of a guaiac layered sheet, and the sheet examined for formation of a blue color.

| COLOR SCORE | INTERPRETATION |
| --- | --- |
| 0 | NO VISIBLE BLUE COLOR FORMATION |
| +/− | POSSIBLE BLUE COLOR |
| 0.25 | FAINTEST BLUE COLOR DETECTABLE VISUALLY |
| 0.5 | DISTINCT BLUE COLOR |
| 1.0 | DARK BLUE COLOR |
| 1.5 | BLUE COLOR BETWEEN 1.0 AND 2.0 IN INTENSITY |
| 2.0 | DARKEST BLUE COLOR POSSIBLE IN TEST SYSTEM |

C. RESULTS

A dark blue color formed on the guaiac layered sheet in the area to which *Candida albicans* treated [Eupergit® C-Protein-HRPO] supernatant was added. No color was seen in the area to which boiled culture treated [Eupergit® C-Protein-HRPO] supernatant was added.

| ENZYME SOURCE | COLOR SCORE |
| --- | --- |
| *Candida albicans* culture | 1.5 |
| Boiled culture | 0 |

D. INTERPRETATION

Active aspartic protease secreted into the growth medium by *Candida albicans* cells hydrolyzed Eupergit® C bound Casein or Kappa-Casein, releasing soluble, active HRPO. Centrifugation sedimented Eupergit® C bound HRPO, leaving only aspartic protease-solubilized HRPO in solution. The soluble HRPO catalyzed the oxidation of guaiac by hydrogen peroxide, producing a blue color. Hence, blue color formation on the guaiac layered sheets provides a convenient method for detecting aspartic protease.

Boiling the culture inactivated aspartic protease secreted into the growth medium by *Candida albicans* cells. Hence, Eupergit® C bound casein or Kappa-Casein was not hydrolyzed, and soluble, active HRPO was not released from the support. Centrifugation sedimented Eupergit® C bound HRPO, leaving no aspartic protease-solubilized HRPO in solution. The oxidation of guaiac by hydrogen peroxide was not catalyzed, and a barely detectable blue color formed. Release of HRPO from the support was not simply the result of non specific release of HRPO by salts or other components present in the growth medium.

EXPERIMENT III

This experiment involves the release of HRPO from [SEPHAROSE-HEMOGLOBIN-HRPO] or [SEPHAROSE-MYOGLOBIN-HRPO] by pepsin and aspartic protease from *Aspergillus saitoi*.

A. MATERIALS: (CYANOGEN BROMIDE ACTIVATED SEPHAROSE) (HRPO ALDEHYDE COUPLING METHOD)

1. Cyanogen bromide activated Sepharose 4B (PREPARATION A) first derivatized with covalently bound hemoglobin or myoglobin (PREPARATION E), and subsequently labeled with HRPO aldehyde (PREPARATIONS D and F). The conjugate was treated overnight with 100 mM sodium cyanoborohydride at room temperature and washed with 0.5 M NaCl before use.
2. Test Solutions: a. Commercially available Aspartic Protease (Type XIII) from *Aspergillus saitoi* (30 mg/mL, 0.6 units/mg); b. pepsin (1 mg/mL, 2900 units/mg); and c. Bovine Serum Albumin (BSA) (2 mg/mL in water) (all purchased from Sigma Chemical Co.)
3. Guaiac impregnated paper in the form of commercially available Hemoccult® slides (from SmithKline Diagnostics)
4. Buffers and solutions
   a. 0.02% (v/v) hydrogen peroxide in 200 mM phosphate buffer, pH 7.0
   b. 100 mM acetate buffer, pH 4.0

B. PROCEDURES 40 mg (wet weight) [Sepharose-Hemoglobin-HRPO] (or the myoglobin equivalent) conjugate were suspended in 75 microliters acetate buffer, pH 4.0 and 25 microliters of test solution were added. The suspension was incubated at room temperature for 15 minutes and centrifuged to remove the solid phase conjugate. Five microliters of the supernatant were added to a guaiac slide, followed by five microliters of hydrogen peroxide solution.

| COLOR SCORE | INTERPRETATION |
|---|---|
| 0 | NO VISIBLE BLUE COLOR FORMATION |
| +/- | POSSIBLE FAINT BLUE COLOR |
| 0.25 | FAINTEST BLUE COLOR DETECTABLE VISUALLY |
| 0.5 | DISTINCT BLUE COLOR |
| 1.0 | DARK BLUE COLOR |
| 2.0 | DARKEST BLUE COLOR POSSIBLE IN TEST SYSTEM |

C. RESULTS

A dark blue color formed on the guaiac impregnated sheet in the area to which supernatant samples containing Aspartic Protease from *Aspergillus saitoi* or pepsin were added. Only a very faint color was seen in the area to which supernatant aliquots containing only BSA alone (2 mg/mL) or buffer were added.

| ENZYME SOURCE | COLOR SCORE |
|---|---|
| Aspartic Protease | 2.0 |
| Pepsin | 2.0 |
| BSA | +/- |
| Buffer | +/- |

D. INTERPRETATION

Active *Aspergillus saitoi* aspartic protease and pepsin, an aspartic protease from porcine stomach, hydrolyzed Sepharose bound hemoglobin or myoglobin, releasing soluble, active HRPO. Centrifugation sedimented Sepharose bound HRPO, leaving only enzyme solubilized HRPO in solution. The soluble HRPO catalyzed the oxidation of guaiac by hydrogen peroxide, producing a blue color. Hence, blue color formation on the guaiac layered sheets provides a convenient method for detecting active Aspergillus aspartic protease or porcine pepsin.

Neither BSA nor buffer have aspartic protease activity. Hence, Sepharose bound hemoglobin or myoglobin were not hydrolyzed, and soluble, active HRPO was not released from the support. Centrifugation sedimented Sepharose bound HRPO, leaving no aspartic protease-solubilized HRPO in solution. The oxidation of guaiac by hydrogen peroxide was not catalyzed, and a barely detectable blue color formed.

EXPERIMENT IV

This experiment involves the release of HRPO from [SEPHAROSE-CASEIN-HRPO] or [SEPHAROSE-KAPPA-CASEIN-HRPO] by pepsin and aspartic protease from *Aspergillus saitoi*:

A. MATERIALS: (CYANOGEN BROMIDE ACTIVATED SEPHAROSE) (HRPO HYDRAZIDE COUPLING METHOD)

1. Cyanogen bromide activated Sepharose 4B PREPARATION A) allowed to react with Kappa-Casein-HRPO or Casein-HRPO (hydrazide method) (PREPARATIONS B and C)
2. Test Solutions: a. Commercially available Aspartic Protease from *Aspergillus saitoi* (30 mg/mL, 0.6 units/mg); b. pepsin (1 mg/mL, 2900 units/mg); and c. Bovine Serum Albumin (BSA)(2 mg/mL in water) (all purchased from Sigma Chemical Co.)
3. Guaiac impregnated paper in the form of commercially available Hemoccult® slides
4. Buffers and solutions
   a. 0.02% (v/v) hydrogen peroxide in 200 mM phosphate buffer, pH 7.0
   b. 100 mM acetate buffer, pH 4.0

B. PROCEDURES 40 mg (wet weight) [Sepharose-Casein-HRPO] (or the Kappa-Casein equivalent) conjugate were suspended in 75 microliters acetate buffer, pH 4.0 and 25 microliters of test solution were added. The suspension was incubated at room temperature for 15 minutes and centrifuged to remove the solid phase conjugate. Five microliters of the supernatant were added to a guaiac slide, followed by five microliters of hydrogen peroxide solution.

| COLOR SCORE | INTERPRETATION |
| --- | --- |
| 0 | NO VISIBLE BLUE COLOR FORMATION |
| +/− | POSSIBLE FAINT BLUE COLOR |
| 0.25 | FAINTEST BLUE COLOR DETECTABLE VISUALLY |
| 0.5 | DISTINCT BLUE COLOR |
| 1.0 | DARK BLUE COLOR |
| 2.0 | DARKEST BLUE COLOR POSSIBLE IN TEST SYSTEM |

C. RESULTS

A dark blue color formed on the guaiac impregnated sheet in the area to which supernatant samples containing Aspartic Protease from *Aspergillus saitoi* or pepsin were added. Only the faintest color detectable was seen in the area to which supernatant aliquots containing only BSA (2.0 mg/mL) or buffer were added.

| ENZYME SOURCE | COLOR SCORE |
| --- | --- |
| Aspartic Protease | 2.0 |
| Pepsin | 2.0 |
| BSA | +/− |
| Buffer | +/− |

D. INTERPRETATION

Active *Aspergillus saitoi* aspartic protease and porcine pepsin hydrolyzed Sepharose bound Casein or Kappa-Casein, releasing soluble, active HRPO. Centrifugation sedimented Sepharose bound HRPO, leaving only enzyme solubilized HRPO in solution. The soluble HRPO catalyzed the oxidation of guaiac by hydrogen peroxide, producing a blue color. Hence, blue color formation on the guaiac layered sheets provides a convenient method for detecting aspartic protease or pepsin.

Neither BSA nor buffer have aspartic protease activity. Hence, Sepharose bound casein or Kappa-Casein were not hydrolyzed, and soluble, active HRPO was not released from the support. Centrifugation sedimented Sepharose bound HRPO, leaving no aspartic protease-solubilized HRPO in solution. The oxidation of guaiac by hydrogen peroxide was not catalyzed, and a barely detectable blue color formed.

EXPERIMENT V

This experiment involves the release of HRPO from [CHITIN-KAPPA-CASEIN-HRPO] by pepsin and aspartic protease from *Aspergillus saitoi*.

A. MATERIALS: (CYANOGEN BROMIDE ACTIVATED CHITIN) (HRPO HYDRAZIDE COUPLING METHOD)

1. Cyanogen bromide activated chitin (PREPARATION A) were allowed to react with Kappa-Casein-HRPO (hydrazide method) (PREPARATION B and C)
2. Test Solutions: a. Commercially available Aspartic Protease from *Aspergillus saitoi* (30 mg/mL, 0.6 units/mg); b. pepsin (1 mg/mL, 2900 units/mg); and c. Bovine Serum Albumin (BSA)(2 mg/mL in water) (all purchased from Sigma Chemical Co.)
3. Guaiac impregnated paper in the form of commercially available Hemoccult® slides (from SmithKline Diagnostics)
4. Buffers and solutions
   a. 0.02% (v/v) hydrogen peroxide in 200 mM phosphate buffer, pH 7.0
   b. 100 mM acetate buffer, pH 4.0

B. PROCEDURES 40 mg (wet weight) [Chitin-Kappa-Casein-HRPO] conjugate were suspended in 75 microliters acetate buffer, pH 4.0 and 25 microliters of test solution were added. The suspension was incubated at room temperature for 15 minutes and centriuged to remove the solid phase conjugate. Five $\mu$l of the supernatant were added to a guaiac slide, followed by five microliters of hydrogen peroxide solution.

| COLOR SCORE | INTERPRETATION |
| --- | --- |
| 0 | NO VISIBLE BLUE COLOR FORMATION |
| +/− | POSSIBLE FAINT BLUE COLOR |
| 0.25 | FAINTEST BLUE COLOR DETECTABLE VISUALLY |
| 0.5 | DISTINCT BLUE COLOR |
| 1.0 | DARK BLUE COLOR |
| 2.0 | DARKEST BLUE COLOR POSSIBLE IN TEST SYSTEM |

C. RESULTS

A dark blue color formed on the guaiac impregnated sheet in the area to which supernatant samples containing Aspartic Protease from *Aspergillus satoi* or pepsin were added. Only a barely detectable blue color was seen in the area to which supernatant aliquots after BSA (2.0 mg/mL) or buffer were added.

| ENZYME SOURCE | COLOR SCORE |
| --- | --- |
| Aspartic Protease | 2.0 |
| Pepsin | 2.0 |
| BSA | +/− |
| Buffer | +/− |

D. INTERPRETATION

Active *Aspergillus saitoi* aspartic protease and porcine pepsin hydrolyzed Sigmacell® 20 bound hemoglobin or myoglobin, releasing soluble, active HRPO. Centrifugation sedimented Sigmacell® 20 bound HRPO, leaving only enzyme solubilized HRPO in solution. The soluble HRPO catalyzed the oxidation of guaiac by hydrogen peroxide, producing a blue color. Hence, blue color formation on the guaiac layered sheets provides a convenient method for detecting aspartic protease or pepsin.

Neither BSA nor buffer have aspartic protease activity. Hence, Sigmacell® 20 bound hemoglobin or myoglobin were not hydrolyzed, and soluble, active HRPO was not released from the support. Centiflgation sedimented Sigmacell® 20 bound HRPO, leaving no aspartic protease-solubilized HRPO in solution. The oxidation of guaiac by hydrogen peroxide was not catalyzed, and a barely detectable blue color formed.

EXPERIMENT VI

This experiment involves the release of HRPO from [SIGMACELL® 20-HEMOGLOBIN-HRPO] or [SIGMACELL® 20-MYOGLOBIN-HRPO] by pepsin and aspartic protease from *Aspergillus saitoi*.

A. MATERIALS: (CYANOGEN BROMIDE ACTIVATED SIGMACELL® 20) (HRPO ALDEHYDE COUPLING METHOD)

1. Cyanogen bromide activated Sigmacell® 20 (PREPARATION A) first derivatized with covalently bound hemoglobin or myoglobin (PREPARATION E), and subsequently labeled with HRPO aldehyde (PREPARATIONS D–F). The conjugate was treated overnight with 100 mM sodium cyanoborohydride at room temperature and washed with 0.5 M NaCl before use.
2. Test Solutions: a. Commercially available Aspartic Protease from *Aspergillus saitoi* (30 mg/mL, 0.6 units/mg); b. pepsin (1 mg/mL, 2900 units/mg); and c. Bovine Serum Albumin (BSA)(2 mg/mL in water) (all purchased from Sigma Chemical Co.)
3. Guaiac impregnated paper in the form of commercially available Hemoccult® slides
4. Buffers and solutions
    a. 0.02% (v/v) hydrogen peroxide in 200 mM phosphate buffer, pH 7.0
    b. 100 mM acetate buffer, pH 4.0

B. PROCEDURES 40 mg (wet weight) [Sigmacell® 20-Hemoglobin-HRPO] (or the myoglobin equivalent) conjugate were suspended in 75 microliters acetate buffer, pH 4.0 and 25 microliters of test solution were added. The suspension was incubated at room temperature for 15 minutes and centrifuged to remove the solid phase conjugate. Five microliters of the supernatant were added to a guaiac slide, followed by five microliters of hydrogen peroxide solution.

| COLOR SCORE | INTERPRETATION |
| --- | --- |
| 0 | NO VISIBLE BLUE COLOR FORMATION |
| +/− | POSSIBLE FAINT BLUE COLOR |
| 0.25 | FAINTEST BLUE COLOR DETECTABLE VISUALLY |
| 0.5 | DISTINCT BLUE COLOR |
| 1.0 | DARK BLUE COLOR |
| 2.0 | DARKEST BLUE COLOR POSSIBLE IN TEST SYSTEM |

C. RESULTS

A dark blue color formed on the guaiac impregnated sheet in the area to which supernatant samples containing Aspartic Protease from *Aspergillus saitoi* or pepsin were added. Only a very faint color was seen in the area to which supernatant aliquots after BSA (2.0 mg/mL) or buffer were added.

| ENZYME SOURCE | COLOR SCORE |
| --- | --- |
| Aspartic Protease | 2.0 |
| Pepsin | 2.0 |
| BSA | +/− |
| Buffer | +/− |

D. INTERPRETATION

Active *Aspergillus saitoi* aspartic protease and porcine pepsin hydrolyzed Sigmacell® 20 bound hemoglobin or myoglobin, releasing soluble, active HRPO. Centrifugation sedimented Sigmacell® 20 bound HRPO, leaving only enzyme solubilized HRPO in solution. The soluble HRPO catalyzed the oxidation of guaiac by hydrogen peroxide, producing a blue color. Hence, blue color formation on the guaiac layered sheets provides a convenient method for detecting aspartic protease or pepsin.

Neither BSA nor buffer have aspartic protease activity. Hence, Sigmacell® 20 bound hemoglobin or myoglobin were not hydrolyzed, and soluble, active HRPO was not released from the support. Centrifugation sedimented Sigmacell® 20 bound HRPO, leaving no aspartic protease-solubilized HRPO in solution. The oxidation of guaiac by hydrogen peroxide was not catalyzed, and a barely detectable blue color formed.

EXPERIMENT VII

This experiment is an example of the release of HRPO from [SIGMACELL® 20-KAPPA-CASEIN-HRPO] by pepsin and aspartic protease from *Aspergillus saitoi.*

A. MATERIALS: (CYANOGEN BROMIDE ACTIVATED SIGMACELL® 20) (HRPO HYDRAZIDE COUPLING METHOD)
1. Cyanogen bromide activated Sigmacell® 20 (PREPARATION A) allowed to react with Kappa-Casein-HRPO (hydrazide method) (PREPARATIONS B and C)
2. Test Solutions: a. Commercially available Aspartic Protease from *Aspergillus saitoi* (30 mg/mL, 0.6 units/mg); b. pepsin (1 mg/mL, 2900 units/mg); and c. Bovine Serum Albumin (BSA)(2 mg/mL in water) (all purchased from Sigma Chemical Co.)
3. Guaiac impregnated paper in the form of commercially available Hemoccult® slides
4. Buffers and solutions
    a. 0.02% (v/v) hydrogen peroxide in 200 mM phosphate buffer, pH 7.0
    b. 100 mM acetate buffer, pH 4.0

B. PROCEDURES 40 mg (wet weight) [Sigmacell® 20-Kappa-Casein-HRPO] conjugate were suspended in 75 microliters acetate buffer, pH 4.0 and 25 microliters of test solution were added. The suspension was incubated at room temperature for 15 minutes and centrifuged to remove the solid phase conjugate. Five microliters of the supernatant were added to a guaiac slide, followed by five microliters of hydrogen peroxide solution.

| COLOR SCORE | INTERPRETATION |
| --- | --- |
| 0 | NO VISIBLE BLUE COLOR FORMATION |
| +/− | POSSIBLE FAINT BLUE COLOR |
| 0.25 | FAINTEST BLUE COLOR DETECTABLE VISUALLY |
| 0.5 | DISTINCT BLUE COLOR |
| 1.0 | DARK BLUE COLOR |
| 2.0 | DARKEST BLUE COLOR POSSIBLE IN TEST SYSTEM |

C. RESULTS

A dark blue color formed on the guaiac impregnated sheet in the area to which supernatant samples containing Aspartic Protease from *Aspergillus saitoi* or pepsin were added. Only a very faint color was seen in the area to which supernatant aliquots after BSA (2.0 mg/mL) or buffer were added.

| ENZYME SOURCE | COLOR SCORE |
| --- | --- |
| Aspartic Protease | 2.0 |
| Pepsin | 2.0 |
| BSA | +/− |
| Buffer | +/− |

D. INTERPRETATION

Active *Aspergillus saitoi* aspartic protease and porcine pepsin hydrolyzed Sigmacell® 20 bound Kappa-Casein, releasing soluble, active HRPO. Centrifngation sedimented Sigmacell® 20 bound HRPO, leaving only enzyme solubilized HRPO in solution. The soluble HRPO catalyzed the oxidation of guaiac by hydrogen peroxide, producing a blue color. Hence, blue color formation on the guaiac layered sheets provides a convenient method for detecting aspartic protease or pepsin.

Neither BSA nor buffer have aspartic protease activity. Hence, Sigmacell® 20 bound Kappa-Casein were not hydrolyzed, and soluble, active HRPO was not released from the support. Centrifugation sedimented Sigmacell® 20 bound HRPO, leaving no aspartic protease-solubilized HRPO in solution. The oxidation of guaiac by hydrogen peroxide was not catalyzed, and a barely detectable blue color formed.

EXPERIMENT VIII

This example is an example of the release of HRPO from [SIGMACELL® 20-KAPPA-CASEIN-HRPO] (HYDRAZIDE METHOD) or [SIGMACELL® 20-MYOGLOBIN/HEMOGLOBIN-HRPO] (ALDEHYDE METHOD) by aspartic protease from Aspergillus saitoi or Pepsin.

A. MATERIALS: (CYANOGEN BROMIDE ACTIVATED SIGMACELL® 20)
1. Cyanogen bromide activated Sigmacell® 20 (PREPARATION A) were derivatized with Kappa-Casein and HRPO (hydrazide method) (PREPARATION B). Alternatively, cyanogen bromide activated Sigmacell® 20 were derivatized with hemoglobin or myoglobin (PREPARATION E) and then coupled to HRPO aldehyde (PREPARATION D)
2. Test Solutions: a. Commercially available Aspartic Protease from Aspergillus saitoi (30 mg/mL, 0.6 units/mg); b. pepsin (1 mg/mL, 2900 units/mg); and c. Bovine Serum Albumin (BSA)(2 mg/mL in water) (all purchased from Sigma Chemical Co.)
3. Guaiac impregnated paper in the form of commercially available Hemoccult® slides
4. Buffers and solutions
   a. 0.02% (v/v) hydrogen peroxide in 200 mM phosphate buffer, pH 7.0
   b. 100 mM acetate buffer, pH 4.0

B. PROCEDURES 40 mg (wet weight) [Sigmacell® 20-Kappa-Casein-HRPO] conjugate were suspended in 75 microliters acetate buffer, pH 4.0 and 25 microliters of test solution were added. The suspension was incubated at room temperature for 15 minutes and centrifuged to remove the solid phase conjugate. Five microliters of the supernatant were added to a guaiac slide, followed by five microliters of hydrogen peroxide solution.

| COLOR SCORE | INTERPRETATION |
| --- | --- |
| 0 | NO VISIBLE BLUE COLOR FORMATION |
| +/− | POSSIBLE FAINT BLUE COLOR |
| 0.25 | FAINTEST BLUE COLOR DETECTABLE VISUALLY |
| 0.5 | DISTINCT BLUE COLOR |
| 1.0 | DARK BLUE COLOR |
| 2.0 | DARKEST BLUE COLOR POSSIBLE IN TEST SYSTEM |

C. RESULTS

A dark blue color formed on the guaiac impregnated sheet in the area to which supernatant samples containing aspartic protease from Aspergillus saitoi or pepsin were added. Only a very faint color was seen in the area to which supernatant aliquots containing BSA (2.0 mg/mL) or buffer were added.

| ENZYME SOURCE | COLOR SCORE |
| --- | --- |
| Aspartic Protease | 2.0 |
| Pepsin | 2.0 |
| BSA | +/− |
| Buffer | +/− |

D. INTERPRETATION

Active Aspergillus saitoi aspartic protease and porcine pepsin hydrolyzed Sigmacell® 20 bound Kappa-Casein, releasing soluble, active HRPO. Centrifugation sedimented Sigmacell® 20 bound HRPO, leaving only enzyme solubilized HRPO in solution. The soluble HRPO catalyzed the oxidation of guaiac by hydrogen peroxide, producing a blue color. Hence, blue color formation on the guaiac layered sheets provides a convenient method for detecting aspartic protease or pepsin.

Neither BSA nor buffer have aspartic protease activity. Hence, Sigmacell® 20 bound Kappa-Casein were not hydrolyzed, and soluble, active HRPO was not released from the support. Centriflgation sedimented Sigmacell® 20 bound HRPO, leaving no aspartic protease-solubilized HRPO in solution. The oxidation of guaiac by hydrogen peroxide was not catalyzed, and a barely detectable blue color formed.

EXPERIMENT IX

This experiment is an example of the release of HRPO from [SIGMACELL® 20-HEMOGLOBIN-HRPO] or [SIGMACELL® 20-MYOGLOBIN-HRPO] by aspartic protease released into Candida albicans culture.

A. MATERIALS: (ALDEHYDE ACTIVATED SIGMACELL® 20) (HRPO ALDEHYDE COUPLING METHOD)
1. Aldehyde activated Sigmacell® 20 (PREPARATION G) was first derivatized with covalently bound hemoglobin or myoglobin (PREPARATION H) and subsequently labeled with HRPO aldehyde (PREPARATIONS D AND F)
2. Aspartic Protease producing Candida albicans (ATCC 28366) culture propagated and grown in liquid culture as described in Journal of General Microbiology, (1983) 129: 431–438.
3. Guaiac layered sheets (PREPARATION S)
4. Buffers and solutions
   a. 20 mM hydrogen peroxide
   b. 500 mM MES buffer, pH 6.0

B. PROCEDURES 10 mg (wet weight) [Sigmacell® 20Protein-HRPO] conjugate were suspended in 300 microliters of either Candida albicans culture containing secreted aspartic protease, or 300 microliters of the same Candida albicans culture which had been boiled for 20 minutes to inactivate the aspartic protease. The mixture was rotated for 15 minutes at room temperature, and the suspension centrifuged to sediment the solid conjugate and Candida albicans cells.

Eighty microliters of the clear supernatant were mixed with 10 microliters of hydrogen peroxide solution and 10 microliters of MES buffer. Twenty microliters of each solution were added to surface of a guaiac layered sheet, and the sheet examined for formation of a blue color.

| COLOR SCORE | INTERPRETATION |
|---|---|
| 0 | NO VISIBLE BLUE COLOR FORMATION |
| +/− | POSSIBLE FAINT BLUE COLOR |
| 0.25 | FAINTEST BLUE COLOR DETECTABLE VISUALLY |
| 0.5 | DISTINCT BLUE COLOR |
| 1.0 | DARK BLUE COLOR |
| 2.0 | DARKEST BLUE COLOR POSSIBLE IN TEST SYSTEM |

C. RESULTS

A dark blue color formed on the guaiac layered sheet in the area to which *Candida albicans* treated Sepharose-protein-HRPO was added. No color was seen in the area to which boiled-culture treated Sepharose-protein-HRPO was added.

| ENZYME SOURCE | COLOR SCORE |
|---|---|
| *Candida Albicans* culture | 1.5 |
| Boiled culture | 0 |

D. INTERPRETATION

Aspartic protease secreted into the growth medium by *Candida albicans* cells hydrolyzed Sigmacell® 20 bound protein, releasing soluble, active HRPO. Centrifugation sedimented Sepharose bound HRPO, leaving only aspartic protease-solubilized HRPO in solution. The soluble HRPO catalyzed the oxidation of guaiac by hydrogen peroxide, producing a blue color. Hence, blue color formation on the guaiac layered sheets provides a convenient method for detecting aspartic protease.

Boiling the culture inactivated aspartic protease secreted into the growth medium by *Candida albicans* cells. Hence, Sigmacell® 20 bound protein was not hydrolyzed, and soluble, active HRPO was not released from the support. Centrifugation sedimented Sigmacells bound HRPO, leaving no aspartic protease-solubilized HRPO in solution. The oxidation of guaiac by hydrogen peroxide was not catalyzed, and a barely detectable blue color formed. Release of HRPO from the support was not simply the result of non-specific release of HRPO by salts or other components present in the growth medium.

EXPERIMENT X

This example is an example of the release of HRPO from [POLYMERIC DIALDEHYDE-KAPPA-CASEIN-HRPO] by pepsin and aspartic protease from *Aspergillus saitoi*.

A. MATERIALS: (POLYMERIC DIALDEHYDE) (HRPO HYDRAZIDE COUPLING METHOD)

1. Commercial polymeric dialdehyde from Sigma Chemical Co. allowed to react with Kappa-Casein-HRPO (hydrazide method) (PREPARATIONS B and L)
2. Test Solutions: a. Commercially available Aspartic Protease from *Aspergillus saitoi* (30 mg/mL, 0.6 units/mg); b. pepsin (1 mg/mL, 2900 units/mg); and c. Bovine Serum Albumin (BSA)(2 mg/mL in water) (all purchased from Sigma Chemical Co.)
3. Guaiac impregnated paper in the form of commercially available Hemoccult® slides
4. Buffers and solutions
   a. 0.02% (v/v) hydrogen peroxide in 200 mM phosphate buffer, pH 7.0
   b. 100 mM acetate buffer, pH 4.0

B. PROCEDURES 40 mg (wet weight) [POLYMERIC DIALDEHYDE-KAPPA-CASEIN-HRPO] conjugate were suspended in 75 microliters acetate buffer, pH 4.0 and 25 microliters of test solution were added. The suspension was incubated at room temperature for 15 minutes and centrifuged to remove the solid phase conjugate. Five microliters of the supernatant were added to a guaiac slide, followed by five microliters of hydrogen peroxide solution.

| COLOR SCORE | INTERPRETATION |
|---|---|
| 0 | NO VISIBLE BLUE COLOR FORMATION |
| +/− | POSSIBLE FAINT BLUE COLOR |
| 0.25 | FAINTEST BLUE COLOR DETECTABLE VISUALLY |
| 0.5 | DISTINCT BLUE COLOR |
| 1.0 | DARK BLUE COLOR |
| 1.5 | BLUE COLOR BETWEEN 1.0 AND 2.0 IN INTENSITY |
| 2.0 | DARKEST BLUE COLOR POSSIBLE IN TEST SYSTEM |

C. RESULTS

A dark blue color formed on the guaiac impregnated sheet in the area to which supernatant samples containing Aspartic Protease from *Aspergillus saitoi* or pepsin were added. Only a very faint color was seen in the area to which supernatant aliquots after BSA (2.0 mg/mL) or buffer were added.

| ENZYME SOURCE | COLOR SCORE |
|---|---|
| Aspartic Protease | 2.0 |
| Pepsin | 2.0 |
| BSA | +/− |
| Buffer | +/− |

D. INTERPRETATION

Active *Aspergillus saitoi* aspartic protease and porcine pepsin hydrolyzed polymeric dialdehyde bound Kappa-Casein, releasing soluble, active HRPO. Centrifugation sedimented polymeric dialdehyde bound HRPO, leaving only enzyme solubilized HRPO in solution. The soluble HRPO catalyzed the oxidation of guaiac by hydrogen peroxide, producing a blue color. Hence, blue color formation on the guaiac layered sheets provides a convenient method for detecting aspartic protease or pepsin.

Neither BSA nor buffer have aspartic protease activity. Hence, polymeric dialdehyde bound Kappa-Casein were not hydrolyzed, and soluble, active HRPO was not released from the support. Centrilugation sedimented polymeric dialdehyde bound HRPO, leaving no aspartic protease-solubilized HRPO in solution. The oxidation of guaiac by hydrogen peroxide was not catalyzed, and a barely detectable blue color formed.

EXPERIMENT XI

This experiment involves the release of HRPO from [POLYMERIC DIALDEHYDE-MYOGLOBIN-HRPO] by aspartic protease from *Candida albicans*.

A. MATERIALS: (POLYMERIC DIALDEHYDE)(HRPO ALDEHYDE COUPLING METHOD)

1. Commercial polymeric dialdehyde from Sigma Chemical Co. allowed to react with myoglobin (PREPARATION N) and subsequently with HRPO aldehyde (PREPARATION N).

2. Aspartic Protease producing *Candida albicans* (ATCC 28366) culture propagated and grown in liquid culture as described in *Journal of General Microbiology*, (1983) 129: 431–438.
3. Guaiac layered sheets (PREPARATION S)
4. Buffers and solutions
   1. 20 mM hydrogen peroxide
   2. 500 mM MES buffer, pH 6.0

B. PROCEDURES 10 mg (wet weight) [Polymeric Dialdehyde-Myoglobin-HRPO] conjugate were suspended in 300 microliters of either *Candida albicans* culture containing secreted aspartic protease, or 300 microliters of the same *Candida albicans* culture which had been boiled for 20 minutes to inactivate the aspartic protease. The mixture was rotated for 20 minutes at room temperature, and the suspension centrifuged to sediment the solid conjugate and *Candida albicans* cells.

Eighty microliters of the clear supernatant were mixed with 10 microliters of hydrogen peroxide solution and 10 microliters of MES buffer. Twenty microliters of each solution were added to surface of a guaiac layered sheet, and the sheet examined for formation of a blue color.

| COLOR SCORE | INTERPRETATION |
| --- | --- |
| 0 | NO VISIBLE BLUE COLOR FORMATION |
| +/− | POSSIBLE FAINT BLUE COLOR |
| 0.25 | FAINTEST BLUE COLOR DETECTABLE VISUALLY |
| 0.5 | DISTINCT BLUE COLOR |
| 1.0 | DARK BLUE COLOR |
| 1.5 | BLUE COLOR BETWEEN 1.0 AND 2.0 IN INTENSITY |
| 2.0 | DARKEST BLUE COLOR POSSIBLE IN TEST SYSTEM |

C. RESULTS

A dark blue color formed on the guaiac layered sheet in the area to which *Candida albicans* treated polymeric dialdehyde-myoglobin-HRPO was added. No color was seen in the area to which boiled culture treated dialdehyde-myoglobin-HRPO was added.

| ENZYME SOURCE | COLOR SCORE |
| --- | --- |
| *Candida albicans* culture | 1.5 |
| Boiled culture | 0 |

D. INTERPRETATION

Active aspartic protease secreted into the growth medium by *Candida albicans* cells hydrolyzed polymeric dialdehyde-myoglobin, releasing soluble, active HRPO. Centrifugation sedimented polymeric dialdehyde bound HRPO, leaving only aspartic protease-solubilized HRPO in solution. The soluble HRPO catalyzed the oxidation of guaiac by hydrogen peroxide, producing a blue color. Hence, blue color formation on the guaiac layered sheets provides a convenient method for detecting aspartic protease.

Boiling the culture inactivated aspartic protease secreted into the growth medium by *Candida albicans* cells. Hence, polymeric dialdehyde bound myoglobin was not hydrolyzed, and soluble, active HRPO was not released from the support. Centrifugation sedimented polymeric dialdehyde bound HRPO, leaving no aspartic protease-solubilized HRPO in solution. The oxidation of guaiac by hydrogen peroxide was not catalyzed, and a barely detectable blue color formed. Release of HRPO from the support was not simply the result of non specific release of HRPO by salts or other components present in the growth medium.

EXPERIMENT XII

This experiment involves the release of HRPO from [SEPHAROSE 6 MB-KAPPA-CASEIN-HRPO] by vaginal fluid specimens:
1. Normal vaginal fluid
2. Normal vaginal fluid to which *Candida albicans* culture had been added
3. Vaginal fluid from women with clinically diagnosed vulvovaginal candidiasis A. MATERIALS: (COMMERCIAL CYANOGEN BROMIDE ACTIVATED SEPHAROSE 6 MB) (HRPO HYDRAZIDE COUPLING METHOD)

1. Sepharose 6 MB-Kappa-Casein-HRPO conjugate (PREPARATION C)
2. Vaginal fluid samples obtained on standard Dacron swabs. The specimens were frozen until immediately prior to use. The specimens were thawed, and centrifuged in specially adapted tubes to permit extraction of undiluted vaginal fluid from the swab. The entire specimen from each swab was tested. Where necessary, distilled water was added to the specimen to produce a final volume of 75 microliters. Where indicated, 25 microliters of a *Candida albicans* culture (See, e.g., Experiment I) were added to vaginal fluid specimens obtained from women without clinical vulvovaginal candidiasis.
3. Guaiac impregnated filter paper (commercial Hemoccult® test slides)
4. Buffers and solutions
   a. 6 mM hydrogen peroxide
   b. 250 mM glycylglycine buffer, pH 3.0

B. PROCEDURES 30 mg (wet weight) [Sepharose-Kappa-Casein-HRPO] conjugate were suspended in 75 microliters of treated or untreated vaginal fluid. The suspensions were incubated at room temperature for 15 minutes, and the suspension centrifuged to sediment the solid conjugate and other debris.

Five microliters of the clear supernatants were added to the guaiac-impregnated paper, followed by 5 microliters of hydrogen peroxide solution, and the sheets were examined for formation of a blue color.

| COLOR SCORE | INTERPRETATION |
| --- | --- |
| 0 | NO VISIBLE BLUE COLOR FORMATION |
| +/− | POSSIBLE FAINT BLUE COLOR |
| 0.25 | FAINTEST BLUE COLOR DETECTABLE VISUALLY |
| 0.5 | DISTINCT BLUE COLOR |
| 1.0 | DARK BLUE COLOR |
| 2.0 | DARKEST BLUE COLOR POSSIBLE IN TEST SYSTEM |

C. RESULTS

A dark blue color formed on the guaiac impregnated paper in the area to which vaginal fluid supernatant from women infected wiffi vulvovaginal candidiasis was added. No color was formed in the areas of the guaiac impregnated paper to which vaginal fluid supernatant from control women was added. A strong blue color also formed on the guaiac impregnated paper in the area to which vaginal fluid supernatant from normal women which had been supplemented with medium from a growing *Candida albicans* culture was added.

| SPECIMEN NO. | DIAGNOSIS | COLOR SCORE |
|---|---|---|
| 7757 | CANDIDIASIS | 2.0 |
| 7701 | CANDIDIASIS | 2.0 |
| 7749 | CANDIDIASIS | 2.0 |
| 7760 | CANDIDIASIS | 2.0 |
| 7753 | CANDIDIASIS | 2.0 |
| 7795 | CANDIDIASIS | 2.0 |
| 7779 | CANDIDIASIS | 2.0 |
| 7799 | CANDIDIASIS | 2.0 |
| 7768 | NORMAL | 1.0 |
| 7770 | NORMAL | 0.0 |
| 7744 | NORMAL | 0.0 |
| 7745 | NORMAL | 0.0 |
| 7750 | NORMAL | 0.0 |
| 7761 | NORMAL | 0.0 |
| 0001 | NORMAL | 0.0 |
| 0001 | NORMAL + Candida culture | 2.0 |
| 7747 | NORMAL + Candida culture | 2.0 |
| 7748 | NORMAL + Candida culture | 1.0 |
| 7750 | NORMAL + Candida culture | 2.0 |
| 7756 | NORMAL + Candida culture | 2.0 |

D. INTERPRETATION

Vaginal fluid from women with proven clinical vulvovaginal candidiasis contained aspartic protease which hydrolyzed Sepharose 6 MB-bound Kappa-Casein, at pH 3.0 in 15 minutes at room temperature, releasing soluble, active HRPO. Centrifugation sedimented Sepharose 6 MB-bound HRPO, leaving only released, solubilized HRPO in solution. The soluble HRPO catalyzed oxidation of the commercial Hemoccult® slides, producing a blue color. Hence, blue color formation on the Hemoccult® slides provides a rapid and convenient method for detecting Candida-derived aspartic protease in vaginal fluid, and hence, vulvovaginal candidiasis.

Vaginal fluid from normal women without vulvovaginal candidiasis did not contain aspartic protease, and failed to hydrolyze Sepharose 6 MB-bound Kappa-casein, at pH 3.0 in 15 minutes at room temperature, and failed to release soluble, active HRPO. Centrifugation sedimented Sepharose 6 MB-bound HRPO, leaving no released, solubilized HRPO in solution. Lacking the HRPO catalyst, no oxidation of the commercial Hemoccult® slides occurred and no blue color was produced. Hence, lack of a blue color formation on the Hemoccult® slides provides a rapid and convenient method for detecting normal women lacking Candida-derived aspartic protease in vaginal fluid and, hence, women who did not have vulvovaginal candidiasis.

Finally, when medium from a *Candida albicans* culture was added to vaginal fluid from normal women without vulvovaginal candidiasis hydrolysis of Sepharose 6 MB-bound Kappa-Casein occurred at pH 3.0 in 15 minutes at room temperature, and soluble, active HRPO was released. Centrifugation sedimented Sepharose 6 MB-bound HRPO, leaving released, solubilized HRPO in solution. The soluble HRPO catalyzed oxidation of commercial Hemoccult® slides by hydrogen peroxide and produced a blue color. Hence, blue color formation on the Hemoccult® slides demonstrates that aspartic protease released into growth medium by *Candida albicans* cells can readily be detected rapidly and conveniently even when added to vaginal fluid from normal women.

EXPERIMENT XIII

This experimnent involves the release of HRPO from [EUPERGIT® C-MYOGLOBIN-HRPO] and [SIGMACELL® 20-MYOGLOBIN-HRPO] by vaginal fluid specimens.

1. Normal vaginal fluid
2. Vaginal fluid from women with clinically diagnosed vulvovaginal candidiasis A. MATERIALS: (CYANOGEN BROMIDE ACTIVATED SIGMACELL® 20-MYOGLOBIN-HRPO—PREPARATIONS A AND I) AND (EUPERGIT® C-MYOGLOBIN-HRPO—PREPARATION Q) (HRPO ALDEHYDE COUPLING METHOD)

1. Finely ground oxirane acrylic beads coupled to Myoglobin-HRPO Aldehyde (PREPARATION Q)
2. Sigmacell® 20 (cyanogen bromide activated, PREPARATION A) coupled to Myoglobin-HRPO Aldehyde (PREPARATION I)
3. Vaginal fluid samples obtained on standard Dacron swabs. The specimens were frozen until immediately prior to use. The specimens were thawed, and centrifuged in specially adapted tubes to permit extraction of undiluted vaginal fluid from the swab. The entire specimen from each swab was tested.
4. Guaiac impregnated filter paper (commercial Hemoccult® test slides)
5. Buffers and solutions
   a. 6 mM hydrogen peroxide
   b. 250 mM glycylglycine buffer, pH 3.0
   c. 1.0 M acetate buffer, pH 4.0

B. PROCEDURES 20 mg (wet weight) of Eupergit®-bound myoglobin-HRPO conjugate were suspended in the undiluted vaginal fluid and 10 microliters of 1 M acetate buffer. The suspensions were incubated at room temperature for 10 minutes, and the suspension centrifuged to sediment the solid conjugate and other debris.

Five microliters of the clear supernatant were added to the guaiac-impregnated paper, followed by 5 microliters of hydrogen peroxide solution, and the sheets were examined for formation of a blue color.

20 mg (wet weight) of Sigmacell® 20-bound myoglobin-HRPO conjugate were suspended in undiluted vaginal fluid and 10 microliters of 250 mM acetate buffer. The suspensions were incubated at room temperature for 15 minutes, and the suspension centrifuged to sediment the solid conjugate and other debris.

Five microliters of the clear supernatant were added to the guaiac-impregnated paper, followed by 5 microliters of hydrogen peroxide solution, and the sheets were examined for formation of a blue color.

| COLOR SCORE | INTERPRETATION |
|---|---|
| 0 | NO VISIBLE BLUE COLOR FORMATION |
| +/− | POSSIBLE FAINT BLUE COLOR |
| 0.25 | FAINTEST BLUE COLOR DETECTABLE VISUALLY |
| 0.5 | DISTINCT BLUE COLOR |
| 1.0 | DARK BLUE COLOR |
| 2.0 | DARKEST BLUE COLOR POSSIBLE IN TEST SYSTEM |

C. RESULTS

A dark blue color formed on the guaiac impregnated paper in the area to which vaginal fluid from women infected with vulvovaginal candidiasis was added. No color was formed in the areas of the guaiac impregnated paper to which vaginal fluid from control was added.

| SPECIMEN NO. | SCORE | DIAGNOSIS | SUBSTRATE | COLOR |
|---|---|---|---|---|
| 7823 | | CANDIDIASIS | Sigmacell® | 2.0 |
| 7824 | | CANDIDIASIS | Sigmacell® | 2.0 |
| 7844 | | CANDIDIASIS | Sigmacell® | 2.0 |
| 7848 | | CANDIDIASIS | Sigmacell® | 2.0 |
| 7820 | | CONTROL | Sigmacell® | 0.0 |
| 7821 | | CONTROL | Sigmacell® | 0.0 |
| 7826 | | CONTROL | Sigmacell® | 0.0 |
| 7831 | | CONTROL | Sigmacell® | 0.0 |
| 7891 | | CANDIDIASIS | EUPERGIT® C | 2.0 |
| 7921 | | CANDIDIASIS | EUPERGIT® C | 2.0 |
| 7914 | | CONTROL | EUPERGIT® C | +/− |
| 7915 | | CONTROL | EUPERGIT® C | 0.0 |

D. INTERPRETATION

Active aspartic protease secreted into the vaginal fluid of women with clinical candidiasis by *Candida albicans* cells hydrolyzed both Sigmacell® 20-bound protein and Eupergit®-bound protein, releasing soluble, active HRPO. Centrifugation sedimented polymer-bound HRPO, leaving only aspartic protease-solubilized HRPO in solution. The soluble HRPO catalyzed the oxidation of guaiac by hydrogen peroxide, producing a blue color. Hence, blue color fonmation on the guaiac-impregnated paper provides a convenient and effective method for detecting active aspartic protease in vaginal fluid, and thereby, vulvovaginal candidiasis.

Active aspartic protease is not found in the vaginal fluid of control women, i.e., those without clinical candidiasis. Hence, vaginal fluid specimens from control women failed to hydrolyze polymer-bound protein, and failed to release soluble, active HRPO from either support. Centrifugation sedimented polymer bound HRPO, leaving no aspartic protease-solubilized HRPO in solution. Lacking HRPO, the supernatant from control specimens failed to catalyze the oxidation of guaiac by hydrogen peroxide, and failed to produce a blue color. Hence, failure to form a blue color on the guaiac-impregnated paper provides a convenient method for identifying women who were not infected with vulvovaginal *Candida albicans*.

EXPERIMENT XIV

This experiment involves the differential hydrolytic activity of several microbial proteases on [Sigmacell®-Myoglobin-HRPO].

A. MATERIALS
1. [Sigmacell®-Myoglobin-HRPO] (PREPARATIONS E and F).
2. Aspartic protease producing *Candida albicans* (ATCC 28366) culture.
3. *Trichomonas vaginalis* (ATCC 3001) culture.
4. *Mobiluncus curtisii* cell suspension (ATCC 35241) in saline solution.
5. Buffers and solutions.
   a. 0.02% hydrogen peroxide solution
   b. Potassium phosphate buffer pH 7.5, 300 mM
   c. Sodium acetate buffer pH 4.0, 100 mM.
6. Guaiac impregnated paper (commercial Hemoccult® slides).

B. PROCEDURE.

Twenty milligrams of substrate [Sigmacell®-Myoglobin-HRPO] were suspended in 75 microliters of the appropriate buffer (see table below), followed by addition of 25 microliters of cell culture/suspension. The reaction was incubated between 10–30 mins after which the sample was centrifuged to remove solid phase conjugated substrate and cell debris. Five microliters of the reaction supernatant were added to the guaiac slide and developed with 5 microliters of hydrogen peroxide solution. The reaction conditions and color development are reported in the table that follows.

| Enzyme Source (Cell Cultures) | pH of Incubation | Time of incubation | Color Score |
|---|---|---|---|
| *Candida albicans* | 4.0 | 10 min | 2.0 |
| *Candida albicans* | 7.5 | 30 min | 0.0 |
| Boiled *Candida albicans* | 4.0 | 30 min | 0.0 |
| Boiled *Candida albicans* | 7.5 | 30 min | 0.0 |
| *Mobiluncus curtisii* | 4.0 | 30 min | 0.0 |
| *Mobiluncus curtisii* | 7.5 | 30 min | 0.0 |
| Boiled *Mobiluncus curtisii* | 4.0 | 30 min | 0.0 |
| Boiled *Mobiluncus curtisii* | 7.5 | 30 min | 0.0 |
| *Trichomonas vaginalis* | 4.0 | 30 min | 0.25 |
| *Trichomonas vaginalis* | 7.5 | 30 min | 2.0 |
| Boiled *T. vaginalis* | 4.0 | 30 min | 0.0 |
| Boiled *T. vaginalis* | 7.5 | 30 min | 0.0 |
| Buffer | 4.0 | 30 min | 0.0 |
| Buffer | 7.5 | 30 min | 0.0 |

D. INTERPRETATION

HRPO is not released from the solid support by 300 mM phosphate buffer at pH 7.5 or by 100 mM acetate buffer at pH 4.0 over a 30 minute incubation interval at room temperature. Similarly, Boiled suspensions of *Candida albicans*, *Trichomonas vaginalis* or *Mobiluncus curtisii* do not release HRPO at pH 7.5 or 4.0 over a 30 minute incubation at room temperature. A *Candida albicans* culture, however releases HRPO from the solid support at pH 4.0 in 10 minutes, but fails to release HRPO at pH 7.5, even over a 30 minute incubation period. This is consistent with the established pH profile of the *Candida albicans* aspartic protease, which is active at low pH, but poorly active or inactive at high pH. Conversely, a *T. vaginalis* culture readily releases HRPO from the solid support at pH 7.4 over a 30 minute incubation interval, but releases barely detectable quantities of HRPO at pH 4.0. This behavior is also consistent with the known pH profile of the *T. vaginalis* thiol proteases (i.e., active at high pH, but much less active or inactive at low pH). Finally, *Mobiluncus curtisii*, which is not known to excrete proteases, fails to release HRPO at either pH 4.0 or pH 7.5 even over a 30 minute incubation interval.

Hence, by performing the tests under different pH conditions, it is possible to differentiate between the three microbes: only *Candida albicans* will cause color formation in 10 minutes at room temperature at pH 4.0; only *Trichomonas vaginalis* will cause color formation at pH 7.5 in 30 minutes, and; *Mobiluncus curtisii* will not cause color formation in 30 minutes at either pH 7.5 or 4.0.

EXPERIMENT XV

This experiment involves the activity of various proteases and their inhibitors on the substrate [Eupergit® C-Myoglobin-HRPO].

A. MATERIALS
1. Pulverized [Eupergit® C-Myoglobin-HRPO] (PREPARATION Q).
2. Commercially available aspartic protease from Sigma Chemical Co. (Type XMII, from *Aspergillus saitoi*, 0.6 units/mg activity) 40 mg/ml.
3. Trypsin (serine protease) from bovine pancreas (2900 units/mg activity), obtained from U.S. Biochemicals, 2 mg/ml.

4. Papain (thiol protease) from papaya latex (12 units/mg activity) from Sigma Chemical Co., 2 mg/ml.
5. Aspartic protease producing *Candida albicans* culture (ATCC 28366)
6. Tosyl lysine chloromethyl ketone (TLCK) hydrochloride 50 mM in ethanol from Sigma Chemical Co.
7. Pepstatin A from a microbial source, obtained from Sigma Chemical Co., 2 mg/ml in ethanol.
8. Buffers and solutions.
   a. Potassium phosphate buffer pH 7.0, 200 mM.
   b. Potassium phosphate buffer pH 7.4, 100 mM.

| COLOR SOURCE | INTERPRETATION |
|---|---|
| 0 | NO VISIBLE BLUE COLOR FORMATION |
| +/− | POSSIBLE FAINT BLUE COLOR |
| 0.25 | FAINTEST BLUE COLOR DETECTABLE VISUALLY |
| 0.5 | DISTINCT BLUE COLOR |
| 1.0 | DARK BLUE COLOR |
| 2.0 | DARKEST BLUE COLOR POSSIBLE IN TEST SYSTEM |

C. RESULTS

No color formed when the reaction supernatant from tubes incubated with buffer at pH 4.0 or pH 7.5 for 30 minutes was added to guaiac slides and developed with hydrogen peroxide. A similar result was seen (i.e., no color formation) with boiled cultures from *Candida albicans* (pH 4.0 and 7.5), *Trichomonas vaginalis* (pH 4.0 and 7.5) or *Mobiluncus curtisii* (pH 4.0 and 7.5). *Candida albicans* culture produced a strong blue color after a 10 minute incubation at pH 4.0, but not at pH 7.5 even after a 30 minute incubation. *Trichomonas vaginalis* produced a strong blue color after a 30 minute incubation at pH 7.5, but only a barely detectable color after a 30 minute incubation at pH 4.0. *Mobiluncus Curtisii* culture produced no blue color in 30 minutes at either pH 4.0 or 7.5.
   c. Sodium acetate buffer pH 4.0, 100 mM.
   d. 0.02% Hydrogen peroxide solution.
   e. Absolute ethanol.
9. Guaiac impregnated paper (commercial Hemoccult® slides).

B. PROCEDURE.

This assay is set up in two parts. The first is to determine the activity of the different proteases on the substrate [Eupergit® C-Myoglobin-HRPO]. The enzymes and controls (enzymes boiled for 15 min) are incubated with 20 mg of substrate and buffers (see quantities in table below) for 15 minutes prior to assay.

In the second part, the enzymes are preincubated with their respective inhibitors and appropriate buffers for 15 mins. These are then added to the substrate and incubated at room temp for fiurther 15 mins.

In both cases, the reaction mixture is centrifuged to remove solid phase conjugate. The supernatant (5 µl) is added to Hemoccult® slides and developed with 5 µl of hydrogen peroxide.

| COLOR SOURCE | INTERPRETATION |
|---|---|
| 0 | NO VISIBLE BLUE COLOR FORMATION |
| +/− | POSSIBLE FAINT BLUE COLOR |
| 0.25 | FAINTEST BLUE COLOR DETECTABLE VISUALLY |
| 0.5 | DISTINCT BLUE COLOR |
| 1.0 | DARK BLUE COLOR |
| 2.0 | DARKEST BLUE COLOR POSSIBLE IN TEST SYSTEM |

C. RESULTS

1. PART I: The reaction supernatants from tubes containing Buffer alone at either pH 4.0 or pH 7.5 produced the only faintest color detectable when added to guaiac slides and developed with hydrogen peroxide developer. The same result was seen with reaction supernatants from tubes containing boiled trypsin at pH 7.4, boiled Candida culture at pH 4.0, and boiled papain at pH 7.4. A strong blue color was formed with unboiled trypsin at pH 7.4, unboiled Candida culture at pH 4.0, and unboiled papain at pH 7.0.

2. PART II: TLCK, a protease inhibitor capable of inhibiting both serine and thiol type proteases inhibits color formation by both trypsin (a serine protease) and papain (a thiol protease). Pepstatin, a known inhibitor of aspartic proteases inhibits color formation by the *Candida albicans* aspartic protease.

TABLE

PART 1

| Enzyme Source (vol. = 25 µl) | Buffer (vol. = 75 µl) | Color score |
|---|---|---|
| Trypsin | pH 7.4 | 2.0 |
| Trypsin (boiled) | pH 7.4 | 0.25 |
| Candida culture | pH 4.0 | 1.5 |
| Candida boiled | pH 4.0 | 0.25 |
| Papain | pH 7.0 | 1.0 |
| Papain (boiled) | pH 7.4 | 0.25 |
| | buffers only | 0.25 |

TABLE

PART 2

| Enzyme | Inhibitor Solution | Ethanol (Control) | Buffer pH, Vol. | Color Score |
|---|---|---|---|---|
| Trypsin | TLCK (10 µl) | — | 7.4, 65 µl | 1.0 |
| Trypsin | — | — | 7.4, 75 µl | 2.0 |
| Papain | TLCK (25 µl) | 25 µl | 7.0, 50 µl | 0.5 |
| Papain | — | — | 7.0, 50 µl | 1.0 |
| Aspartic protease | Pepstatin (25 µl) | — | 4.0, 50 µl | 0.5 |
| Aspartic protease | — | 25 µl | 4.0, 50 µl | 1.5 |

D. INTERPRETATION

Trypsin, a serine protease hydrolyzed the solid phase substrate at pH 7.4, releasing soluble HRPO which catalyzed blue color formation on developed guajac slides. The same was true for the *Candida albicans* aspartic protease at pH 4.0, and papain, a thiol protease at pH 7.0. Boilin prevented HRPO release by each enzyme. Hence, each of the three different enzyme types was capable of hydrolytic release of soluble HRPO from the support under the appropriate reaction conditions. Neither buffers nor heat inactivated enzymes released soluble HRPO, indicating that HRPO release was not simply a non specific release caused by salts, etc. in the growth medium or incubation mixture.

TLCK, a protease inhibitor capable of inhibiting both serine and thiol type proteases inhibits color formation by both trrpsin (a serine protease) and papain (a thiol protease).

Pepstatin, a known inhibitor of aspartic proteases inhibits color formation by the *Candida albicans* aspartic protease. Hence, by performing incubations in the presence of known specific enzyme inhibitors or inhibitors of specific classes of enzymes, specificity of hydrolase detection can be attained.

The foregoing is offered for purposes of illustration. It will be readily apparent to those skilled in the art that the operating conditions, materials, procedural steps and other parameters of the methods and test devices described herein may be further modified or substituted in ways without departing from the spirit and scope of the invention.

What is claimed is:

1. A method for assaying for the presence of an enzymatically active hydrolase in a sample, said method comprising:
   (a) placing said sample in a test device such that said sample contacts a first solid support in said test device, said first solid support having a reporter enzyme in dry form and covalently attached thereto in such a manner whereby said reporter enzyme is released upon action of said hydrolase, and such that said sample simultaneously contacts a second solid support having immobilized thereon in dry form an indicator, said indicator being one which is susceptible to a detectable change upon action of said reporter enzyme but not susceptible to said change in the absence of said sample; and
   (b) observing whether said indicator undergoes a detectable change, said detectable change being an indication of the presence of said enzymatically active hydrolase in said sample.

2. A method in accordance with claim 1 wherein said hydrolase is selected from the group consisting of proteases, peptidases, lipases, nucleases, homo-oligosaccharidases, hetero-oligosaccharidases, homo-polysaccharidases, hetero-polysaccharidases, phosphatases, sulfatases, neuraminidases and esterases.

3. A method in accordance with claim 2 wherein said hydrolase is a protease selected from the group consisting of aspartic proteases, serine proteases, thiol proteases, metallo proteases, acid proteases and alkaline proteases.

4. A method in accordance with claim 3 wherein said protease is an aspartic protease.

5. A method in accordance with claim 3 wherein said protease is a thiol protease.

6. A method in accordance with claim 3 wherein said protease is a serine protease.

7. A method in accordance with claim 2 wherein said hydrolase is selected from the group consisting of homo-oligosaccharidases, hetero-oligosaccharidases, homo-polysaccharidases and hetero-polysaccharidases.

8. A method in accordance with claim 7 wherein said hydrolase is selected from the group consisting of chitinase, cellulase, amylase and lysozyme.

9. A method in accordance with claim 1 wherein said reporter enzyme is a signal generating enzyme not subject to inactivation by any agent in said sample, including inactivating hydrolysis by any hydrolase activity present in said sample.

10. A method in accordance with claim 9 wherein said reporter enzyme is selected from the group consisting of peroxidases, phosphatases, oxidoreductases, dehydrogenases, transferases, isomerases, kinases, reductases, deaminases, catalases, urease and glucuronidase.

11. A method in accordance with claim 10 wherein said reporter enzyme is a peroxidase.

12. A method in accordance with claim 11 wherein said peroxidase is horseradish peroxidase.

13. A method in accordance with claim 1 wherein said first and second solid supports are independently selected from the group consisting of cellulose, agarose, dextran, polyacrylate, and polyacrylamide.

14. A method in accordance with claim 1 wherein said first and second solid supports are independently selected from the group consisting of chitin, sepharose, oxirane acrylic beads, polymeric dialdehyde, starch, collagen, keratin, elastin, bovine hide powder, bacterial cell wall peptidoglycan, nylon, polyethylene terephthalates, polycarbonates and controlled pore glass.

15. A method in accordance with claim 1 wherein said reporter enzyme is colavently attached to said first solid support through a linker molecule which is a substrate for said hydrolase.

16. A method in accordance with claim 15 wherein said linker molecule is selected from the group consisting of proteins, carbohydrates, lipids, peptides, esters and nucleic acids.

17. A method in accordance with claim 16 wherein said linker molecule is a protein selected from the group consisting of azocasein, casein, κ-casein, immunoglobulins, hemoglobin, myoglobin, albumin, elastin, keratin and collagen.

18. A method in accordance with claim 1 wherein said indicator is a visual indicator.

19. A method in accordance with claim 18 wherein said visual indicator is a chromogenic indicator.

20. A method in accordance with claim 19 wherein said chromogenic indicator is an indicator for peroxidative activity.

21. A method in accordance with claim 20 wherein said chromogenic indicator is comprised of a hydroperoxide and a chromogen selected from the group consisting of guaiac, 2-2'-azino-bis(3-ethyl-benzthiazoline-6-sulfonic acid), tetramethylbenzidine, phenol, 4-aminoantipyrine, and 4,5-dihydroxynaphthalene-2,7-disulfonic acid.

22. A method in accordance with claim 1 wherein an inhibitor of a hydrolase other than said hydrolase being assayed for is added to increase specificity for said hydrolase.

23. A method for assaying for the presence of an enzymatically active hydrolase in a sample, said method comprising:
   (a) placing said sample in a device which contains first and second solid supports, said first solid support having a reporter enzyme covalently attached thereto in such a manner whereby said reporter enzyme is released upon action of said hydrolase, said second solid support, which is not in contact with said first solid support, having immobilized thereon an indicator, said indicator being one which is susceptible to a detectable change upon action of said reporter enzyme, said sample being placed in said device in such a manner that said sample contacts said first and second solid supports such that any reporter enzyme released by any hydrolase activity present in said sample is permitted to diffuse through said sample to said second solid support; and
   (b) observing whether said indicator undergoes a detectable change, said detectable change being an indication of the presence of said enzymatically active hydrolase in said sample.

24. A method in accordance with claim 23 wherein said hydrolase is selected from the group consisting of proteases, peptidases, lipases, nucleases, homo-oligosaccharidases, hetero-oligosaccharidases, homo-polysaccharidases, hetero-polysaccharidases, phosphatases, sulfatases, neuraminidases and esterases.

25. A method in accordance with claim 24 wherein said hydrolase is a protease selected from the group consisting of aspartic proteases, serine proteases, thiol proteases, metallo proteases, acid proteases and alkaline proteases.

26. A method in accordance with claim 25 wherein said protease is an aspartic protease.

27. A method in accordance with claim 24 wherein said hydrolase is selected from the group consisting of homo-oligosaccharidases, hetero-oligosaccharidases, homo-polysaccharidases, and hetero-polysaccharidases.

28. A method in accordance with claim 27 wherein said hydrolase is selected from the group consisting of chitinase, cellulase, amylase and lysozyme.

29. A method in accordance with claim 23 wherein said reporter enzyme is a signal generating enzyme not subject to inactivation by any agent in said sample, including inactivating hydrolysis by any hydrolase activity present in said sample.

30. A method in accordance with claim 29 wherein said reporter enzyme is selected from the group consisting of peroxidases, phosphatases, oxidoreductases, dehydrogenases, transferases, isomerases, kinases, reductases, deaminases, catalases, urease and glucuronidase.

31. A method in accordance with claim 30 wherein said reporter enzyme is a peroxidase.

32. A method in accordance with claim 31 wherein said peroxidase is horseradish peroxidase.

33. A method in accordance with claim 23 wherein said first and second solid supports are independently selected from the group consisting of cellulose, agarose, dextran, polyacrylate, and polyacrylamide.

34. A method in accordance with claim 23 wherein said first and second solid supports are independently selected from the group consisting of chitin, polymeric dialdehyde, starch, nylon, polyethylene terephthalates, polycarbonates and controlled pore glass.

35. A method in accordance with claim 23 wherein said reporter enzyme is covalently attached to said first solid support through a linker molecule which is a substrate for said hydrolase.

36. A method in accordance with claim 35 wherein said linker molecule is selected from the group consisting of proteins, carbohydrates, lipids, peptides, esters and nucleic acids.

37. A method in accordance with claim 36 wherein said linker molecule is a protein selected from the group consisting of azocasein, casein, κ-casein, immunoglobulins, hemoglobin, myoglobin, albumin, elastin, keratin and collagen.

38. A method in accordance with claim 23 wherein said indicator is a visual indicator.

39. A method in accordance with claim 38 wherein said visual indicator is a chromogenic indicator.

40. A method in accordance with claim 39 wherein said chromogenic indicator is an indicator for peroxidative activity.

41. A method in accordance with claim 40 wherein said chromogenic indicator is comprised of a hydroperoxide and a chromogen selected from the group consisting of guaiac, 2-2'-azino-bis(3-ethyl-benzthiazoline-6-sulfonic acid), tetramethylbenzidine, phenol, 4-aminoantipyrine, and 4,5-dihydroxynaphthalene-2,7-disulfonic acid.

42. A method in accordance with claim 41 wherein said chromogenic indicator is comprised of a hydroperoxide and guaiac.

43. A method in accordance with claim 23 wherein an inhibitor of a hydrolase other than said hydrolase being assayed for is added to increase specificity for said hydrolase.

44. A method for assaying for the presence of enzymatically active aspartic protease in a sample, said method comprising:
(a) placing said sample in a device which contains first and second solid supports, said first solid support being polyacrylate and having horseradish peroxidase covalently attached thereto through myoglobin which is a substrate for said aspartic protease, said second solid support, which is not in contact with said first solid support, being hydroxypropyl cellulose and having immobilized thereon a hydroperoxide and guaiac, a chromogenic substrate which undergoes a color change upon action of said horseradish peroxidase in the presence of said hydroperoxide, said sample being placed in said device in such a manner that said sample contacts said first and second solid supports such that any horseradish peroxidase released by any aspartic protease present in said sample is permitted to diffuse through said sample to said second solid support; and
(b) observing whether said guaiac undergoes a color change, said color change being an indication of the presence of said enzymatically active aspartic protease in said sample.

45. A method for detecting candidiasis by assaying for the presence of enzymatically active aspartic protease in a sample, said method comprising:
(a) contacting said sample with a first solid support, said first solid support having a reporter enzyme covalently attached thereto in such a manner whereby said reporter enzyme is released upon action of said aspartic protease;
(b) combining said sample with a second solid support, said second solid support having immobilized thereon an indicator, said indicator being one which is susceptible to a detectable change upon action of said reporter enzyme; and
(c) observing whether said indicator undergoes a detectable change, said detectable change being an indication of the presence of said enzymatically active aspartic protease in said sample and thus, candidiasis.

46. A method in accordance with claim 45 wherein said reporter enzyme is a signal generating enzyme not subject to inactivation by any agent in said sample, including inactivating hydrolysis by any hydrolase activity present in said sample.

47. A method in accordance with claim 45 wherein said first and second solid supports are independently selected from the group consisting of cellulose, agarose, dextran, polyacrylate, and polyacrylamide.

48. A method in accordance with claim 45 wherein said solid support is selected from the group consisting of chitin, sepharose, oxirane acrylic beads, polymeric dialdehyde, starch, collagen, keratin, elastin, bovine hide powder, bacterial cell wall peptidoglycan, nylon, polyethylene terephthalates, polycarbonates and controlled pore glass.

49. A method in accordance with claim 45 wherein said reporter enzyme is covalently attached to said first solid support through a linker molecule which is a substrate for said hydrolase.

50. A method in accordance with claim 49 wherein said linker molecule is selected from the group consisting of proteins and peptides.

51. A method in accordance with claim 50 wherein said protein is selected from the group consisting of azocasein, casein, κ-casein, immunoglobulins, hemoglobin, myoglobin, albumin, elastin, keratin and collagen.

52. A method in accordance with claim 45 wherein said indicator is a visual indicator.

53. A method in accordance with claim 54 wherein said visual indicator is a chromogenic indicator.

54. A method in accordance with claim 45 wherein the pH of said sample is from about 2.5 to about 5.0 to increase aspartic protease sensitivity and specificity.

55. A method in accordance with claim 45 wherein a protease inhibitor is added to increase specificity for aspartic protease activity.

56. A method in accordance with claim 55 wherein said protease inhibitor is selected from the group consisting of inhibitors of serine proteases, thiol proteases, metallo proteases and other non-aspartic proteases.

57. A method for detecting *Trichomonas vaginalis* by assaying for the presence of enzymatically active thiol protease in a sample, said method comprising:
  (a) contacting said sample with a first solid support, said first solid support having a reporter enzyme covalently attached thereto in such a manner whereby said reporter enzyme is released upon action of said thiol protease;
  (b) combining said sample with a second solid support having immobilized thereon an indicator, said indicator being one which is susceptible to a detectable change upon action of said reporter enzyme; and
  (c) observing whether said indicator undergoes a detectable change, said detectable change being an indication of the presence of said enzymatically active thiol protease in said sample and thus, *Trichomonas vaginalis*.

58. A method in accordance with claim 57 wherein said reporter enzyme is a signal generating enzyme not subject to inactivation by any agent in said sample, including inactivating hydrolysis by any hydrolase activity present in said sample.

59. A method in accordance with claim 57 wherein said first and second solid supports are independently selected from the group consisting of cellulose, agarose, dextran, polyacrylate, and polyacrylamide.

60. A method in accordance with claim 57 wherein said first and second solid supports are independently selected from the group consisting of chitin, sepharose, oxirane acrylic beads, polymeric dialdehyde, starch, collagen, keratin, elastin, bovine hide powder, bacterial cell wall peptidoglycan, nylon, polyethylene terephthalates, polycarbonates and controlled pore glass.

61. A method in accordance with claim 57 wherein said reporter enzyme is covalently attached to said first solid support through a linker molecule which is a substrate for said hydrolase.

62. A method in accordance with claim 61 wherein said linker molecule is selected from the group consisting of proteins and peptides.

63. A method in accordance with claim 62 wherein said protein is selected from the group consisting of azocasein, casein, κ-casein, immunoglobulins, hemoglobin, myoglobin, albumin, elastin, keratin and collagen.

64. A method in accordance with claim 57 wherein said indicator is a visual indicator.

65. A method in accordance with claim 64 wherein said visual indicator is a chromogenic indicator.

66. A method for assaying for the presence of an inhibitor of a target hydrolase in a sample, said method comprising:
  (a) contacting said sample with said target hydrolase and a first solid support, said first solid support having a reporter enzyme covalently attached thereto in such a manner whereby said reporter enzyme is released upon action of said target hydrolase if said target hydrolase is not inactivated by the presence of said inhibitor;
  (b) combining said sample with a second solid support, said second solid support having immobilized thereon an indicator, said indicator being one which is susceptible to a detectable change upon action of said reporter enzyme; and
  (c) observing whether said indicator undergoes a detectable change, said detectable change being an indication of the absence of said inhibitor of said target hydrolase in said sample.

67. A method in accordance with claim 66 wherein said target hydrolase is selected from the group consisting of proteases, peptidases, lipases, nucleases, homo-oligosaccharidases, hetero-oligosaccharidases, homo-polysaccharidases, hetero-polysaccharidases, phosphatases, sulfatases, neuraminidases and esterases.

68. A method in accordance with claim 67 wherein said target hydrolase is a protease selected from the group consisting of aspartic proteases, serine proteases, thiol proteases, metallo proteases, acid proteases and alkaline proteases.

69. A method in accordance with claim 68 wherein said protease is an aspartic protease.

70. A method in accordance with claim 66 wherein said inhibitor is selected from the group consisting of inhibitors of proteases, peptidases, lipases, nucleases, homo-oligosaccharidases, hetero-oligosaccharidases, homo-polysaccharidases, hetero-polysaccharidases, phosphatases, sulfatases, neuraminidases and esterases.

71. A method in accordance with claim 70 wherein said inhibitor is an inhibitor of proteases.

72. A method in accordance with claim 71 wherein said inhibitor is an inhibitor of aspartic proteases selected from the group consisting of pepstatin, ovomacroglobulin, haloperidol, transition state mimetics, U-81749, H-261, MV7-101, A-75925, A-76928 and A-7003.

73. A method in accordance with claim 66 wherein said reporter enzyme is a signal generating enzyme not subject to inactivation by any agent present in said sample, including inactivating hydrolysis by any hydrolase activity present in said sample.

74. A method in accordance with claim 73 wherein said reporter enzyme is selected from the group consisting of peroxidases, phosphatases, oxidoreductases, dehydrogenases, transferases, isomerases, kinases, reductases, deaminases, catalases, urease and glucuronidase.

75. A method in accordance with claim 74 wherein said reporter enzyme is a peroxidase.

76. A method in accordance with claim 75 wherein said peroxidase is horseradish peroxidase.

77. A method in accordance with claim 66 wherein said first and second solid supports are independently selected from the group consisting of cellulose, agarose, dextran, polyacrylate, and polyacrylamide.

78. A method in accordance with claim 66 wherein said first and second solid supports are independently selected from the group consisting of chitin, sepharose, oxirane acrylic beads, polymeric dialdehyde, starch, collagen, keratin, elastin, bovine hide powder, bacterial cell wall peptidoglycan, nylon, polyethylene terephthalates, polycarbonates and controlled pore glass.

79. A method in accordance with claim 66 wherein said reporter enzyme is covalently attached to said first solid support through a linker molecule which is a substrate for said target hydrolase.

80. A method in accordance with claim 79 wherein said linker molecule is selected from the group consisting of proteins, carbohydrates, lipids, peptides, esters and nucleic acids.

81. A method in accordance with claim 80 wherein said linker molecule is a protein selected from the group consisting of azocasein, casein, κ-casein, immunoglobulins, hemoglobin, myoglobin, albumin, elastin, keratin and collagen.

82. A method in accordance with claim 66 wherein said indicator is a visual indicator.

83. A method in accordance with claim 82 wherein said visual indicator is a chromogenic indicator.

84. A method in accordance with claim 83 wherein said chromogenic indicator is an indicator for peroxidative activity.

85. A method in accordance with claim 84 wherein said chromogenic indicator is comprised of a hydroperoxide and a chromogen selected from the group consisting of guaiac, 2-2'-azino-bis(3-ethyl-benzthiazoline-6-sulfonic acid), tetramethylbenzidine, phenol, 4-aminoantipyrine, and 4,5dihydroxynaphthalene-2,7-disulfonic acid.

* * * * *